US012559763B2

(12) United States Patent
Gocal et al.

(10) Patent No.: US 12,559,763 B2
(45) Date of Patent: Feb. 24, 2026

(54) FAD2 GENES AND MUTATIONS

(71) Applicants: Cibus US LLC, San Diego, CA (US); Cibus Europe, B.V., Breda (NL)

(72) Inventors: Gregory F. W. Gocal, San Diego, CA (US); Mark Knuth, San Diego, CA (US)

(73) Assignees: Cibus US LLC, San Diego, CA (US); Cibus Europe B.V. (NL)

( * ) Notice: Subject to any disclaimer, the term of this patent is extended or adjusted under 35 U.S.C. 154(b) by 0 days.

(21) Appl. No.: 17/040,703

(22) PCT Filed: Apr. 4, 2019

(86) PCT No.: PCT/US2019/025881
§ 371 (c)(1),
(2) Date: Sep. 23, 2020

(87) PCT Pub. No.: WO2019/195611
PCT Pub. Date: Oct. 10, 2019

(65) Prior Publication Data
US 2021/0010013 A1 Jan. 14, 2021

Related U.S. Application Data

(60) Provisional application No. 62/652,623, filed on Apr. 4, 2018.

(51) Int. Cl.
*C12N 15/82* (2006.01)
*A01H 1/00* (2006.01)

(52) U.S. Cl.
CPC ......... *C12N 15/8213* (2013.01); *A01H 1/104* (2021.01); *C12N 15/8247* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,873,191 A | 10/1989 | Wagner et al. |
| 4,945,050 A | 7/1990 | Sanford et al. |
| 4,959,317 A | 9/1990 | Sauer |
| 4,987,071 A | 1/1991 | Cech et al. |
| 5,008,200 A | 4/1991 | Ranch et al. |
| 5,024,944 A | 6/1991 | Collins et al. |
| 5,100,792 A | 3/1992 | Sanford et al. |
| 5,204,253 A | 4/1993 | Sanford et al. |
| 5,219,746 A | 6/1993 | Brinegar et al. |
| 5,268,463 A | 12/1993 | Jefferson |
| 5,302,523 A | 4/1994 | Coffee et al. |
| 5,334,711 A | 8/1994 | Sproat et al. |
| 5,380,831 A | 1/1995 | Adang et al. |
| 5,399,680 A | 3/1995 | Zhu et al. |
| 5,424,412 A | 6/1995 | Brown et al. |
| 5,436,391 A | 7/1995 | Fujimoto et al. |
| 5,466,785 A | 11/1995 | de Framond |
| 5,484,956 A | 1/1996 | Lundquist et al. |
| 5,489,520 A | 2/1996 | Adams et al. |
| 5,543,508 A | 8/1996 | Haseloff et al. |
| 5,569,597 A | 10/1996 | Grimsley et al. |
| 5,593,874 A | 1/1997 | Brown et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,659,026 A | 8/1997 | Baszczynski et al. |
| 5,756,325 A | 5/1998 | Kmiec |
| 5,760,012 A | 6/1998 | Kmiec et al. |
| 5,780,296 A | 7/1998 | Holloman et al. |
| 5,792,633 A | 8/1998 | Schiestl et al. |
| 5,795,972 A | 8/1998 | Kmiec |
| 5,871,984 A | 2/1999 | Kmiec |
| 5,888,983 A | 3/1999 | Kmiec |
| 5,945,339 A | 8/1999 | Holloman et al. |
| 5,962,426 A | 10/1999 | Glazer |
| 5,986,053 A | 11/1999 | Ecker et al. |
| 6,004,804 A | 12/1999 | Kumar et al. |
| 6,010,907 A | 1/2000 | Kmiec et al. |
| 6,072,050 A | 6/2000 | Bowen et al. |
| 6,177,611 B1 | 1/2001 | Rice |

(Continued)

FOREIGN PATENT DOCUMENTS

| | | |
|---|---|---|
| CN | 101696415 A | 4/2010 |
| CN | 109182373 A | 1/2019 |

(Continued)

OTHER PUBLICATIONS

Sauer, Oligonucleotide-Mediated Genome Editing Provides Precision and Function to Engineered Nucleases and Antibiotics in Plants, Plant Physiology, Apr. 2016 (Year: 2016).*
Altschul et al., (1990). "Basic local alignment search tool," J. Mol. Biol., 215:403-410.
Altschul et al., (1997). "Gapped BLAST and PSI-BLAST: a new generation of protein database search programs," Nucleic Acids Res., 25:3389-402.
An et al., (1986). "Transformation of Tobacco, Tomato, Potato, and *Arabidopsis thaliana* Using a Binary Ti Vector System," Plant Physiol., 81:301-305.
Archer et al., (1990). "Current views on chloroplast protein import and hypotheses on the origin of the transport mechanism," J. Bioenerg. Biomemb., 22(6):789-810.
Arimondo et al., (2000). "Recognition and cleavage of DNA by rebeccamycin- or benzopyridoquinoxaline conjugated of triple helix-forming oligonucleotides," Bioorganic and Medicinal Chem., 8:777-784.

(Continued)

*Primary Examiner* — Weihua Fan
*Assistant Examiner* — Brian James Sullivan
(74) *Attorney, Agent, or Firm* — Morrison & Foerster LLP

(57) ABSTRACT

The present disclosure provides fatty acid desaturase 2 (FAD2) genes and plants and/or plant cells bearing one or more mutations in two or more FAD2 genes; as well as methods of making and using such plants. In some embodiments, plants producing seed oil with high oleic acid content are provided.

14 Claims, 2 Drawing Sheets

Specification includes a Sequence Listing.

(56) References Cited

U.S. PATENT DOCUMENTS

| | | | |
|---|---|---|---|
| 5,424,412 A | 6/1995 | Brown et al. | |
| 6,414,223 B1 * | 7/2002 | Kodali | C12N 15/8247 |
| | | | 800/270 |
| 6,479,292 B1 | 11/2002 | Metz et al. | |
| 6,489,127 B1 | 12/2002 | Duyk et al. | |
| 6,506,559 B1 | 1/2003 | Fire et al. | |
| 6,511,824 B1 | 1/2003 | Buchman et al. | |
| 6,573,099 B2 | 6/2003 | Graham | |
| 6,753,458 B1 | 6/2004 | Filho et al. | |
| 6,824,978 B1 | 11/2004 | Cox et al. | |
| 6,870,075 B1 | 3/2005 | Beetham et al. | |
| 6,924,146 B1 | 8/2005 | Wattler et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,060,500 B2 | 6/2006 | Metz et al. | |
| 7,070,934 B2 | 7/2006 | Cox et al. | |
| 7,220,719 B2 | 5/2007 | Case et al. | |
| 7,262,054 B2 | 8/2007 | Jamieson et al. | |
| 7,273,923 B2 | 9/2007 | Jamieson et al. | |
| 7,285,416 B2 | 10/2007 | Choo et al. | |
| 7,361,635 B2 | 4/2008 | Miller et al. | |
| 7,501,275 B2 | 3/2009 | Laplaza et al. | |
| 7,521,241 B2 | 4/2009 | Choo et al. | |
| 8,278,036 B2 | 10/2012 | Kariko et al. | |
| 8,338,157 B2 | 12/2012 | Jantz et al. | |
| 8,445,251 B2 | 5/2013 | Smith et al. | |
| 9,493,779 B2 | 11/2016 | Ainley et al. | |
| 9,920,303 B2 | 3/2018 | Laga et al. | |
| 10,087,454 B2 | 10/2018 | Bilyeu et al. | |
| 10,113,162 B2 | 10/2018 | Mathis et al. | |
| 10,208,315 B2 | 2/2019 | Wagner | |
| 10,494,642 B2 * | 12/2019 | Denolf | C12Y 114/19006 |
| 2003/0084473 A1 | 5/2003 | Gocal et al. | |
| 2003/0115641 A1 | 6/2003 | Dobres et al. | |
| 2003/0221211 A1 | 11/2003 | Rottmann et al. | |
| 2004/0029283 A1 | 2/2004 | Fillatti | |
| 2006/0137040 A1 | 6/2006 | Debonte et al. | |
| 2007/0163002 A1 | 7/2007 | Debonte et al. | |
| 2008/0168586 A1 | 7/2008 | Laga et al. | |
| 2009/0202703 A1 | 8/2009 | Despeghel et al. | |
| 2014/0090112 A1 * | 3/2014 | Cogan | C12N 15/8216 |
| | | | 800/298 |
| 2014/0150132 A1 | 5/2014 | Bancroft et al. | |
| 2014/0189906 A1 | 7/2014 | Gocal et al. | |
| 2017/0283820 A1 | 10/2017 | Hudson | |
| 2018/0087066 A1 | 3/2018 | Fillatti et al. | |
| 2019/0024103 A1 | 1/2019 | Mathis et al. | |
| 2019/0024106 A1 | 1/2019 | Denolf et al. | |

FOREIGN PATENT DOCUMENTS

| | | |
|---|---|---|
| CN | 101629206 A | 1/2020 |
| EP | 629387 A1 | 12/1994 |
| EP | 679657 B1 | 4/1996 |
| WO | WO-1998049350 A1 | 11/1998 |
| WO | WO-1999007865 A1 | 2/1999 |
| WO | WO-1999040789 A1 | 8/1999 |
| WO | WO-1999043838 A1 | 9/1999 |
| WO | WO-1999058702 A1 | 11/1999 |
| WO | WO-1999058723 A1 | 11/1999 |
| WO | WO-2007073149 A1 | 6/2007 |
| WO | WO-2008148223 A1 | 12/2008 |
| WO | WO-2009017665 A1 | 2/2009 |
| WO | WO-2013176772 A1 | 11/2013 |
| WO | WO-2014039692 A2 | 3/2014 |
| WO | WO-2014093661 A2 | 6/2014 |
| WO | WO-2017138986 A1 | 8/2017 |

OTHER PUBLICATIONS

Asano et al., (1994). "Transgenic plants of Agrostis alba obtained by electroporation-mediated direct gene transfer into protoplasts," Plant Cell Rep. 13:243-246.

Ayeres et al., (1994). "Genetic Transformation of Rice," Crit. Rev. Plant. Sci., 13:219-239.

Ballas et al., (1989). "Efficient functioning of plant promoter and poly(A) sites in Xenopus oocytes," Nucleic Acids Res., 17:7891-7903.

Barcelo et al., (1994). "Transgenic cereal (tritordeum) plants obtained at high efficiency by microprojectile bombardment of inflorescence tissue," Plant. J., 5:583-592.

Barsby et al., (1996). "A Rapid and Efficient Alternative Procedure for the Regeneration of Plants from Hypocotyl Protoplasts of Brassica napus," Plant Cell Reports, 5:101-103.

Becker et al., (1994). "Fertile transgenic wheat from microprojectile bombardment of scutellar tissue," Plant. J., 5:299-307.

Belousov et al., (1997). "Sequence-specific targeting and covalent modification of human genomic DNA," Nucleic Acids Res, 25:3440-3444.

Bendinskas et al., (1998). "Sequence-Specific Photomodification of DNA by an Oligonucleotide-Phenanthrodihydrodioxin Conjugate," Bioconjugate Chem., 9:555-563. 1998.

Borkowska et al., (1995). "Transformation of diploid potato with an Agrobacterium tumefaciens binary vector system: II. Stability of transformation in tubers, micropropagated and greenhouse grown plants," Acta Physiologiae Plantarum, 3(17), 9 pages.

Brummelkamp et al., (2002). "A System for Stable Expression of Short Interfering RNAs in Mammalian Cells," Science, 296:550-553.

Burgess-Brown et al., (2008). "Codon optimization can improve expression of human genes in Escherichia coli: A multi-gene study," Protein Expr. Purif, 59:94-102.

Callis et al., (1987). "Introns increase gene expression in cultured maize cells," Genes and Development, 1:1183-1200.

Campbell et al., (1990). "Codon usage in higher plants, green algae, and cyanobacteria," Plant Physiol., 92:1-11.

Canevascini et al., (1996). "Tissue-Specific Expression and Promoter Analysis of the Tobacco Itp1 Gene," Plant Physiol., 112(2):513-524.

Capecchi, (1989). "Altering the genome by homologous recombination," Science, 244:1288-1292.

Casas et al., (1993). "Transgenic sorghum plants via microprojectile bombardment," Proc. Natl. Acad Sci. USA, 90:11212-11216.

Cermak et al., (2011). "Efficient design and assembly of custom TALEN and other TAL effector-based constructs for DNA targeting," Nucleic Acids Research, 39(12):e82, 11 pages.

Chee et al., (1992). "Transformation of cucumber tissues by microprojectile bombardment: identification of plants containing functional and non-functional transferred genes," Gene, 118:255-260.

Cheng et al., (2013). "Multiplexed activation of endogenous genes by CRISPR-on, an RNA-guided transcriptional activator system," Cell Research, 23(10):1163-71.

Christensen et al., (1989). "Sequence analysis and transcriptional regulation by heat shock of polyubiquitin transcripts from maize," Plant Mol. Biol., 12:619-632.

Christensen et al., (1992). "Maize polyubiquitin genes: structure, thermal perturbation of expression and transcript splicing, and promoter activity following transfer to protoplasts by electroporation," Plant Mol. Biol., 18:675-89.

Christou et al., (1992). "The development of a variety-independent gene-transfer method for rice," Trends in Biotechnology, 10:239-246.

Christou, (1993). "Philosophy and practice of variety-independent gene transfer into recalcitrant crops," In Vitro Cell. Dev. Biol.-Plant, 29:119-124.

Chuong et al., (1985). "A simple culture method for Brassica hypototyl protoplasts," Plant Cell Reports 4(1):4-6.

Clark et al., (1989). "Mutations at the transit peptide-mature protein junction separate two cleavage events during chloroplast import of the chlorophyll a/b-binding protein," J. Biol. Chem., 264:17544-17550.

(56)          References Cited

OTHER PUBLICATIONS

Colombier et al., (1996). "Interstrand Cross-linking Reaction in Triplexes Containing a Monofunctional Transplatin-Adduct," Nucleic Acids Research, 24:4519-4524.

Cong et al., (2013). "Multiplex Genome Engineering Using CRISPR/Cas Systems," Science, 339:819-823.

Coumans et al., (1989). "Plant development from isolated microspores of *Zea mays* L.," Plant Cell Rep., 7:618-621.

Cousins et al., (1991). "Transformation of an Australian Cotton Cultivar: Prospects for Cotton Improvement Through Genetic Engineering," Aust. J. Plant Physiol., 18:481-494.

Datta et al., (1990). "Embryogenesis and plant regeneration from microspores of both 'Indica' and 'Japonica' rice (*Oryza sativa*)," Plant Sci., 67:83-88.

Davies et al., (1993). "Transformation of peas," Plant Cell Rep., 12:180-183.

De Block, (1988). "Genotype-independent leaf disc transformation of potato (*Solanum tuberosum*) using Agrobacterium tumefaciens," Theor. Appl Genet., 76:767-774.

Della-Cioppa et al., (1987). "Protein Trafficking in Plant Cells," Plant Physiol., 84:965-968.

Dervan et al., (1999). "Sequence-specific DNA recognition by polyamides," Curr Opin Chem Biol, 3:688-693.

D'Halluin et al., (1992). "Transformation of Sugarbeet (*Beta vulgaris* L.) and Evaluation of Herbicide Resistance in Transgenic Plants," Bio/Technol., 10:309-314.

Dhir et al., (1992). "Regeneration of Fertile Plants from Protoplasts of Soybean (*Glycine max* L. *Merr.*): genotypic differences in culture response," Plant Cell Reports, 11:285-289.

Dong et al., (1993). "Transgenic flax plants from Agro-bacterium mediated transformation: incidence of chimeric regenerans and inheritance of transgenic plants," Plant Sci. 91:139-148.

Eapen et al., (1994). "Agrobacterium tumefaciens mediated gene transfer in peanut (*Arachis hypogaea* L.)," Plant Cell Rep., 13:582-586.

Faruqi et al., (1996). "Recombination induced by triple-helix-targeted DNA damage in mammalian cells," Mol Cell Biol, 16:6820-6828.

Fennell et al., (1992). "Electroporation and PEG delivery of DNA into maize microspores," Plant Cell Reports, 11:567-570.

Fire et al., (1998). "Potent and specific genetic interference by double-stranded RNA in Caenorhabditis elegans," Nature, 391:806-811.

Folger et al., (1982). "Patterns of integration of DNA microinjected into cultured mammalian cells: evidence for homologous recombination between injected plasmid DNA molecules," Mol Cell Biol, 2:1372-1387.

Frame et al., (1994). "Production of fertile transgenic maize plants by silicon carbide whisker-mediated transformation," Plant J., 6:941-948.

Franklin et al., (1993). "Genetic transformation of green bean callus via Agrobacterium mediated DNA transfer," Plant Cell Report, 12:74-79.

Fry et al., (1987). "Transformation of *Brassica napus* with Agrobacterium tumefaciens based vectors," Plant Cell Rep., 6:321-325.

Gallie et al., (1987). "Post-transcriptional regulation in higher eukaryotes: The role of the reporter gene in controlling expression," Nucleic Acid Res., 15:8693-8711.

Gallie et al., (1994). "The Regulation of Gene Expression in Transformed Maize Aleurone and Endosperm Protoplasts," Plant Physiol., 106:929-939.

Golovkin et al., (1993). "Production of transgenic maize plants by direct DNA uptake into embryogenic protoplasts," Plant Sci., 90:41-52.

Guerineau et al., (1991). "Effect of deletions in the cauliflower mosaic virus polyadenylation sequence on the choice of the polyadenylation sites in tobacco protoplasts," Mol. Gen. Genet., 262:141-144.

Guevara-Garcia et al., (1993). "Tissue-specific and wound-inducible pattern of expression of the mannopine synthase promoter is determined by the interaction between positive and negative cis-regulatory elements," Plant J., 4(3):495-505.

Gustafsson et al., (2004). "Codon bias and heterologous protein expression," Trends Biotechnol, 22:346-353.

Hammond et al., (2001). "Post-transcriptional gene silencing by double-stranded RNA," Nature Rev Gen, 2:110-119.

Hansen et al., (1997). "Wound-inducible and organ-specific expression of ORF13 from Agrobacterium rhizogenes 8196 T-DNA in transgenic tobacco plants," Mol. Gen Genet., 254(3):337-343.

Hartman et al., (1994). "Herbicide Resistant Turfgrass (*Agrostis palustris* Huds.) by Biolistic Transformation," Bio/Technology, 12:919-923.

Haun et al., (2014). "Improved soybean oil quality by targeted mutagenesis of the fatty acid desaturase 2 gene family," Plant Biotechnol J, 12:934-940.

Havre et al., (1993). "Targeted mutagenesis of DNA using triple helix-forming oligonucleotides linked to psoralen," Proc Nat'l Acad Sci, U.S.A., 90:7879-7883.

Havre et al., (1993). "Targeted mutagenesis of simian virus 40 DNA mediated by a triple helix-forming oligonucleotide," J Virol, 67:7324-7331.

Henikoff et al., (1989). "Amino acid substitution matrices from protein blocks," Proc. Natl. Acad. Sci. USA, 89:10915-10919.

International Search Report and Written Opinion mailed on Jul. 2, 2019, for PCT Patent Application No. PCT/US2019/025881 filed on Apr. 4, 2019, 18 pages.

Jardinaud et al., (1993). "Transient GUS gene expression in *Brassica napus* electroporated microspores," Plant Sci., 93:177-184.

Jinek et al., (2012). "A Programmable Dual-RNA-Guided DNA Endonuclease in Adaptive Bacterial Immunity," Science, 337:816-821.

Joshi et al., (1987). "Putative polyadenylation signals in nuclear genes of higher plants: a compilation and analysis," Nucleic Acid Res., 15:9627-9639.

Kagale et al., (2011). "EAR motif-mediated transcriptional repression in plants: an underlying mechanism for epigenetic regulation of gene expression," Epigenetics, 6(2):141-146.

Kane et al., (1995). "Specific cleavage of a DNA triple helix by Fell.bleomycin," Biochemistry, 34(51):16715-16724.

Karlin et al., (1993). "Applications and Statistics for Multiple High-Scoring Segments in Molecular Sequences," Proc Natl Acad. Sci., 90:5873-5877.

Kartha et al., "In vitro Plant Formation from Stem Explants of Rape," Physiol. Plant, 31:217-220, 1974.

Kawamata et al., (1997). "Temporal and spatial pattern of expression of the pea phenylalanine ammonia-lyase gene1 promoter in transgenic tobacco," Plant & cell physiology, 38(7):792-803.

Kim et al., (1996). "Hybrid restriction enzymes: zinc finger fusions to Fok I cleavage domain," Proceedings of the National Academy of Sciences of the United States of America, 93(3):1156-1160.

Kim et al., (2004). "DNA . RNA heteroduplex containing 8-oxo-7,8-dihydroguanosine: base pairing, structures, and thermodynamic stability," Journal of biochemistry and molecular biology, 37(6):657-662.

Kipp et al., (2000). "Gene targeting in plants via site-directed mutagenesis," Methods in molecular biology (Clifton, N.J.), 133:213-221.

Komatsuda et al. (1991). "Genotype X Sucrose Interactions for Somatic Embryogenesis in Soybeans," Crop Sci., 31:333-337.

Komatsuda et al., (1992). "Maturation and Germination of Somatic Embryos as Affected by Sucrose and Plant Growth Regulators in Soybeans *Glycine gracilis* Skvortz and *Glycine max* (L.) *Merr.*" Plant Cell, Tissue and Organ Culture, 28:103-113.

Krejsa et al., (1997). "Role of oxidative stress in the action of vanadium phosphotyrosine phosphatase inhibitors. Redox independent activation of NF-kappa," B. J Biol Chem, 272: 11541-11549.

Kunzelmann et al., (1996). "Gene targeting of CFTR DNA in CF epithelial cells," Gene therapy, 3(10):859-867.

Lakhssassi et al., (2017). "Characterization of the FAD2 Gene Family in Soybean Reveals the Limitations of Gel-Based Tilling in Genes with High Copy Norther," Front Plant Sci, 8(324):1-15.

(56)　　　　　　References Cited

OTHER PUBLICATIONS

Lam, (1994). "Analysis of tissue-specific elements in the CaMV 35S promoter," Results and problems in cell differentiation, 20:181-196.

Lamppa, (1988). "The chlorophyll a/b-binding protein inserts into the thylakoids independent of its cognate transit peptide," The Journal of biological chemistry, 263(29):14996-14999.

Lanza et al., (2014). "A condition-specific codon optimization approach for improved heterologous gene expression in Saccharomyces cerevisiae," BMC systems biology, 8:33.

Last et al., (1991). "pEmu: an improved promoter for gene expression in cereal cells," Theor. Appl. Genet., 81:581-8.

Lawrence et al., (1997). "Alterations in the Chlamydomonas plastocyanin transit peptide have distinct effects on in vitro import and in vivo protein accumulation," The Journal of biological chemistry, 272(33):20357-20363.

Li et al., (1982). "Somatic embryogenesis in quite a direct way in cultures of mesophyll protoplasts of Brassica napus L.," Plant Cell Reports, 1:209-211.

Lukhtanov et al., (1997). "Minor groove DNA alkylation directed by major groove triplex forming oligodeoxyribonucleotides," Nucleic acids research, 25(24):5077-5084.

Maeder et al., (2013). "CRISPR RNA-guided activation of endogenous human genes," Nature methods, 10(10):977-979.

Maheshwari et al., (1982). "Special Paper: Haploids From Pollen Grains—Retrospect and Prospect," American Journal of Botany, 69:865-879.

Mali et al., (2013). "CAS9 transcriptional activators for target specificity screening and paired nickases for cooperative genome engineering," Nature biotechnology, 31(9):833-838.

Maniatis et al., (1987). "Regulation of inducible and tissue-specific gene expression," Science (New York, N.Y.), 236(4806):1237-1245.

Martienssen, (1998). "Functional genomics: probing plant gene function and expression with transposons," Proceedings of the National Academy of Sciences of the United States of America, 95(5):2021-2026.

Matsuoka et al., (1993). "Tissue-specific light-regulated expression directed by the promoter of a C4 gene, maize pyruvate,orthophosphate dikinase, in a C3 plant, rice," Proceedings of the National Academy of Sciences of the United States of America, 90(20):9586-9590.

McBride et al., (1994). "Controlled expression of plastid transgenes in plants based on a nuclear DNA-encoded and plastid-targeted T7 RNA polymerase," Proceedings of the National Academy of Sciences of the United States of America, 91(15):7301-7305.

McElroy et al., (1990). "Isolation of an efficient actin promoter for use in rice transformation," Plant Cell, 2:163-171.

Mogen et al., (1990). "Upstream sequences other than AAUAAA are required for efficient messenger RNA 3'-end formation in plants," The Plant cell, 2(12):1261-1272.

Morlan et al., (2009). "Mutation detection by real-time PCR: a simple, robust and highly selective method," PloS one, 4(2):e4584.

Munroe et al., (1990). "Tales of poly(A): a review," Gene, 91(2):151-158.

Murray et al., (1989). "Codon usage in plant genes," Nucl. Acids Res., 17:477-98.

Myers et al., (1988). "Optimal alignments in linear space," Comput Appl Biosci., 4(1):11-7.

Narasimhulu et al., (1988). "Species Specific Shoot Regeneration Response of Cotyledonary Explants of Brassicas," Plant Cell Reports, 7(2):104-106.

Needleman et al., (1970). "A general method applicable to the search for similarities in the amino acid sequence of two proteins," J. Mol. Biol., 48:443-53.

Nehlin et al., (1995). "Induction of secondary embryogenesis in microspore-derived embryos of Brassica napus L.," Plant Sci., 111:219-227.

Núñez et al., (2000). "Long-range guanine oxidation in DNA restriction fragments by a triplex-directed naphthalene diimide intercalator," Biochemistry, 39(20):6190-6199.

Odell et al., (1985). "Identification of DNA sequences required for activity of the cauliflower mosaic virus 35S promoter," Nature, 313:810-2.

Oh et al., (1999). "Triple helix-forming oligonucleotides target psoralen adducts to specific chromosomal sequences in human cells," Nucl. Acids Res., 27:4734-4742.

Orozco et al., (1993). "Localization of light-inducible and tissue-specific regions of the spinach ribulose bisphosphate carboxylase/oxygenase (rubisco) activase promoter in transgenic tobacco plants," Plant molecular biology, 23(6):1129-1138.

Paddison et al., (2002). "Short hairpin RNAs (shRNAs) induce sequence-specific silencing in mammalian cells," Genes & development, 16(8):948-958.

Pandey et al., (1992). "Plant Regeneration from Leaf and Hypocotyl Explants of Glycine wightii (W. and A.) Verdc. var. longicauda," Japan J. Breed. 42:1-5.

Pearson et al., (1988). "Improved tools for biological sequence comparison," Proc. Natl. Acad. Sci., 85:2444-48.

Perez-Pinera et al., (2013). "RNA-guided gene activation by CRISPR-Cas9-based transcription factors," Nature methods, 10(10):973-976.

Pilch et al., (1999). "The thermodynamics of polyamide-DNA recognition: hairpin polyamide binding in the Minor Groove of duplex DNA," Biochemistry, 38:2143-2151.

Proudfoot, (1991). "Poly(A) signals," Cell, 64(4):671-674.

Raemakers et al., (1995). "Secondary somatic embryogenesis and applications in plant breeding," Euphytica, 81:93-107.

Raghavan, (1987). "Developmental strategies of the angiosperm pollen: a biochemical perspective," Cell differentiation, 21(4):213-226.

Rinehart et al., (1996). "Tissue-specific and developmental regulation of cotton gene FbL2A. Demonstration of promoter activity in transgenic plants," Plant physiology, 112(3):1331-1341.

Ritala et al., (1994). "Fertile transgenic barley to particle bombardment of immature embryos," Plant molecular biology, 24(2):317-325.

Römer et al., (1993). "Expression of the genes encoding the early carotenoid biosynthetic enzymes in Capsicum annuum," Biochemical and biophysical research communications, 196(3):1414-1421.

Rouet et al., (1994). "Expression of a site-specific endonuclease stimulates homologous recombination in mammalian cells," Proceedings of the National Academy of Sciences of the United States of America, 91(13):6064-6068.

Rubnitz et al., (1984). "The minimum amount of homology required for homologous recombination in mammalian cells," Molecular and cellular biology, 4(11):2253-2258.

Russell et al., (1997). "Tissue-specific expression in transgenic maize of four endosperm promoters from maize and rice," Transgenic research, 6(2):157-168.

Sanfaçon et al., (1991). "A dissection of the cauliflower mosaic virus polyadenylation signal," Genes & development, 5(1):141-149.

Schmidt et al., (1993). "A novel operon organization involving the genes for chorismate synthase (aromatic biosynthesis pathway) and ribosomal GTPase center proteins (L11, L1, L10, L12: rpIKAJL) in cyanobacterium Synechocystis PCC 6803," The Journal of biological chemistry, 268(36):27447-27457.

Schnell et al., (1991). "Signal peptide analogs derived from two chloroplast precursors interact with the signal recognition system of the chloroplast envelope," The Journal of biological chemistry, 266(5):3335-3342.

Segal et al., (1995). "Endonuclease-induced, targeted homologous extrachromosomal recombination in Xenopus oocytes," Proceedings of the National Academy of Sciences of the United States of America, 92(3):806-810.

Sergeyev et al., (1995). "Catalytic site-specific cleavage of a DNA-target by an oligonucleotide carrying bleomycin A5," Nucleic acids research, 23(21):4400-4406.

Shah et al., (1986). "Engineering herbicide tolerance in transgenic plants," Science, 233(4762):478-481.

Shetty et al., (1992). "Stimulation of In Vitro Shoot Organogenesis in Glycine max (Merrill.) by Allantoin and Amides," Plant Science, 81:245-251.

(56)                    References Cited

OTHER PUBLICATIONS

Silva Filho et al., (1996). "Mitochondrial and chloroplast targeting sequences in tandem modify protein import specificity in plant organelles," Plant Mol. Biol., 30:769-780.

Simopoulos, (2002). The importance of the ratio of omega-6/omega-3 essential fatty acids, Biomedicine & pharmacotherapy, 56(8):365-379.

Skuzeski et al., (1990). "Analysis of leaky viral translation termination codons in vivo by transient expression of improved beta-glucuronidase vectors," Plant molecular biology, 15(1):65-79.

Smith et al., (1981). "Comparison of biosequences," Adv. Appl. Math., 2:482-9.

Staub et al., (1993). "Accumulation of D1 polypeptide in tobacco plastids is regulated via the untranslated region of the psbA mRNA," The EMBO journal, 12(2):601-606.

Stephens et al., (1991). "Agronomic Evaluation of Tissue-Culture-Derived Soybean Plants," Theor. Appl. Genet. 82:633-635.

Sun et al., (1998). "Cotyledon-derived diploid and haploid protoplast culture and diploid plant regeneration in Brassica napus cv. 'Topas'," Can. J. Bot. 76:530-541.

Svab et al., (1990). "Stable transformation of plastids in higher plants," Proceedings of the National Academy of Sciences of the United States of America, 87(21):8526-8530.

Svab et al., (1993). "High-frequency plastid transformation in tobacco by selection for a chimeric aadA gene," Proceedings of the National Academy of Sciences of the United States of America, 90(3):913-917.

Swanson et al., (1987). "Efficient isolation of microspores and the production of microspore-derived embryos from Brassica napus," Plant cell reports, 6(2):94-97.

Takasugi et al., (1991). "Sequence-specific photo-induced cross-linking of the two strands of double-helical DNA by a psoralen covalently linked to a triple helix-forming oligonucleotide," Proceedings of the National Academy of Sciences of the United States of America, 88(13):5602-5606.

Takeshita et al., (1987). "Oligodeoxynucleotides containing synthetic abasic sites. Model substrates for DNA polymerases and apurinic/apyrimidinic endonucleases," The Journal of biological chemistry, 262(21):10171-10179.

Thompson et al., (1994). "CLUSTAL W: improving the sensitivity of progressive multiple sequence alignment through sequence weighting, position-specific gap penalties and weight matrix choice," Nucleic acids research, 22(22):4673-4680.

Timmons et al., (1998). "Specific interference by ingested dsRNA," Nature, 395(6705):854.

Van Camp et al., (1996). "Tissue-specific activity of two manganese superoxide dismutase promoters in transgenic tobacco," Plant physiology, 112(2):525-535.

Velten et al., (1984). "Isolation of a dual plant promoter fragment from the Ti plasmid of Agrobacterium tumefaciens," The EMBO journal, 3(12):2723-2730.

Von Heijne et al., (1991). "CHLPEP—A database of chloroplast transit peptides," Plant Mol Biol Rep 9:104-126.

Wan et al., (1994). "Generation of Large Numbers of Independently Transformed Fertile Barley Plants," Plant physiology, 104(1):37-48.

Wang et al., (1988). "Carcinogens can induce homologous recombination between duplicated chromosomal sequences in mouse L cells," Molecular and cellular biology, 8(1):196-202.

Wang et al., (1995). "Targeted mutagenesis in mammalian cells mediated by intracellular triple helix formation," Molecular and cellular biology, 15(3):1759-1768.

Wang et al., (1996). "Mutagenesis in mammalian cells induced by triple helix formation and transcription-coupled repair," Science, 271(5250):802-805.

Wang et al., (2008). "Hairpin RNAs derived from RNA polymerase II and polymerase III promoter-directed transgenes are processed differently in plants," RNA, 14(5):903-913.

Winkler et al., (1998). "PCR-based identification of T-DNA insertion mutants," Methods in molecular biology, 82:129-136.

Wong et al., (1987). "Homologous recombination between coinjected DNA sequences peaks in early to mid-S phase," Molecular and cellular biology, 7(6):2294-2295.

Yamamoto et al., (1994). "The promoter of a pine photosynthetic gene allows expression of a beta-glucuronidase reporter gene in transgenic rice plants in a light-independent but tissue-specific manner," Plant & cell physiology, 35(5):773-778.

Yamamoto et al., (1997). "Light-responsive elements of the tobacco PSI-D gene are located both upstream and within the transcribed region," The Plant journal: for cell and molecular biology, 12(2):255-265.

Zhang et al., (2013). "Transcription activator-like effector nucleases enable efficient plant genome engineering," Plant physiology, 161(1):20-27.

Zhao et al., (1995). "Immunological characterization and chloroplast localization of the tryptophan biosynthetic enzymes of the flowering plant Arabidopsis thaliana," The Journal of biological chemistry, 270(11):6081-6087.

Christou, (1994). "Genetic engineering of crop legumes and cereals: current status and recent advances," Agro. Food. Ind. Hi Tech., 5:17-27.

Abe et al., (2018). "Production of high oleic/low linoleic rice by genome editing," Plant Physiol. Biochem., 131:58-62. Abstract Only.

Al Amin et al., (2019). "CRISPR-Cas9 mediated targeted disruption of FAD2-2 microsomal omega-6 desaturase in soybean (Glycine max.L)," BMC Biotechnol., 19:9, 10 pages.

Bai et al., (2019). "Identification, characterization and field testing of Brassica napus mutants producing high-oleic oils," Plant J., 98(1):33-41.

Chen et al., (2015). "Development of high oleic oil crop platform in flax through RNAi-mediated multiple FAD2 gene silencing," Plant Cell Rep., 34:643-653. Abstract Only.

Demorest et al., (2016). "Direct stacking of sequence-specific nuclease-induced mutations to produce high oleic and low linolenic soybean oil," BMC Plant Biol., 16:225, 8 pages.

Extended European Search Report received for European Patent Application No. 19782430.3 mailed on Dec. 7, 2021, 8 pages.

Jiang et al., (2017). "Significant enhancement of fatty acid composition in seeds of the allohexaploid, Camelina sativa, using CRISPR/Cas9 gene editing," Plant Biotechnol J., 15:648-657.

Lee et al., (2011). "Environmental Stability of Oleic Acid Concentration in Seed Oil for Soybean Lines with FAD2-1A and FAD2-1B Mutant Genes," Crop Sci., 52:1290-1297.

Lee et al., (2018). "EMS-induced mutation of an endoplasmic reticulum oleate desaturase gene (FAD2-2) results in elevated oleic acid content in rapeseed (Brassica napus L.)," Euphytica, 214:28.

Okuzaki et al., (2018). "CRISPR/Cas9-mediated genome editing of the fatty acid desaturase 2 gene in Brassica napus," Plant Physiol. Biochem, 131:63-69. Abstract Only.

Pham et al., (2010). "Mutant alleles of FAD2-1A and FAD2-1B combine to produce soybeans with the high oleic acid seed oil trait," BMC Plant Biol., 10:195, 13 pages.

Pham et al., (2012). "Combinations of mutant FAD2 and FAD3 genes to produce high oleic acid and low linolenic acid soybean oil," Theor Appl Genet., 125:503-515. Abstract Only.

Qu et al., (2012). "Development of marker-free transgenic Jatropha plants with increased levels of seed oleic acid," Biotechnology for Biofuels, 5:10, 11 pages.

Shockey et al., (2017). "Naturally occurring high oleic acid cottonseed oil: identification and functional analysis of a mutant allele of Gossypium barbadense fatty acid desaturase-2," Planta, 245:611-622. Abstract Only.

Wang et al., (2011). "FAD2 Gene Mutations Significantly Alter Fatty Acid Profiles in Cultivated Peanuts (Arachis hypogaea)," Biochemical Genetics, 19(11-12):748-759.

Wang et al., (2018). "Changes of Seed Weight, Fatty Acid Composition, and Oil and Protein Contents from Different Peanut FAD2 Genotypes at Different Seed Developmental and Maturation Stages," J. Agric. Food Chem., 66:3658-3665. Abstract Only.

Wen et al., (2018). "TALEN-mediated targeted mutagenesis of fatty acid desaturase 2 (FAD2) in peanut (Arachis hypogaea L.) promotes the accumulation of oleic acid," Plant Mol. Biol., 97:177-185.

(56)                    References Cited

OTHER PUBLICATIONS

Wood et al., (2018). "Seed-specific RNAi in safflower generates a super high oleic oil with extended oxidative stability," Plant Biotechnol. J., 16:1788-1796.

Yang et al., (2012). "Identification of FAD2 and FAD3 genes in *Brassica napus* genome and development of allele-specific markers for high oleic and low linolenic acid contents," Theor Appl Genet, 125:715-729.

Yang et al., (2018). "Improved oil quality in transgenic soybean seeds by RNAi-mediated knockdown of GmFAD2-1B," Transgenic Res., 27:155-166. Abstract Only.

Zaplin et al., (2013). "Production of high oleic rice grains by suppressing the expression of the OsFAD2-1 gene," Funct Plant Biol., 40:996-1004, 9 pages.

* cited by examiner

SEQUENCE LISTING

<160> NUMBER OF SEQ ID NOS: 54

<210> SEQ ID NO 1
<211> LENGTH: 1155
<212> TYPE: DNA
<213> ORGANISM: Brassica napus

<400> SEQUENCE: 1

```
atgggtgcag gtggaagaat gcaagtgtct cctccctcca aaaagtctga aaccgacaac        60
atcaagcgcg taccctgcga gacaccgccc ttcactgtcg gagaactcaa gaaagcaatc       120
ccaccgcact gtttcaaacg ctcgatccct cgctctttct cctacctcat ctgggacatc       180
atcatagcct cctgcttcta ctacgtcgcc accacttact tccctctcct ccctcaccct       240
ctctcctact tcgcctggcc tctctactgg gcctgccagg gctgcgtcct aaccggcgtc       300
tgggtcatag cccacgagtg cggccaccac gccttcagcg actaccagtg gctggacgac       360
accgtcggcc tcatcttcca ctccttcctc ctcgtccctt acttctcctg gaagtacagt       420
catcgacgcc accattccaa cactggctcc ctcgagagag acgaagtgtt tgtccccaag       480
aagaagtcag acatcaagtg gtacggcaag tacctcaaca acccctttggg acgcaccgtg      540 atgttaacgg ttcagttcac tctcggctgg cctttgtact tagccttcaa cgtctcgggg       600
agaccttacg acggcggctt cgcttgccat ttccacccca acgctcccat ctacaacgac       660
cgtgagcgtc tccagatata catctccgac gctggcatcc tcgccgtctg ctacggtctc       720
taccgctacg ctgctgtcca aggagttgcc tcgatggtct gcttctacgg agttcctctt       780
ctgattgtca acgggttctt agttttgatc acttacttgc agcacacgca tccttccctg       840
cctcactatg actcgtctga gtgggattgg ttgaggggag ctttggccac cgttgacaga       900
gactacggaa tcttgaacaa ggtcttccac aatatcacgg acacgcacgt ggcgcatcac       960
ctgttctcga ccatgccgca ttatcatgcg atggaagcta cgaaggcgat aaagccgata      1020
ctgggagagt attatcagtt cgatgggacg ccggtggtta aggcgatgtg gagggaggcg      1080
aaggagtgta tctatgtgga accggacagg caaggtgaga agaaaggtgt gttctggtac      1140
aacaataagt tatga                                                       1155
```

<210> SEQ ID NO 2
<211> LENGTH: 1155
<212> TYPE: DNA
<213> ORGANISM: Brassica napus

<400> SEQUENCE: 2

```
atgggtgcag gtggaagaat gcaagtgtct cctccctcca agaagtctga aaccgacacc        60
atcaagcgcg taccctgcga gacaccgccc ttcactgtcg gagaactcaa gaaagcaatc       120
ccaccgcact gtttcaaacg ctcgatccct cgctctttct cctacctcat ctgggacatc       180
atcatagcct cctgcttcta ctacgtcgcc accacttact tccctctcct ccctcaccct       240
ctctcctact tcgcctggcc tctctactgg gcctgccaag ggtgcgtcct aaccggcgtc       300
tgggtcatag cccacgagtg cggccaccac gccttcagcg actaccagtg gcttgacgac       360
accgtcggtc tcatcttcca ctccttcctc ctcgtccctt acttctcctg gaagtacagt       420
catcgacgcc accattccaa cactggctcc ctcgagagag acgaagtgtt tgtccccaag       480
aagaagtcag acatcaagtg gtacggcaag tacctcaaca acccctttggg acgcaccgtg      540 atgttaacgg ttcagttcac tctcggctgg ccgttgtact tagccttcaa cgtctcggga       600
agaccttacg acggcggctt cgcttgccat ttccacccca acgctcccat ctacaacgac       660
```

```
cgcgagcgtc tccagatata catctccgac gctggcatcc tcgccgtctg ctacggtctc      720
ttccgttacg ccgccgcgca gggagtggcc tcgatggtct gcttctacgg agtcccgctt      780
ctgattgtca atggtttcct cgtgttgatc acttacttgc agcacacgca tccttccctg      840
cctcactacg attcgtccga gtgggattgg ttgaggggag ctttggctac cgttgacaga      900
gactacggaa tcttgaacaa ggtcttccac aatattaccg acacgcacgt ggcgcatcat      960
ctgttctcca cgatgccgca ttatcacgcg atggaagcta ccaaggcgat aaagccgata     1020
ctgggagagt attatcagtt cgatgggacg ccggtggtta aggcgatgtg gagggaggcg     1080
aaggagtgta tctatgtgga accggacagg caaggtgaga agaaaggtgt gttctggtac     1140
aacaataagt tatga                                                       1155
```

<210> SEQ ID NO 3
<211> LENGTH: 1141
<212> TYPE: DNA
<213> ORGANISM: Brassica napus

<400> SEQUENCE: 3

```
atgggcgcag gtggaagaat gcaagtctct cctccctcca gctcccccgg aaccaacacc       60
ctcaaacgcg tcccctgcga gacaccacca ttcactctcg gagacctcaa gaaagcaatc      120
ccacctcact gcttcaaacg ctccatccca cgctccttct cctcttcgac atcatcatct      180
cctcctcggc tcctccctct accacctctc cacagcctac ttccctctcc cttacctcgc      240
ctgacccctc tactgggcct gccaaggctg cgtcctaacg ggcctctggg tcatagccca      300
cgagtgcggc caccacgcct tcagcgacca ccagtggctg gacgacgccg ccggcctcgt      360
cttccactcc ttcctcctcg tcccgtactt ctcctggaag tacatccatg acgccaccat      420
tccaacaccg gatccctcga tagggacgaa gtgttcgtcc ccaagaagaa atccgacatc      480
aagtggtacg gcaagtacct caacaacccg ctaggacgca cggtgatgct aaccgtccag      540
ttcaagctcg gctggccgtt gtacttagcc ttcaacgtct cgggaagacc ttacagcgac      600
ggtttcgctt gccatttcca cccgaacgct cccatctaca acgaccgcga gcgtctccag      660
atatacatct ctgacgctgg cgtcctctcc gtatgttacg gtctctaccg ttacgctgct      720
tcgcgaggag tagcctctgt ggtctgtgtc tacggagttc cgcttctaat tgtcaactgt      780
ttcctcgtct tgatcactta cttgcagcac acgcaccctt cgctgcctca ctatgattct      840
tccgagtggg attggttgag aggagctttg gctactgtgg atagagacta tggaatcttg      900
aacaaggtgt ccataacat cacgacacg cacgtggcgc atcatctgtt ctcgacgatg       960
ccgcattata cgcgatgga gcgaccaag gcgataaagc cgatactttg gagagtatta      1020
ccagtttgat ggaacgccgg cggttaaggc gatgtggagg gaggcgaagg agtgtatcta     1080
tgttgaaccg gataggcaag gtgagaagaa aggtgtgttc tggtacaaca ataagttatg     1140
a                                                                     1141
```

<210> SEQ ID NO 4
<211> LENGTH: 1155
<212> TYPE: DNA
<213> ORGANISM: Brassica napus

<400> SEQUENCE: 4

```
atgggcgcag gtggaagaat gcaagtctct cctccctcca gctcccccga aaccaaaacc       60
ctcaaacgcg tccctgcga gacaccaccc ttcactctcg gagacctcaa gaaagcaatc      120
```

-continued

```
ccacctcact gcttcaaacg ctccatccct cgctccttct cctacctcct cttcgacatc    180
ctcgtctcct cctccctcta ccacctctcc acagcctact tccctctcct cccccaccct    240
ctcccttacc tcgcctggcc cctctactgg gcctgccaag gctgcgtcct aacgggcctc    300
tgggtcatcg cccacgaatg cggccaccac gccttcagcg accaccagtg gctggacgac    360
gccgtgggcc tcgtcttcca ctccttcctc ctcgtccctt acttctcctg gaagtacagc    420
catcgacgcc accattccaa caccggatcc ctcgagaggg atgaagtgtt cgtccccaag    480
aagaaatccg acatcaagtg gtacggaaag tacctcaaca acccgctagg acgcacggtg    540
atgctaaccg tccagttcac gctcggctgg ccgttgtact tagccttcaa cgtctctgga    600
agaccttaca gcgacggttt cgcttgccat ttccacccga acgctcccat ctacaacgac    660
cgcgagcgtc tccagatata catctctgac gctggcgtcc tctccgtatg ttacggtctc    720
taccgctacg ctggttcgcg aggagtggcc tcgatggtct gtgtctacgg agttccgctt    780
atgattgtca actgtttcct cgtcttgatc acttacttgc agcacacgca cccttcgctg    840
cctcactatg attcttcgga gtgggattgg ttgagaggag ctttggctac tgtggataga    900
gactatggaa tcttgaacaa ggtgtttcat aacatcacgg acacgcacgt ggcgcatcat    960
ctgttctcga cgatgccgca ttataacgcg atggaagcga ccaaggcgat aaagccgata   1020
cttggagagt attaccagtt tgatggaacg ccggtggtta aggcgatgtg gagggaggcg   1080
aaggagtgta tctatgttga accggatagg caaggtgaga agaaaggtgt gttctggtac   1140
aacaataagt tatga                                                    1155

<210> SEQ ID NO 5
<211> LENGTH: 384
<212> TYPE: PRT
<213> ORGANISM: Brassica napus

<400> SEQUENCE: 5

Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190
```

-continued

```
Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
        210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
        290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
        370                 375                 380
```

```
<210> SEQ ID NO 6
<211> LENGTH: 384
<212> TYPE: PRT
<213> ORGANISM: Brassica napus

<400> SEQUENCE: 6
```

```
Met Gly Ala Gly Gly Arg Met Gln Val Ser Pro Pro Ser Lys Lys Ser
1                   5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
        130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175
```

```
Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
            370                 375                 380

<210> SEQ ID NO 7
<211> LENGTH: 384
<212> TYPE: PRT
<213> ORGANISM: Brassica napus

<400> SEQUENCE: 7

Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
        130                 135                 140

His Ser Asn Thr Gly Ser Leu Glu Arg Asp Glu Val Phe Val Pro Lys
145                 150                 155                 160
```

-continued

```
Lys Lys Ser Asp Ile Lys Trp Tyr Gly Lys Tyr Leu Asn Asn Pro Leu
              165             170             175

Gly Arg Thr Val Met Leu Thr Val Gln Phe Thr Leu Gly Trp Pro Leu
              180             185             190

Tyr Leu Ala Phe Asn Val Ser Gly Arg Pro Tyr Asp Gly Gly Phe Ala
              195             200             205

Cys His Phe His Pro Asn Ala Pro Ile Tyr Asn Asp Arg Glu Arg Leu
              210             215             220

Gln Ile Tyr Ile Ser Asp Ala Gly Ile Leu Ala Val Cys Tyr Gly Leu
225             230             235             240

Tyr Arg Tyr Ala Ala Val Gln Gly Val Ala Ser Met Val Cys Phe Tyr
              245             250             255

Gly Val Pro Leu Leu Ile Val Asn Gly Phe Leu Val Leu Ile Thr Tyr
              260             265             270

Leu Gln His Thr His Pro Ser Leu Pro His Tyr Asp Ser Ser Glu Trp
              275             280             285

Asp Trp Leu Arg Gly Ala Leu Ala Thr Val Asp Arg Asp Tyr Gly Ile
              290             295             300

Leu Asn Lys Val Phe His Asn Ile Thr Asp Thr His Val Ala His His
305             310             315             320

Leu Phe Ser Thr Met Pro His Tyr His Ala Met Glu Ala Thr Lys Ala
              325             330             335

Ile Lys Pro Ile Leu Gly Glu Tyr Tyr Gln Phe Asp Gly Thr Pro Val
              340             345             350

Val Lys Ala Met Trp Arg Glu Ala Lys Glu Cys Ile Tyr Val Glu Pro
              355             360             365

Asp Arg Gln Gly Glu Lys Lys Gly Val Phe Trp Tyr Asn Asn Lys Leu
              370             375             380
```

<210> SEQ ID NO 8
<211> LENGTH: 384
<212> TYPE: PRT
<213> ORGANISM: Brassica napus

<400> SEQUENCE: 8

```
Met Gly Ala Gly Gly Arg Met Gln Val Ser Pro Pro Ser Lys Lys Ser
1               5               10              15

Glu Thr Asp Asn Ile Lys Arg Val Pro Cys Glu Thr Pro Pro Phe Thr
              20              25              30

Val Gly Glu Leu Lys Lys Ala Ile Pro Pro His Cys Phe Lys Arg Ser
              35              40              45

Ile Pro Arg Ser Phe Ser Tyr Leu Ile Trp Asp Ile Ile Ile Ala Ser
              50              55              60

Cys Phe Tyr Tyr Val Ala Thr Thr Tyr Phe Pro Leu Leu Pro His Pro
65              70              75              80

Leu Ser Tyr Phe Ala Trp Pro Leu Tyr Trp Ala Cys Gln Gly Cys Val
              85              90              95

Leu Thr Gly Val Trp Val Ile Ala His Glu Cys Gly His His Ala Phe
              100             105             110

Ser Asp Tyr Gln Trp Leu Asp Asp Thr Val Gly Leu Ile Phe His Ser
              115             120             125

Phe Leu Leu Val Pro Tyr Phe Ser Trp Lys Tyr Ser His Arg Arg His
              130             135             140
```

-continued

```
His Ser Asn Thr Gly Ser Leu Glu Arg Asp Glu Val Phe Val Pro Lys
145             150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380
```

```
<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Leu Asp Leu Asn Arg Pro Pro Pro Val Glu Asn
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Leu Arg Leu Phe Gly Val Asn Met
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 11

Leu Lys Leu Phe Gly Val Trp Leu
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Leu Asp Leu Glu Leu Arg Leu Gly Phe Ala
1               5                   10

<210> SEQ ID NO 13
<211> LENGTH: 203
<212> TYPE: PRT
<213> ORGANISM: Artificial Sequence
<220> FEATURE:
<223> OTHER INFORMATION: Synthetic Construct

<400> SEQUENCE: 13

Glu Arg Ser Asn Ser Ile Glu Leu Arg Asn Ser Phe Tyr Gly Arg Ala
1               5                   10                  15

Arg Thr Ser Pro Trp Ser Tyr Gly Asp Tyr Asp Asn Cys Gln Gln Asp
            20                  25                  30

His Asp Tyr Leu Leu Gly Phe Ser Trp Pro Pro Arg Ser Tyr Thr Cys
        35                  40                  45

Ser Phe Cys Lys Arg Glu Phe Arg Ser Ala Gln Ala Leu Gly Gly His
    50                  55                  60

Met Asn Val His Arg Arg Asp Arg Ala Arg Leu Arg Leu Gln Gln Ser
65                  70                  75                  80

Pro Ser Ser Ser Ser Thr Pro Ser Pro Pro Tyr Pro Asn Pro Asn Tyr
                85                  90                  95

Ser Tyr Ser Thr Met Ala Asn Ser Pro Pro Pro His His Ser Pro Leu
            100                 105                 110

Thr Leu Phe Pro Thr Leu Ser Pro Pro Ser Ser Pro Arg Tyr Arg Ala
        115                 120                 125

Gly Leu Ile Arg Ser Leu Ser Pro Lys Ser Lys His Thr Pro Glu Asn
    130                 135                 140

Ala Cys Lys Thr Lys Lys Ser Ser Leu Leu Val Glu Ala Gly Glu Ala
145                 150                 155                 160

Thr Arg Phe Thr Ser Lys Asp Ala Cys Lys Ile Leu Arg Asn Asp Glu
                165                 170                 175

Ile Ile Ser Leu Glu Leu Glu Ile Gly Leu Ile Asn Glu Ser Glu Gln
            180                 185                 190

Asp Leu Asp Leu Glu Leu Arg Leu Gly Phe Ala
        195                 200

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
atcgagcgtt tgaaacagtg                                                   20

-continued

```
<210> SEQ ID NO 15
<211> LENGTH: 63
<212> TYPE: DNA
<213> ORGANISM: Artificial Sequence
<220> FEATURE:
<223> OTHER INFORMATION: Synthetic Construct

<400> SEQUENCE: 15
tgtaatacga ctcactatag gtcgagcgtt tgaaacagtg gttttagagc tagaaatagc      60
aag                                                                    63

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
atggagcgtt tgaagcagtg                                                  20

<210> SEQ ID NO 17
<211> LENGTH: 63
<212> TYPE: DNA
<213> ORGANISM: Artificial Sequence
<220> FEATURE:
<223> OTHER INFORMATION: Synthetic Construct

<400> SEQUENCE: 17
tgtaatacga ctcactatag gtggagcgtt tgaagcagtg gttttagagc tagaaatagc      60
aag                                                                    63

<210> SEQ ID NO 18
<211> LENGTH: 41
<212> TYPE: DNA
<213> ORGANISM: Artificial Sequence
<220> FEATURE:
<223> OTHER INFORMATION: Synthetic Construct

<400> SEQUENCE: 18
gaaagcaatc ccaccgcaca tgtttcaaac gctcgatccc t                          41

<210> SEQ ID NO 19
<211> LENGTH: 41
<212> TYPE: DNA
<213> ORGANISM: Artificial Sequence
<220> FEATURE:
<223> OTHER INFORMATION: Synthetic Construct

<400> SEQUENCE: 19
gaaagcaatc ccaccgcacc tgtttcaaac gctcgatccc t                          41

<210> SEQ ID NO 20
<211> LENGTH: 41
<212> TYPE: DNA
<213> ORGANISM: Artificial Sequence
<220> FEATURE:
<223> OTHER INFORMATION: Synthetic Construct

<400> SEQUENCE: 20
gaaagcaatc ccaccgcacg tgtttcaaac gctcgatccc t                          41

<210> SEQ ID NO 21
```

-continued

```
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21
gaaagcaatc ccaccgcact tgtttcaaac gctcgatccc t                    41

<210> SEQ ID NO 22
<211> LENGTH: 39
<212> TYPE: DNA
<213> ORGANISM: Artificial Sequence
<220> FEATURE:
<223> OTHER INFORMATION: Synthetic Construct

<400> SEQUENCE: 22
gaaagcaatc ccaccgcacg tttcaaacgc tcgatccct                       39

<210> SEQ ID NO 23
<211> LENGTH: 38
<212> TYPE: DNA
<213> ORGANISM: Artificial Sequence
<220> FEATURE:
<223> OTHER INFORMATION: Synthetic Construct

<400> SEQUENCE: 23
gaaagcaatc ccaccgcact ttcaaacgct cgatccct                        38

<210> SEQ ID NO 24
<211> LENGTH: 41
<212> TYPE: DNA
<213> ORGANISM: Artificial Sequence
<220> FEATURE:
<223> OTHER INFORMATION: Synthetic Construct

<400> SEQUENCE: 24
gaaagcaatc ccacctcaca tgcttcaaac gctccatccc a                    41

<210> SEQ ID NO 25
<211> LENGTH: 41
<212> TYPE: DNA
<213> ORGANISM: Artificial Sequence
<220> FEATURE:
<223> OTHER INFORMATION: Synthetic Construct

<400> SEQUENCE: 25
gaaagcaatc ccacctcacc tgcttcaaac gctccatccc a                    41

<210> SEQ ID NO 26
<211> LENGTH: 41
<212> TYPE: DNA
<213> ORGANISM: Artificial Sequence
<220> FEATURE:
<223> OTHER INFORMATION: Synthetic Construct

<400> SEQUENCE: 26
gaaagcaatc ccacctcacg tgcttcaaac gctccatccc a                    41

<210> SEQ ID NO 27
<211> LENGTH: 41
<212> TYPE: DNA
<213> ORGANISM: Artificial Sequence
<220> FEATURE:
<223> OTHER INFORMATION: Synthetic Construct
```

<400> SEQUENCE: 27
gaaagcaatc ccacctcact tgcttcaaac gctccatccc a                          41

<210> SEQ ID NO 28
<211> LENGTH: 39
<212> TYPE: DNA
<213> ORGANISM: Artificial Sequence
<220> FEATURE:
<223> OTHER INFORMATION: Synthetic Construct

<400> SEQUENCE: 28
gaaagcaatc ccacctcacg cttcaaacgc tccatccca                             39

<210> SEQ ID NO 29
<211> LENGTH: 38
<212> TYPE: DNA
<213> ORGANISM: Artificial Sequence
<220> FEATURE:
<223> OTHER INFORMATION: Synthetic Construct

<400> SEQUENCE: 29
gaaagcaatc ccacctcacc ttcaaacgct ccatccca                              38

<210> SEQ ID NO 30
<211> LENGTH: 136
<212> TYPE: PRT
<213> ORGANISM: Artificial Sequence
<220> FEATURE:
<223> OTHER INFORMATION: Synthetic Construct

<400> SEQUENCE: 30

Met Gly Ala Gly Gly Arg Met Gln Val Ser Pro Pro Ser Ser Ser Pro
1               5                   10                  15

Gly Thr Asn Thr Leu Lys Arg Val Pro Cys Glu Thr Pro Pro Phe Thr
            20                  25                  30

Leu Gly Asp Leu Lys Lys Ala Ile Pro Pro His Cys Phe Lys Arg Ser
        35                  40                  45

Ile Pro Arg Ser Phe Ser Ser Ser Thr Ser Ser Ser Pro Pro Arg Leu
    50                  55                  60

Leu Pro Leu Pro Pro Leu His Ser Leu Leu Pro Ser Pro Leu Pro Arg
65                  70                  75                  80

Leu Thr Pro Leu Leu Gly Leu Pro Arg Leu Arg Pro Asn Gly Pro Leu
                85                  90                  95

Gly His Ser Pro Arg Val Arg Pro Pro Arg Leu Gln Arg Pro Pro Val
            100                 105                 110

Ala Gly Arg Arg Arg Arg Pro Arg Leu Pro Leu Leu Pro Pro Arg Pro
        115                 120                 125

Val Leu Leu Leu Glu Val His Pro
    130                 135

<210> SEQ ID NO 31
<211> LENGTH: 384
<212> TYPE: PRT
<213> ORGANISM: Artificial Sequence
<220> FEATURE:
<223> OTHER INFORMATION: Synthetic Construct

<400> SEQUENCE: 31

Met Gly Ala Gly Gly Arg Met Gln Val Ser Pro Pro Ser Ser Ser Pro
1               5                   10                  15

-continued

```
Glu Thr Lys Thr Leu Lys Arg Val Pro Cys Glu Thr Pro Pro Phe Thr
        20                  25                  30

Leu Gly Asp Leu Lys Lys Ala Ile Pro Pro His Cys Phe Lys Arg Ser
        35                  40                  45

Ile Pro Arg Ser Phe Ser Tyr Leu Leu Phe Asp Ile Leu Val Ser Ser
    50                  55                  60

Ser Leu Tyr His Leu Ser Thr Ala Tyr Phe Pro Leu Leu Pro His Pro
65                  70                  75                  80

Leu Pro Tyr Leu Ala Trp Pro Leu Tyr Trp Ala Cys Gln Gly Cys Val
                85                  90                  95

Leu Thr Gly Leu Trp Val Ile Ala His Glu Cys Gly His His Ala Phe
                100                 105                 110

Ser Asp His Gln Trp Leu Asp Asp Ala Val Gly Leu Val Phe His Ser
                115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Ser Asp Gly Phe Ala
                195                 200                 205

Cys His Phe His Pro Asn Ala Pro Ile Tyr Asn Asp Arg Glu Arg Leu
    210                 215                 220

Gln Ile Tyr Ile Ser Asp Ala Gly Val Leu Ser Val Cys Tyr Gly Leu
225                 230                 235                 240

Tyr Arg Tyr Ala Gly Ser Arg Gly Val Ala Ser Met Val Cys Val Tyr
                245                 250                 255

Gly Val Pro Leu Met Ile Val Asn Cys Phe Leu Val Leu Ile Thr Tyr
                260                 265                 270

Leu Gln His Thr His Pro Ser Leu Pro His Tyr Asp Ser Ser Glu Trp
                275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
    370                 375                 380
```

<210> SEQ ID NO 32
<211> LENGTH: 388
<212> TYPE: DNA
<213> ORGANISM: Brassica napus -continued

```
<400> SEQUENCE: 32
gcaggtggaa gaatgcaagt gtctcctccc tccaaaaagt ctgaaaccga caacatcaag        60
cgcgtaccct gcgagacacc gcccttcact gtcggagaac tcaagaaagc aatcccaccg       120
cactgtttca aacgctcgat ccctcgctct ttctcctacc tcatctggga catcatcata       180
gcctcctgct tctactacgt cgccaccact tacttccctc tcctccctca ccctctctcc       240
tacttcgcct ggcctctcta ctgggcctgc cagggctgcg tcctaaccgg cgtctgggtc       300
atagcccacg agtgcggcca ccacgccttc agcgactacc agtggctgga cgacaccgtc       360
ggcctcatct tccactcctt cctcctcg                                          388

<210> SEQ ID NO 33
<211> LENGTH: 389
<212> TYPE: DNA
<213> ORGANISM: Artificial Sequence
<220> FEATURE:
<223> OTHER INFORMATION: Synthetic Construct

<400> SEQUENCE: 33
gcaggtggaa gaatgcaagt gtctcctccc tccaaaaagt ctgaaaccga caacatcaag        60
cgcgtaccct gcgagacacc gcccttcact gtcggagaac tcaagaaagc aatcccaccg       120
cacttgtttc aaacgctcga tccctcgctc tttctcctac ctcatctggg acatcatcat       180
agcctcctgc ttctactacg tcgccaccac ttacttccct ctcctccctc accctctctc       240
ctacttcgcc tggcctctct actgggcctg ccagggctgc gtcctaaccg gcgtctgggt       300
catagcccac gagtgcggcc accacgcctt cagcgactac cagtggctgg acgacaccgt       360
cggcctcatc ttccactcct tcctcctcg                                         389

<210> SEQ ID NO 34
<211> LENGTH: 387
<212> TYPE: DNA
<213> ORGANISM: Artificial Sequence
<220> FEATURE:
<223> OTHER INFORMATION: Synthetic Construct

<400> SEQUENCE: 34
gcaggtggaa gaatgcaagt gtctcctccc tccaaaaagt ctgaaaccga caacatcaag        60
cgcgtaccct gcgagacacc gcccttcact gtcggagaac tcaagaaagc aatcccaccg       120
cacttttcaa acgctcgatc cctcgctctt tctcctacct catctggac atcatcatag        180 cctcctgctt ctactacgtc gccaccactt acttccctct cctccctcac cctctctcct       240
acttcgcctg gcctctctac tgggcctgcc agggctgcgt cctaaccggc gtctgggtca       300
tagcccacga gtgcggccac cacgccttca gcgactacca gtggctggac gacaccgtcg       360
gcctcatctt ccactccttc ctcctcg                                           387

<210> SEQ ID NO 35
<211> LENGTH: 387
<212> TYPE: DNA
<213> ORGANISM: Artificial Sequence
<220> FEATURE:
<223> OTHER INFORMATION: Synthetic Construct

<400> SEQUENCE: 35
gcaggtggaa gaatgcaagt gtctcctccc tccaaaaagt ctgaaaccga caacatcaag        60
cgcgtaccct gcgagacacc gcccttcact gtcggagaac tcaagaaagc aatcccaccg       120
```

```
cactgttcaa acgctcgatc cctcgctctt tctcctacct catctgggac atcatcatag      180
cctcctgctt ctactacgtc gccaccactt acttccctct cctccctcac cctctctcct      240
acttcgcctg gcctctctac tgggcctgcc agggctgcgt cctaaccggc gtctgggtca      300
tagcccacga gtgcggccac cacgccttca gcgactacca gtggctggac gacaccgtcg      360
gcctcatctt ccactccttc ctcctcg                                          387

<210> SEQ ID NO 36
<211> LENGTH: 386
<212> TYPE: DNA
<213> ORGANISM: Artificial Sequence
<220> FEATURE:
<223> OTHER INFORMATION: Synthetic Construct

<400> SEQUENCE: 36
gcaggtggaa gaatgcaagt gtctcctccc tccaaaaagt ctgaaaccga caacatcaag       60
cgcgtaccct gcgagacacc gcccttcact gtcggagaac tcaagaaagc aatcccaccg      120
cactttcaaa cgctcgatcc ctcgctcttt ctcctacctc atctgggaca tcatcatagc      180
ctcctgcttc tactacgtcg ccaccactta cttccctctc ctccctcacc ctctctccta      240
cttcgcctgg cctctctact gggcctgcca gggctgcgtc ctaaccggcg tctgggtcat      300
agcccacgag tgcggccacc acgccttcag cgactaccag tggctggacg acaccgtcgg      360
cctcatcttc cactccttcc tcctcg                                          386

<210> SEQ ID NO 37
<211> LENGTH: 388
<212> TYPE: DNA
<213> ORGANISM: Brassica napus

<400> SEQUENCE: 37
gcaggtggaa gaatgcaagt gtctcctccc tccaagaagt ctgaaaccga caccatcaag       60
cgcgtaccct gcgagacacc gcccttcact gtcggagaac tcaagaaagc aatcccaccg      120
cactgtttca aacgctcgat ccctcgctct ttctcctacc tcatctggga catcatcata      180
gcctcctgct tctactacgt cgccaccact tacttccctc ctccctca ccctctctcc      240 tacttcgcct ggcctctcta ctgggcctgc caagggtgcg tcctaaccgg cgtctgggtc      300
atagcccacg agtgcggcca ccacgccttc agcgactacc agtggcttga cgacaccgtc      360
ggtctcatct tccactcctt cctcctcg                                        388

<210> SEQ ID NO 38
<211> LENGTH: 389
<212> TYPE: DNA
<213> ORGANISM: Artificial Sequence
<220> FEATURE:
<223> OTHER INFORMATION: Synthetic Construct

<400> SEQUENCE: 38
gcaggtggaa gaatgcaagt gtctcctccc tccaagaagt ctgaaaccga caccatcaag       60
cgcgtaccct gcgagacacc gcccttcact gtcggagaac tcaagaaagc aatcccaccg      120
cacttgtttc aaacgctcga tccctcgctc tttctcctac ctcatctggg acatcatcat      180
agcctcctgc ttctactacg tcgccaccac ttacttccct ctcctccctc accctctctc      240
ctacttcgcc tggcctctct actgggcctg ccaagggtgc gtcctaaccg gcgtctgggt      300
catagcccac gagtgcggcc accacgcctt cagcgactac cagtggcttg acgacaccgt      360
cggtctcatc ttccactcct tcctcctcg                                       389
```

```
<210> SEQ ID NO 39
<211> LENGTH: 387
<212> TYPE: DNA
<213> ORGANISM: Artificial Sequence
<220> FEATURE:
<223> OTHER INFORMATION: Synthetic Construct

<400> SEQUENCE: 39
gcaggtggaa gaatgcaagt gtctcctccc tccaagaagt ctgaaaccga caccatcaag        60
cgcgtaccct gcgagacacc gcccttcact gtcggagaac tcaagaaagc aatcccaccg       120
catgtttcaa acgctcgatc cctcgctctt tctcctacct catctgggac atcatcatag       180
cctcctgctt ctactacgtc gccaccactt acttccctct cctccctcac cctctctcct       240
acttcgcctg gcctctctac tgggcctgcc aagggtgcgt cctaaccggc gtctgggtca       300
tagcccacga gtgcggccac cacgccttca gcgactacca gtggcttgac gacaccgtcg       360
gtctcatctt ccactccttc ctcctcg                                          387

<210> SEQ ID NO 40
<211> LENGTH: 387
<212> TYPE: DNA
<213> ORGANISM: Artificial Sequence
<220> FEATURE:
<223> OTHER INFORMATION: Synthetic Construct

<400> SEQUENCE: 40
gcaggtggaa gaatgcaagt gtctcctccc tccaagaagt ctgaaaccga caccatcaag        60
cgcgtaccct gcgagacacc gcccttcact gtcggagaac tcaagaaagc aatcccaccg       120
cacgtttcaa acgctcgatc cctcgctctt tctcctacct catctgggac atcatcatag       180
cctcctgctt ctactacgtc gccaccactt acttccctct cctccctcac cctctctcct       240
acttcgcctg gcctctctac tgggcctgcc aagggtgcgt cctaaccggc gtctgggtca       300
tagcccacga gtgcggccac cacgccttca gcgactacca gtggcttgac gacaccgtcg       360
gtctcatctt ccactccttc ctcctcg                                          387

<210> SEQ ID NO 41
<211> LENGTH: 386
<212> TYPE: DNA
<213> ORGANISM: Artificial Sequence
<220> FEATURE:
<223> OTHER INFORMATION: Synthetic Construct

<400> SEQUENCE: 41
gcaggtggaa gaatgcaagt gtctcctccc tccaagaagt ctgaaaccga caccatcaag        60
cgcgtaccct gcgagacacc gcccttcact gtcggagaac tcaagaaagc aatcccaccg       120
cactttcaaa cgctcgatcc ctcgctcttt ctcctacctc atctgggaca tcatcatagc       180
ctcctgcttc tactacgtcg ccaccactta cttccctctc ctccctcacc ctctctccta       240
cttcgcctgg cctctctact gggcctgcca agggtgcgtc ctaaccggcg tctgggtcat       300
agcccacgag tgcggccacc acgccttcag cgactaccag tggcttgacg acaccgtcgg       360
tctcatcttc cactccttcc tcctcg                                           386

<210> SEQ ID NO 42
<211> LENGTH: 385
<212> TYPE: DNA
<213> ORGANISM: Artificial Sequence
<220> FEATURE:
```

<223> OTHER INFORMATION: Synthetic Construct

<400> SEQUENCE: 42
gcaggtggaa gaatgcaagt gtctcctccc tccaagaagt ctgaaaccga caccatcaag        60
cgcgtaccct gcgagacacc gcccttcact gtcggagaac tcaagaaagc aatcccaccg       120
tgtttcaaac gctcgatccc tcgctctttc tcctacctca tctgggacat catcatagcc       180
tcctgcttct actacgtcgc caccacttac ttccctctcc tccctcaccc tctctcctac       240
ttcgcctggc tctctactg ggcctgccaa gggtgcgtcc taaccggcgt ctgggtcata       300
gcccacgagt gcggccacca cgccttcagc gactaccagt ggcttgacga caccgtcggt       360
ctcatcttcc actccttcct cctcg                                            385

<210> SEQ ID NO 43
<211> LENGTH: 384
<212> TYPE: DNA
<213> ORGANISM: Artificial Sequence
<220> FEATURE:
<223> OTHER INFORMATION: Synthetic Construct

<400> SEQUENCE: 43
gcaggtggaa gaatgcaagt gtctcctccc tccaagaagt ctgaaaccga caccatcaag        60
cgcgtaccct gcgagacacc gcccttcact gtcggagaac tcaagaaagc aatcccaccg       120
cattcaaacg ctcgatccct cgctctttct cctacctcat ctgggacatc atcatagcct       180
cctgcttcta ctacgtcgcc accacttact tccctctcct ccctcaccct ctctcctact       240
tcgcctggcc tctctactgg gcctgccaag ggtgcgtcct aaccggcgtc tgggtcatag       300
cccacgagtg cggccaccac gccttcagcg actaccagtg gcttgacgac accgtcggtc       360
tcatcttcca ctccttcctc ctcg                                            384

<210> SEQ ID NO 44
<211> LENGTH: 382
<212> TYPE: DNA
<213> ORGANISM: Artificial Sequence
<220> FEATURE:
<223> OTHER INFORMATION: Synthetic Construct

<400> SEQUENCE: 44
gcaggtggaa gaatgcaagt gtctcctccc tccaagaagt ctgaaaccga caccatcaag        60
cgcgtaccct gcgagacacc gcccttcact gtcggagaac tcaagaaagc aatcccaccg       120
cactaacgct cgatccctcg ctctttctcc tacctcatct gggacatcat catagcctcc       180
tgcttctact acgtcgccac cacttacttc cctctcctcc tcaccctct ctcctacttc       240 gcctggcctc tctactgggc ctgccaaggg tgcgtcctaa ccggcgtctg ggtcatagcc       300
cacgagtgcg gccaccacgc cttcagcgac taccagtggc ttgacgacac cgtcggtctc       360
atcttccact ccttcctcct cg                                              382

<210> SEQ ID NO 45
<211> LENGTH: 374
<212> TYPE: DNA
<213> ORGANISM: Brassica napus

<400> SEQUENCE: 45
gcaggtggaa gaatgcaagt ctctcctccc tccagctccc ccggaaccaa caccctcaaa        60
cgcgtcccct gcgagacacc accattcact ctcggagacc tcaagaaagc aatcccacct       120
cactgcttca aacgctccat cccacgctcc ttctcctctt cgacatcatc atctcctcct       180

-continued

```
cggctcctcc ctctaccacc tctccacagc ctacttccct ctcccttacc tcgcctgacc      240
cctctactgg gcctgccaag gctgcgtcct aacgggcctc tgggtcatag cccacgagtg      300
cggccaccac gccttcagcg accaccagtg gctggacgac gccgccggcc tcgtcttcca      360
ctccttcctc ctcg      374

<210> SEQ ID NO 46
<211> LENGTH: 375
<212> TYPE: DNA
<213> ORGANISM: Artificial Sequence
<220> FEATURE:
<223> OTHER INFORMATION: Synthetic Construct

<400> SEQUENCE: 46
gcaggtggaa gaatgcaagt ctctcctccc tccagctccc ccggaaccaa caccctcaaa       60
cgcgtcccct gcgagacacc accattcact ctcggagacc tcaagaaagc aatcccacct      120
cacttgcttc aaacgctcca tcccacgctc cttctcctct tcgacatcat catctcctcc      180
tcggctcctc cctctaccac ctctccacag cctacttccc tctcccttac ctcgcctgac      240
ccctctactg ggcctgccaa ggctgcgtcc taacgggcc ctgggtcata gcccacgagt      300
gcggccacca cgccttcagc gaccaccagt ggctggacga cgccgccggc ctcgtcttcc      360
actccttcct cctcg      375

<210> SEQ ID NO 47
<211> LENGTH: 388
<212> TYPE: DNA
<213> ORGANISM: Brassica napus

<400> SEQUENCE: 47
gcaggtggaa gaatgcaagt ctctcctccc tccagctccc ccgaaaccaa aaccctcaaa       60
cgcgtcccct gcgagacacc acccttcact ctcggagacc tcaagaaagc aatcccacct      120
cactgcttca aacgctccat ccctcgctcc ttctcctacc tcctcttcga catcctcgtc      180
tcctcctccc tctaccacct ctccacagc tacttccctc tcctccccca ccctctccct      240
tacctcgcct ggcccctcta ctgggcctgc caaggctgcg tcctaacggg cctctgggtc      300
atcgcccacg aatgcggcca ccacgccttc agcgaccacc agtggctgga cgacgccgtg      360
ggcctcgtct tccactcctt cctcctcg      388

<210> SEQ ID NO 48
<211> LENGTH: 389
<212> TYPE: DNA
<213> ORGANISM: Artificial Sequence
<220> FEATURE:
<223> OTHER INFORMATION: Synthetic Construct

<400> SEQUENCE: 48
gcaggtggaa gaatgcaagt ctctcctccc tccagctccc ccgaaaccaa aaccctcaaa       60
cgcgtcccct gcgagacacc acccttcact ctcggagacc tcaagaaagc aatcccacct      120
cacttgcttc aaacgctcca tccctcgctc cttctcctac ctcctcttcg acatcctcgt      180
ctcctcctcc ctctaccacc tctccacagc ctacttccct ctcctccccc accctctccc      240
ttacctcgcc tggcccctct actgggcctg ccaaggctgc gtcctaacgg gcctctgggt      300
catcgcccac gaatgcggcc accacgcctt cagcgaccac cagtggctgg acgacgccgt      360
gggcctcgtc ttccactcct tcctcctcg      389
```

```
<210> SEQ ID NO 49
<211> LENGTH: 387
<212> TYPE: DNA
<213> ORGANISM: Artificial Sequence
<220> FEATURE:
<223> OTHER INFORMATION: Synthetic Construct

<400> SEQUENCE: 49
gcaggtggaa gaatgcaagt ctctcctccc tccagctccc ccgaaaccaa aaccctcaaa      60
cgcgtcccct gcgagacacc acccttcact ctcggagacc tcaagaaagc aatcccacct     120
cacgcttcaa acgctccatc cctcgctcct tctcctacct cctcttcgac atcctcgtct     180
cctcctccct ctaccacctc tccacagcct acttccctct cctcccccac cctctccctt     240
acctcgcctg gcccctctac tgggcctgcc aaggctgcgt cctaacgggc ctctgggtca     300
tcgcccacga atgcggccac cacgccttca gcgaccacca gtggctggac gacgccgtgg     360
gcctcgtctt ccactccttc ctcctcg                                        387

<210> SEQ ID NO 50
<211> LENGTH: 385
<212> TYPE: DNA
<213> ORGANISM: Artificial Sequence
<220> FEATURE:
<223> OTHER INFORMATION: Synthetic Construct

<400> SEQUENCE: 50
gcaggtggaa gaatgcaagt ctctcctccc tccagctccc ccgaaaccaa aaccctcaaa      60
cgcgtcccct gcgagacacc acccttcact ctcggagacc tcaagaaagc aatcccacct     120
cacttcaaac gctccatccc tcgctccttc tcctacctcc tcttcgacat cctcgtctcc     180
tcctccctct accacctctc cacagcctac ttccctctcc tcccccaccc tctcccttac     240
ctcgcctggc ccctctactg ggcctgccaa ggctgcgtcc taacgggcct ctgggtcatc     300
gcccacgaat gcggccacca cgccttcagc gaccaccagt ggctggacga cgccgtgggc     360
ctcgtcttcc actccttcct cctcg                                          385

<210> SEQ ID NO 51
<211> LENGTH: 389
<212> TYPE: DNA
<213> ORGANISM: Artificial Sequence
<220> FEATURE:
<223> OTHER INFORMATION: Synthetic Construct

<400> SEQUENCE: 51
gcaggtggaa gaatgcaagt gtctcctccc tccaaaaagt ctgaaaccga caacatcaag      60
cgcgtaccct gcgagacacc gcccttcact gtcggagaac tcaagaaagc aatcccaccg     120
cacttgtttc aaacgctcga tccctcgctc tttctcctac ctcatctggg acatcatcat     180
agcctcctgc ttctactacg tcgccaccac ttacttccct ctcctccctc accctctctc     240
ctacttcgcc tggcctctct actgggcctg ccagggctgc gtcctaaccg gcgtctgggt     300
catagcccac gagtgcggcc accacgcctt cagcgactac cagtggctgg acgacaccgt     360
cggcctcatc ttccactcct tcctcctcg                                      389

<210> SEQ ID NO 52
<211> LENGTH: 389
<212> TYPE: DNA
<213> ORGANISM: Artificial Sequence
<220> FEATURE:
<223> OTHER INFORMATION: Synthetic Construct
```

-continued

```
<400> SEQUENCE: 52
gcaggtggaa gaatgcaagt gtctcctccc tccaagaagt ctgaaaccga caccatcaag       60
cgcgtaccct gcgagacacc gcccttcact gtcggagaac tcaagaaagc aatcccaccg      120
cacttgtttc aaacgctcga tccctcgctc tttctcctac ctcatctggg acatcatcat      180
agcctcctgc ttctactacg tcgccaccac ttacttccct ctcctccctc accctctctc      240
ctacttcgcc tggcctctct actgggcctg ccaagggtgc gtcctaaccg gcgtctgggt      300
catagcccac gagtgcggcc accacgcctt cagcgactac cagtggcttg acgacaccgt      360
cggtctcatc ttccactcct tcctcctcg                                        389

<210> SEQ ID NO 53
<211> LENGTH: 375
<212> TYPE: DNA
<213> ORGANISM: Artificial Sequence
<220> FEATURE:
<223> OTHER INFORMATION: Synthetic Construct

<400> SEQUENCE: 53
gcaggtggaa gaatgcaagt ctctcctccc tccagctccc ccggaaccaa caccctcaaa       60
cgcgtcccct gcgagacacc accattcact ctcggagacc tcaagaaagc aatcccacct      120
cacttgcttc aaacgctcca tcccacgctc cttctcctct tcgacatcat catctcctcc      180
tcggctcctc cctctaccac ctctccacag cctacttccc tctcccttac ctcgcctgac      240
ccctctactg ggcctgccaa ggctgcgtcc taacgggcct ctgggtcata gcccacgagt      300
gcggccacca cgccttcagc gaccaccagt ggctggacga cgccgccggc ctcgtcttcc      360
actccttcct cctcg                                                       375

<210> SEQ ID NO 54
<211> LENGTH: 388
<212> TYPE: DNA
<213> ORGANISM: Artificial Sequence
<220> FEATURE:
<223> OTHER INFORMATION: Synthetic Construct

<400> SEQUENCE: 54
gcaggtggaa gaatgcaagt ctctcctccc tccagctccc ccgaaaccaa aaccctcaaa       60
cgcgtcccct gcgagacacc acccttcact ctcggagacc tcaagaaagc aatcccacct      120
cactgcttca aacgctccat ccctcgctcc ttctcctacc tcctcttcga catcctcgtc      180
tcctcctccc tctaccacct ctccacagcc tacttccctc tcctccccca ccctctccct      240
tacctcgcct ggcccctcta ctgggcctgc caaggctgcg tcctaacggg cctctgggtc      300
atcgcccacg aatgcggcca ccacgccttc agcgaccacc agtggctgga cgacgccgtg      360
ggcctcgtct tccactcctt cctcctcg                                        388
```

FAD2 GENES AND MUTATIONS

CROSS-REFERENCE TO RELATED APPLICATIONS

This application is a national stage application under 35 U.S.C. § 371 of International Application No. PCT/US2019/025881, filed internationally on Apr. 4, 2019, which claims the benefit of U.S. Provisional Application No. 62/652,623, filed on Apr. 4, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165072000200SEQLIST.txt, date recorded: Sep. 3, 2020, size: 42 KB).

FIELD

The present disclosure relates to compositions and methods pertaining to novel plant genes and gene products and also to plants having one or more gene mutations. In particular, the present disclosure provides fatty acid desaturase 2 (FAD2) genes and plants and/or plant cells bearing one or more mutations in a FAD2 gene; as well as methods of making and using such plants. In some embodiments, the plant produces seed oil with a high oleic acid content.

BACKGROUND

Wells, Mol Breeding (2014) 33:349-362 discloses lines of *Brassica napus* and states "[s]everal lines had PUFA content of ~6% and oleic acid content of ~84% . . . ". PCT application WO 2014/039692 discloses compositions and methods to "generate a break in the FAD2 gene and then ligating into the break a nucleic acid molecule associated with one or more traits of interest is disclosed." The oleic acid content of canola oil affects the culinary, industrial, and commercial utility of canola oil. Currently, canola oil generally contains about 60% oleic acid, which is a lower value than is suitable for many applications. Accordingly, there exists a need for seed oil with high oleic acid content, as well as for improved plants that produce seed oil (e.g., canola oil) with high oleic acid content.

BRIEF SUMMARY

The present disclosure is based at least in part on plants having a mutation in a fatty acid desaturase 2 (FAD2) gene in a plant cell. In certain embodiments a plant or plant cell as provided herein is non-transgenic. In certain embodiments, provided is a plant (such as *Brassica* spp) having a mutation in a FAD2 gene and having higher levels of oleic acid ($18:1\Delta9^{cis}$) in the seed oil relative to wild type plants. In certain embodiments, provided is a plant (such as *Brassica* spp) having a mutation in a FAD2 gene and having reduced levels of either or both linoleic acid ($18:2\Delta9,12$) and linolenic acid ($18:3\Delta9,12,15$) in the seed oil relative to wild type plants. In certain embodiments, provided is a plant (such as *Brassica* spp) having a mutation in a FAD2 gene and having higher levels of oleic acid ($18:1\Delta9^{cis}$) and reduced levels of either or both linoleic acid ($18:2\Delta9,12$) and linolenic acid ($18:3\Delta9,12,15$) in the seed oil relative to wild type plants. In some embodiments of any of the aspects and embodiments provided herein, the plant or plant cell is non-transgenic. In certain aspects, the mutation, alteration or modification to a FAD2 gene includes an insertion or deletion. In some embodiments the mutation, alteration or modification is or includes a nucleotide change or substitution. In some embodiments of the method, the alteration, mutation or modification introduces a premature stop codon. In some embodiments the alteration, mutation or modification introduces a frame shift mutation. In some embodiments of the compositions and methods provided herein, the mutation relative to a wildtype a FAD2 gene is an +1, −1, −2 nucleotide insertion or deletion (InDel). In certain embodiments of the compositions and methods provided herein, the mutation relative to a wildtype a FAD2 gene is an +1, −1, −2 nucleotide insertion or deletion (InDel) created by a targeted mutation. In some embodiments of the methods provided herein, the mutation, modification or alteration in the FAD2 gene reduces or obviates the activity or expression of the FAD2 gene. In some embodiments, the plant or plant cell is a *Brassica* plant.

A fatty acid desaturase 2 (FAD2) gene as used herein means a gene having a sequence as represented by the *Brassica napus* FAD2-1 sequences as disclosed herein (BnFAD2-1 is SEQ ID NO:1; BnFAD2-2 is SEQ ID NO:2; BnFAD2-3 is SEQ ID NO:3; BnFAD2-4 is SEQ ID NO:4) or in certain embodiments, homologs, variants or mutants thereof. The term "FAD2 homolog" or any variation refers to a FAD2 gene or FAD2 gene product found in another species that performs the same or substantially the same biological function as the *Brassica* genes and gene products disclosed herein and where the nucleic acid sequences of the coding region or polypeptide sequences (of the FAD2 gene product) are said to be "identical" or at least 50%, or at least 60%, or at least 70%, or at least 75%, or at least 80%, or at least 85%, or at least 90%, or at least 92%, or at least 95%, or at least 96%, or at least 97%, or at least 98% or at least 99% similar (also referred to as "percent identity" or "substantially identical") to one or more of FAD2-1, FAD2-2, FAD2-3, or FAD2-4 sequences as disclosed herein.

In one aspect, provided is a plant or plant cell in which at least one of the FAD2-1, FAD2-2, FAD2-3 or FAD2-4 endogenous genes have a sequence that is different (for example by a gene alteration, mutation or modification) than any naturally occurring FAD2 gene; in some embodiments provided is a plant or plant cell in which at least two of the FAD2-1, FAD2-2, FAD2-3 or FAD2-4 endogenous genes have a sequence that is different (for example by a gene alteration, mutation or modification) than any naturally occurring FAD2 gene; in some embodiments provided is a plant or plant cell in which at least three of the FAD2-1, FAD2-2, FAD2-3 or FAD2-4 endogenous genes have a sequence that is different (for example by a gene alteration, mutation or modification) than any naturally occurring FAD2 gene; in some embodiments provided is a plant or plant cell having in which each of the FAD2-1, FAD2-2, FAD2-3 and FAD2-4 endogenous genes have a sequence that is different (for example by a gene alteration, mutation or modification) than any naturally occurring FAD2 gene.

In certain embodiments, provided is a plant or plant cell (such as *Brassica* spp) in which the FAD2-1 endogenous gene has a sequence that is different (for example by a gene alteration, mutation or modification) than a naturally occurring FAD2-1 gene. In certain embodiments, provided is a plant or plant cell (such as *Brassica* spp) in which the FAD2-1 endogenous gene has a sequence that has a +1, −1, −2 nucleotide insertion or deletion (InDel) difference as compared to a naturally occurring FAD2-1 gene. In certain embodiments, a plant or plant cell as provided herein has a gene FAD2 alteration, mutation or modification that is a +1, −1, −2 nucleotide insertion or deletion (InDel) created by a targeted mutation. In certain embodiments, a plant or plant cell as provided herein has a FAD2 gene alteration, mutation or modification that is created or developed by a targeted mutation. In certain embodiments, provided is a plant or plant cell (such as *Brassica* spp) in which the FAD2-2 endogenous gene has a sequence that is different (for example by a gene alteration, mutation or modification) than a naturally occurring FAD2-2 gene. In certain embodiments, provided is a plant or plant cell (such as *Brassica* spp) in which the FAD2-2 endogenous gene has a sequence that has a +1, −1, −2 nucleotide insertion or deletion (InDel) difference as compared to a naturally occurring FAD2-2 gene. In certain embodiments, provided is a plant or plant cell (such as *Brassica* spp) in which the FAD2-3 endogenous gene has a sequence that is different (for example by a gene alteration, mutation or modification) than a naturally occurring FAD2-3 gene. In certain embodiments, provided is a plant or plant cell (such as *Brassica* spp) in which the FAD2-3 endogenous gene has a sequence that has a +1, −1, −2 nucleotide insertion or deletion (InDel) difference as compared to a naturally occurring FAD2-3 gene. In certain embodiments, provided is a plant or plant cell (such as *Brassica* spp) in which the FAD2-4 endogenous gene has a sequence that is different (for example by a gene alteration, mutation or modification) than a naturally occurring FAD2-4 gene. In certain embodiments, provided is a plant or plant cell (such as *Brassica* spp) in which the FAD2-4 endogenous gene has a sequence that has a +1, −1, −2 nucleotide insertion or deletion (InDel) difference as compared to a naturally occurring FAD2-4 gene.

In certain embodiments, provided is a plant or plant cell (such as *Brassica* spp) in which the FAD2-1 and FAD2-2 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1 and FAD2-2 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-1 and FAD2-3 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1 and FAD2-3 endogenous genes have a sequence that have a +1, −1, −2 nucleotide insertion or deletion (InDel) difference as compared to the corresponding naturally occurring FAD2 genes.

In some embodiments, provided is a plant or a plant cell having a FAD2 gene alteration, mutation or modification as provided herein wherein the plant or plant cell further has a mutation causing resistance to an herbicide. In some embodiments, provided is a plant or a plant cell having a FAD2 gene alteration, mutation or modification as provided herein wherein the plant or plant cell further has a mutation causing resistance to a sulfonylurea herbicide. In certain embodiments, provided is a plant or a plant cell having a FAD2 gene alteration, mutation or modification as provided herein wherein the plant or plant cell from a BN2SU or 412SUR line. In certain embodiments, provided is a plant or a plant cell having a FAD2 gene alteration, mutation or modification as provided herein wherein the plant or plant cell from a BN2SU line. In certain embodiments, provided is a plant or a plant cell having a FAD2 gene alteration, mutation or modification as provided herein wherein the plant or plant cell from a 412SUR line.

In certain embodiments, provided is a plant or plant cell (such as *Brassica* spp) in which the FAD2-1 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1 and FAD2-4 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-2 and FAD2-3 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-2 and FAD2-3 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-2 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-2 and FAD2-4 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-3 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-3 and FAD2-4 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-1, FAD2-2 and FAD2-3 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1, FAD2-2 and FAD2-3 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-1, FAD2-2 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1, FAD2-2 and FAD2-4 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-1, FAD2-3 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1, FAD2-3 and FAD2-4 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-2, FAD2-3 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-2, FAD2-3 and FAD2-4 endogenous genes have a sequence that have a +1, −1, −2 nucleotide insertion or deletion (InDel) difference as compared to the corresponding naturally occurring FAD2 genes.

In certain embodiments, provided is a plant or plant cell (such as *Brassica* spp) in which the FAD2-1, FAD2-2, FAD2-3 and FAD2-4 endogenous genes have a sequence that is different (for example by a gene alteration, mutation or modification) than the corresponding naturally occurring FAD2 genes. In certain embodiments, provided is a plant or plant cell (such as *Brassica* spp) in which the FAD2-1, FAD2-2, FAD2-3 and FAD2-4 endogenous genes have a sequence that have a +1, −1, −2 nucleotide insertion or deletion (InDel) difference as compared to the corresponding naturally occurring FAD2 genes.

In some embodiments, a plant (such as *Brassica* spp) having a mutation in a FAD2 gene as provided herein produces seed oil having an oleic acid content of at least 68%, or at least 70%, or at least 72%, or at least 74%; or at least 76%; or at least 78%; or at least 79%; or at least 80%; or at least 81%; or at least 82%; or at least 83%; or at least 84%; or at least 84%; or at least 85%; or at least 86%; or at least 87%; or at least 88%; or at least 89%; or at least 90%; or at least 91%; or at least 92%; or at least 93%; or at least 94%; or at least 95%.

In some embodiments, a plant (such as *Brassica* spp) having a mutation in a FAD2 gene as provided herein produces seed oil having an oleic acid content between 68-72%; or between 70-76%; or between 72-80%; or between 74-80%; or between 74-82%; or between 76-82%; or between 78-82%; or between 80-84%; or between 82-88%; or between 82-89%; or between 84-90%; or between 86-90%.

In some embodiments, a plant (such as *Brassica* spp) having a mutation in a FAD2 gene as provided herein produces seed oil having an linoleic acid content that is less than 18%; or less than 16%; or less than 15%; or less than 14%; or less than 13%; or less than 12%; or less than 10%; or less than 9%; or less than 8%; or less than 7%; or less than 6%; or less than 5%; or less than 4%; or less than 3%; or less than 2%.

In some embodiments, a plant (such as *Brassica* spp) having a mutation in a FAD2 gene as provided herein produces seed oil having an oleic acid content of at least 68%, or at least 70%, or at least 72%, or at least 74%; or at least 76%; or at least 78%; or at least 79%; or at least 80%; or at least 81%; or at least 82%; or at least 83%; or at least 84%; or at least 84%; or at least 85%; or at least 86%; or at least 87%; or at least 88%; or at least 89%; or at least 90%; or at least 91%; or at least 92%; or at least 93%; or at least 94%; or at least 95%; and having an linoleic acid content that is less than 18%; or less than 16%; or less than 15%; or less than 14%; or less than 13%; or less than 12%; or less than 10%; or less than 9%; or less than 8%; or less than 7%; or less than 6%; or less than 5%; or less than 4%; or less than 3%; or less than 2%.

In some embodiments, a plant (such as *Brassica* spp) having a mutation in a FAD2 gene as provided herein produces seed oil having a linolenic acid content that is less than 10%; or less than 8%; or less than 6%; or less than 5%; or less than 4%; or less than 3%; or less than 2%.

In one aspect, provided is a seed oil obtained from a plant as provided herein.

In one aspect, provided is a method that includes mutating at least one endogenous FAD2 gene in a cell of a plant (such as *Brassica* spp), for example to make a plant or plant seed as provided herein. In some embodiments the method includes (1) introducing into plant cells a gene repair oligonucleobase with a targeted mutation in the FAD2 gene to produce plant cells with a mutant FAD2 gene; and (2) regenerating a non-transgenic plant having a mutated FAD2 gene from said selected plant cell. In some embodiments the method includes (1) introducing into plant cells a DNA cutter configured to specifically nick or cut a FAD2 gene to produce plant cells with a mutant FAD2 gene; and (2) regenerating a non-transgenic plant having a mutated FAD2 gene from said selected plant cell. In a related embodiment, provided is a method comprising contacting a cell with a DNA cutter configured to specifically nick or cut a FAD2 gene. In a related aspect, provided are methods of making a mutation in a FAD2 gene. In some embodiments the method or methods as described herein may include exposing the cell to a DNA cutter and a GRON. In certain embodiments the methods include exposing a cell to a DNA cutter and a GRON wherein said GRON is modified with one or more of a Cy3 group, 3PS group, and a 2'O-methyl group. In some embodiments the method or methods may include exposing the cell to a DNA cutter without exposing the cell to a GRON. In some embodiments that include exposure to a DNA cutter, the DNA cutter specifically targets a FAD2 gene. In some embodiments the DNA cutter is one or more selected from a CRISPR, which includes but is not limited to Cas9, Cpf1 and their corresponding homologues, orthologues and/or paralogues, a base editor, a TALEN, a zinc finger, meganuclease, and a DNA-cutting antibiotic. In some embodiments the DNA cutter can be plasmid (DNA), RNA and/or protein. In certain embodiments, the methods provided do not include contacting the plant or plant cell with any transgene. In certain embodiments, provided is a plant or plant cell generated by the methods disclosed herein.

In another aspect, the present disclosure relates to a plant or part thereof including at least one mutation in at least one, at least two, at least three, or four nucleic acid sequences encoding fatty acid desaturase 2 (FAD2) genes. In some embodiments, the nucleic acid sequences have at least 90% identity, at least 95% sequence identity, at least 98% sequence identity, or at least 99% sequence identity to nucleic acid sequences selected from the group of SEQ ID NO: 1, SEQ ID NO: 2, SEQ ID NO: 3, or SEQ ID NO: 4. In some embodiments, the nucleic acid sequences are selected from the group of SEQ ID NO: 1, SEQ ID NO: 2, SEQ ID NO: 3, or SEQ ID NO: 4. In some embodiments that may be combined with any of the preceding embodiments, the mutation is a frameshift mutation. In some embodiments, the frameshift mutation results in one or more nucleotide insertions or deletions as compared to the corresponding endogenous gene without the frameshift mutation. In some embodiments that may be combined with any of the preceding embodiments, the frameshift mutation results in a premature stop codon. In some embodiments that may be combined with any of the preceding embodiments, the mutation reduces or eliminates expression of the FAD2 gene and/or FAD2 polypeptide. In some embodiments that may be combined with any of the preceding embodiments, the plant produces seed oil including an oleic acid content of at least 68%, at least 70%, at least 72%, at least 74%, at least 76%, at least 78%, at least 79%, at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95%. In some embodiments, the plant produces seed oil including an oleic acid content of at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95%. In some embodiments that may be combined with any of the preceding embodiments, the plant produces seed oil including an oleic acid content of between 68-72%, between 70-76%, between 72-80%, between 74-80%, between 74-82%, between 76-82%, between 78-82%, between 80-84%, between 82-88%, between 82-89%, between 84-90%, or between 86-90%. In some embodiments that may be combined with any of the preceding embodiments, the plant produces seed oil including a linoleic acid content of less than 18%, less than 16%, less than 15%, less than 14%, less than 13%, less than 12%, less than 10%, less than 9%, less than 8%, less than 7%, less than 6%, less than 5%, less than 4%, less than 3%, or less than 2%. In some embodiments that may be combined with any of the preceding embodiments, the plant produces seed oil including an oleic acid content of at least 68%, at least 70%, at least 72%, at least 74%, at least 76%, at least 78%, at least 79%, at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95%; and including a linoleic acid content of less than 18%, less than 16%, less than 15%, less than 14%, less than 13%, less than 12%, less than 10%, less than 9%, less than 8%, less than 7%, less than 6%, less than 5%, less than 4%, less than 3%, or less than 2%. In some embodiments that may be combined with any of the preceding embodiments, the plant produces seeds and the seeds include oleic acid at a level of at least at least 68%, at least 70%, at least 72%, at least 74%, at least 76%, at least 78%, at least 79%, at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95% by weight of the total fatty acid content of the seeds. In some embodiments that may be combined with any of the preceding embodiments, the plant produces seeds and the seeds include oleic acid at a level of at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95% by weight of the total fatty acid content of the seeds. In some embodiments that may be combined with any of the preceding embodiments, the seeds include oleic acid at a level between 68-72%, between 70-76%, between 72-80%, between 74-80%, between 74-82%, between 76-82%, between 78-82%, between 80-84%, between 82-88%, between 82-89%, between 84-90%, or between 86-90% by weight of the total fatty acid content of the seeds. In some embodiments that may be combined with any of the preceding embodiments, the plant produces seeds and the seeds include linoleic acid at a level of less than 18%, less than 16%, less than 15%, less than 14%, less than 13%, less than 12%, less than 10%, less than 9%, less than 8%, less than 7%, less than 6%, less than 5%, less than 4%, less than 3%, or less than 2% by weight of the total fatty acid content of the seeds. In some embodiments that may be combined with any of the preceding embodiments, the plant produces seeds and the seeds include oleic acid at a level of at least 68%, at least 70%, at least 72%, at least 74%, at least 76%, at least 78%, at least 79%, at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95% by weight of the total fatty acid content of the seeds; and the seeds include linoleic acid at a level of less than 18%, less than 16%, less than 15%, less than 14%, less than 13%, less than 12%, less than 10%, less than 9%, less than 8%, less than 7%, less than 6%, less than 5%, less than 4%, less than 3%, or less than 2% by weight of the total fatty acid content of the seeds. In some embodiments that may be combined with any of the preceding embodiments, the plant is selected from the group of *Brassica napus, Brassica rapa, Brassica oleracea, Brassica juncea, Brassica species, Raphanus sativus, Pisum sativum, Phaseolus vulgaris, Lens culinaris, Glycine max*, or *Fabaceae* species. In some embodiments, the plant is *Brassica napus, Brassica rapa*, or *Brassica juncea*.

In another aspect, the present disclosure provides an $F_1$ plant, where the $F_1$ plant has the plant of any one of the preceding embodiments as a parent. In another aspect, the present disclosure provides a method of making plant seeds, the method including crossing the plant of any one of the preceding embodiments with another plant and harvesting seed therefrom. In another aspect, the present disclosure provides a method of making a plant of any one of the preceding embodiments, the method including selecting seeds from the cross of the plant of any one of the preceding embodiments with the plant of any one of the preceding embodiments to make the plant of any one of the preceding embodiments. In another aspect, the present disclosure provides a plant produced by growing the seed of any one of the preceding embodiments, where the plant has all the physiological and morphological characteristics of the plant of any one of the preceding embodiments.

In another aspect, the present disclosure provides oil extracted from seeds including oleic acid at a level of at least 80% by weight of the total fatty acid content of the seeds. In some embodiments, the oil is extracted from seeds including oleic acid at about 80-84%, 82-88%, 82-89%, 84-90%, or 86-90% or greater by weight of the total fatty acid content of the seeds.

In another aspect, the present disclosure provides oil extracted from seeds of plants including at least one mutation in at least one, at least two, at least three, or four nucleic acid sequences encoding fatty acid desaturase 2 (FAD2) genes, wherein the nucleic acid sequences have at least 90% identity, at least 95% sequence identity, at least 98% sequence identity, or at least 99% sequence identity to nucleic acid sequences selected from the group of SEQ ID NO: 1, SEQ ID NO: 2, SEQ ID NO: 3, or SEQ ID NO: 4, wherein the mutation reduces or eliminates expression of the FAD2 gene and/or FAD2 polypeptide, and wherein the plant produces seeds and the seeds include oleic acid at a level of at least 80% by weight of the total fatty acid content of the seeds. In some embodiments, the seeds include oleic acid at about 80-84%, 82-88%, 82-89%, 84-90%, or 86-90% or greater by weight of the total fatty acid content of the seeds. In some embodiments that may be combined with any of the preceding embodiments, the plant is selected from the group of *Brassica napus, Brassica rapa, Brassica oleracea, Brassica juncea, Brassica species, Raphanus sativus, Pisum sativum, Phaseolus vulgaris, Lens culinaris, Glycine max*, or *Fabaceae* species. In some embodiments, the plant is *Brassica napus, Brassica rapa*, or *Brassica juncea*.

In another aspect, the present disclosure relates to a method of producing the plant or part thereof of any of the preceding embodiments, including the steps of a) introducing mutations into plant cells, wherein the mutations are at least one mutation in at least one, at least two, at least three, or four nucleic acid sequences encoding FAD2 genes; b) selecting or identifying plant cells containing the mutations; and c) regenerating a plant having the mutations; wherein the plant produces seed oil comprising a high oleic acid content. In a further aspect, the present disclosure relates to a method of producing the plant or part thereof of any of the preceding embodiments, including the steps of a) introducing mutations into plant cells, wherein the mutations are at least one mutation in at least one, at least two, at least three, or four nucleic acid sequences encoding FAD2 genes; b) selecting or identifying plant cells containing the mutations; and c) regenerating a plant having the mutations; wherein the plant produces seeds and the seeds include a high oleic acid content. In some embodiments that may be combined with any of the preceding embodiments, the high oleic acid content includes an oleic acid content of at least 68%, at least 70%, at least 72%, at least 74%, at least 76%, at least 78%, at least 79%, at least 80%, at least 81%, at least 82%, at least 83%, at least 84%, at least 84%, at least 85%, at least 86%, at least 87%, at least 88%, at least 89%, at least 90%, at least 91%, at least 92%, at least 93%, at least 94%, or at least 95%. In some embodiments that may be combined with any of the preceding embodiments, the plant produces seed oil including a low linoleic acid content. In some embodiments, the low linoleic acid content includes a linoleic acid content of less than 18%, less than 16%, less than 15%, less than 14%, less than 13%, less than 12%, less than 10%, less than 9%, less than 8%, less than 7%, less than 6%, less than 5%, less than 4%, less than 3%, or less than 2%. In some embodiments that may be combined with any of the preceding embodiments, the mutations are introduced using one or more vectors, wherein the vectors include gene editing components selected from the group of a CRISPR/Cas9 system, a TALEN, a zinc finger, and a meganuclease designed to target a nucleic acid sequence encoding a FAD2 gene. In some embodiments, the mutations are introduced using a GRON system designed to target a nucleic acid sequence encoding a FAD2 gene. In some embodiments, the GRON system comprises one or more modifications selected from the group consisting of a Cy3 group, 3PS group, and a 2'O-methyl group. In some embodiments that may be combined with any of the preceding embodiments, the nucleic acid sequences have at least 90% sequence identity, at least 95% sequence identity, at least 98% sequence identity, or at least 99% sequence identity to nucleic acid sequences selected from the group of SEQ ID NO: 1, SEQ ID NO: 2, SEQ ID NO: 3, or SEQ ID NO: 4. In some embodiments, the nucleic acid sequences are selected from the group of SEQ ID NO: 1, SEQ ID NO: 2, SEQ ID NO: 3, or SEQ ID NO: 4. In some embodiments that may be combined with any of the preceding embodiments, the mutation is selected from the group of a frameshift mutation, a frameshift mutation resulting in one or more nucleotide insertions or deletions as compared to the corresponding endogenous gene without the frameshift mutation, and a frameshift mutation resulting in a premature stop codon, and wherein the mutation reduces or eliminates expression of the FAD2 gene and/or FAD2 polypeptide.

In another aspect, the present disclosure relates to a method of producing high oleic acid in a seed, the method including growing a plant including at least one mutation in at least one, at least two, at least three, or four nucleic acid sequences encoding FAD2 genes, wherein the mutation reduces or eliminates expression of the FAD2 gene and/or FAD2 polypeptide, and wherein said plant produces seed oil including oleic acid at a level of at least 80%. In a further aspect, the present disclosure relates to a method of producing high oleic acid in a seed, the method including growing a plant including at least one mutation in at least one, at least two, at least three, or four nucleic acid sequences encoding FAD2 genes, wherein the mutation reduces or eliminates expression of the FAD2 gene and/or FAD2 polypeptide, and wherein said plant produces seeds and said seeds include oleic acid at a level of at least 80% by weight of the total fatty acid content of said seeds. In some embodiments that may be combined with any of the preceding embodiments, the nucleic acid sequences have at least 90% sequence identity, at least 95% sequence identity, at least 98% sequence identity, or at least 99% sequence identity to nucleic acid sequences selected from the group of SEQ ID NO: 1, SEQ ID NO: 2, SEQ ID NO: 3, or SEQ ID NO: 4. In some embodiments, the nucleic acid sequences are selected from the group of SEQ ID NO: 1, SEQ ID NO: 2, SEQ ID NO: 3, or SEQ ID NO: 4. In some embodiments that may be combined with any of the preceding embodiments, the method further includes isolating seeds from the plant. In some embodiments, the method further includes extracting oil from the plant seeds. In some embodiments that may be combined with any of the preceding embodiments, the plant is selected from the group of *Brassica napus, Brassica rapa, Brassica oleracea, Brassica juncea, Brassica species, Raphanus sativus, Pisum sativum, Phaseolus vulgaris, Lens culinaris, Glycine max*, and *Fabaceae* species. In some embodiments, the plant is *Brassica napus, Brassica rapa*, or *Brassica juncea*.

BRIEF DESCRIPTION OF THE DRAWINGS

FIG. 1A illustrates the oleic acid % vs. the Oxidative Stability Index (OSI) of these oils. FIG. 1B illustrates the total polyunsaturated fatty acid (PUFA) % vs. OSI of these oils. For FIGS. 1A-1B, each oil is represented by a dot, the dot for CIBUS line #1 canola oil is a red dot that is indicated by a label, and the trend lines for the ratios across the oils are shown as a dotted line.

DETAILED DESCRIPTION

Figure 1A:
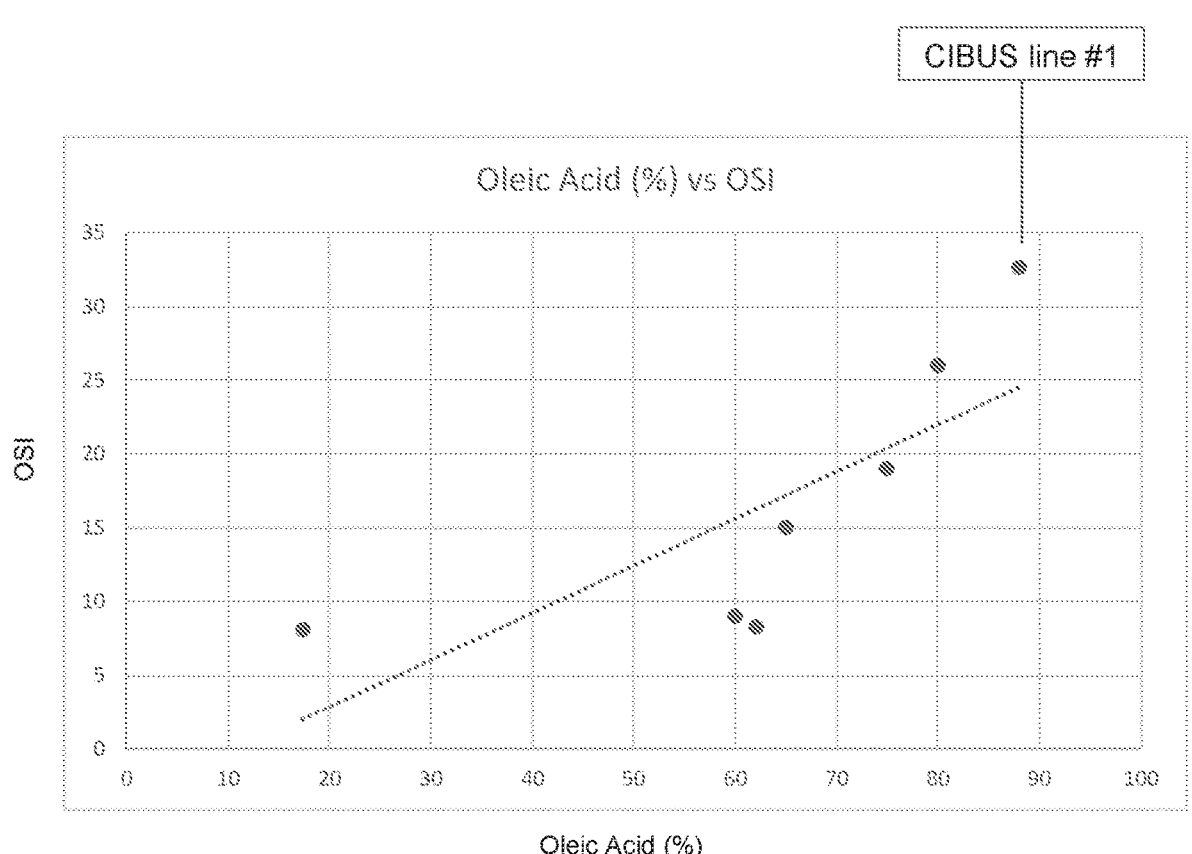
FIGS. 1A-1B illustrate the data and trend lines for oils with different fatty acid compositions (see Table 7).

In various aspects and embodiments of the present disclosure, provided include a plant or plant cell having one or more FAD2 mutations and/or mutation combinations, methods of making such a plant or plant cell, and methods for producing plants having desirable seed oil compositions.

It will be readily apparent to a person skilled in the art that varying substitutions and modifications may be made to the disclosure disclosed herein without departing from the scope and spirit of the disclosure.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Thus, it should be understood that although the present disclosure has been specifically disclosed by preferred embodiments and optional features, modification, improvement, and variation of the disclosures disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

High Oleic Canola Oil

In various aspects and embodiments, provided herein include *Brassica napus* plants for the production of seed oils with high levels of oleic acid ($18:1\Delta9^{cis}$). In some embodiments Rapid Trait Development System (RTDS™) technologies are used for the alteration or disruption of one or more genes or alleles encoding the oleate desaturase (FAD2 locus) that is responsible for the addition of an unsaturated or double bond at the $\Delta12$ position of oleoyl CoA resulting in the production of linoleic acid ($18:2\Delta9^{cis}$, $12^{cis}$). Plants with these modifications in some embodiments have an increased amount of oleic acid ($18:1\Delta9^{cis}$) and decreased amounts of either or both linoleic acid ($18:2\Delta9,12$) and linolenic acid ($18:3\Delta9,12,15$) in the seed oil. The resulting oils may be important items of commerce principally in the food and specialty chemicals markets. The resulting seed oils might have oleic acid contents ranging from 65% to greater than 90% oleic acid in the form of mixed triglycerides. The increase of oleic acid content is often concomitant with a decrease in polyunsaturated fatty acids (18:2 and/or 18:3) and will therefore have higher oxidative stability. Where the FAD2 gene modifications are achieved using RTDS™, the seed and products from the seed including oil, fatty acids, and meal may be considered non-transgenic and non-GMO.

Canola oil generally contains about 60% oleic acid, as well as about 21% linoleic acid and 9-11% linolenic acid in the form of mixed triglycerides. As currently constituted, canola oil is promoted as a healthy oil, low in saturated fatty acids, yet stable enough for general use as a cooking oil. However, an oil with significantly increased levels of oleic acid and decreased levels of linoleic and linolenic acid may have increased value in both food and commodity chemicals markets.

In the food market, a moderate increase of oleic acid, to the range of 70-80%, would place canola oil in competition with RBD (refined, bleached, deodorized) olive oil and mid-oleic sunflower oils. This oil could have increased value for both a salad oil and a frying oil, with increased oxidative stability leading to lower rancidity, longer storage life and less browning at high temperature. This is critical since frying oils are often partially hydrogenated to increase high temperature stability. Canola oil with increased oleic acid and decreased linoleic and linolenic acids would obviate the need for hydrogenation, thus avoiding the generation of trans fatty acids that are a recognized public health hazard.

Canola oil with levels of oleic acid above 80% has applications, for example, in the industrial oleochemical market. Currently, technical grade oleic acid is available at about 75% oleic acid, and the impurities (linoleic and linolenic acid) compromise the product for use in making predictable, high purity chemical modifications for a very broad range of chemical intermediates and finished products. In addition, while canola oil makes an important biodiesel fuel feedstock, the presence of linoleic and linolenic compromise both storage stability and result in higher than desirable NOx production. Canola oil in the range of 80-90% oleic acid with low linoleic and linolenic would offer added value to both industrial chemical use and for clean, improved heat and cold stable biodiesel fuels.

Canola oil with oleic acid levels greater than or equal to 90% would allow the use of the triglycerides and fatty acids for chemical modifications that require high purity feedstocks, such as metathesis and direct polymerization of triolein triglycerides to produce high performance foam padding for automobiles and furniture markets. At greater than 90% oleic acid, canola oil could be a replacement for distilled grades of oleic acid, which currently carry a value many times that of the technical grades that are the primary material of commerce.

Plants of the present disclosure that produce seed oil with a high oleic acid content may produce seed oil with, for example, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% oleic acid. In some embodiments, seed oil with a high oleic acid content may have an oleic acid content of between about 68-72%, between about 70-76%, between about 72-80%, between about 74-80%, between about 74-82%, between about 76-82%, between about 78-82%, between about 80-84%, between about 82-88%, between about 82-89%, between about 84-90%, or between about 86-90%. Plants of the present disclosure that produce seed oil with a high oleic acid content and low linoleic acid content may produce seed oil with, for example, at most about 20%, at most about 19%, at most about 18%, at most about 17%, at most about 16%, at most about 15%, at most about 14%, at most about 13%, at most about 12%, at most about 11%, at most about 10%, at most about 9%, at most about 8%, at most about 7%, at most about 6%, at most about 5%, at most about 4%, at most about 3%, at most about 2%, at most about 1%, or at most about 0% linoleic acid. In some embodiments, seed oil with a high oleic acid content and a low linoleic acid content may have an oleic acid content of at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100%; and a linoleic acid content of at most about 20%, at most about 19%, at most about 18%, at most about 17%, at most about 16%, at most about 15%, at most about 14%, at most about 13%, at most about 12%, at most about 11%, at most about 10%, at most about 9%, at most about 8%, at most about 7%, at most about 6%, at most about 5%, at most about 4%, at most about 3%, at most about 2%, at most about 1%, or at most about 0%.

Oil of the present disclosure may be extracted from seeds including oleic acid at a level of at least 80% by weight of the total fatty acid content of the seeds. In some embodiments, the oil is extracted from seeds including oleic acid at about 80-84%, 82-88%, 82-89%, 84-90%, or 86-90% or greater by weight of the total fatty acid content of the seeds. Oil of the present disclosure may be extracted from seeds of plants including at least one mutation in at least two, at least three, or four nucleic acid sequences encoding fatty acid desaturase 2 (FAD2) genes, wherein the nucleic acid sequences have at least 90% identity, at least 95% sequence identity, at least 98% sequence identity, or at least 99% sequence identity to nucleic acid sequences selected from the group of SEQ ID NO: 1, SEQ ID NO: 2, SEQ ID NO: 3, or SEQ ID NO: 4, wherein the mutation reduces or eliminates expression of the FAD2 gene and/or FAD2 poly-peptide, and wherein the plant produces seeds and the seeds include oleic acid at a level of at least 80% by weight of the total fatty acid content of the seeds. In some embodiments, the seeds include oleic acid at about 80-84%, 82-88%, 82-89%, 84-90%, or 86-90% or greater by weight of the total fatty acid content of the seeds. In some embodiments. In some embodiments, oil of the present disclosure has a lower level of C18:2 (18:2; omega-6 type) than C18:3 (18:3; omega-3 type) fatty acids. In some embodiments, oil of the present disclosure contains C18:2 levels of about 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0%; and C18:3 levels of about 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, or 5.2%. In some embodiments, oil of the present disclosure contains C18:2 levels of about 2.6% and C18:3 levels of about 4.1%. In some embodiments, oil of the present disclosure contains C18:2 levels of about 2% and C18:3 levels of about 3%. In some embodiments, the oil of the present disclosure has a ratio of omega-6 to omega-3 that is less than 1. In some embodiments, the oil of the present disclosure has a ratio of omega-6 to omega-3 that is about 0.60, 0.61, 0.62, 0.63, 0.64, 0.65, 0.66, 0.67, 0.68, 0.69, or 0.70.

Some aspects of the present disclosure relate to a nutri-tional product containing the oil of the present disclosure including an oleic acid content of at least 70%. In some embodiments, the nutritional product is selected from the group consisting of prepared meal, snack food, dietary supplement, dietary substitute, cooking oil, salad oil, or frying oil. In some embodiments, the oil of the present disclosure is used as a blending oil stock to lower the omega-6 to omega-3 ratio for nutritional product formula-tions using commercial oils with high omega-6 to omega-3 ratios (e.g., with an omega-6 to omega-3 ratio of 8.5; see Table 7). In some embodiments, the oil of the present disclosure is used as an oil stock to produce nutritional product formulations with lower omega-6 to omega-3 ratios. In some embodiments, the oil of the present disclosure is used to reduce the risk of chronic disease (see, e.g., Simo-polous, Biomed. Pharmacother., 56(8):365-379, 2002).

Some aspects of the present disclosure relate to a com-modity chemical (e.g., industrial chemical product) contain-ing the oil of the present disclosure including an oleic acid content of at least 80%. In some embodiments, the oil of the present disclosure is used for making predictable, high purity chemical modifications that produce a range of indus-trial chemical intermediates and finished products. In some embodiments, the oil of the present disclosure is used as a biodiesel fuel feedstock. In some embodiments, the oil of the present disclosure is used as a biodiesel fuel feedstock that results in low NOx production.

Some aspects of the present disclosure relate to a high purity feedstock containing the oil of the present disclosure including an oleic acid content of at least 90%. In some embodiments, the high purity feedstock is used for chemical modifications. In some embodiments, the chemical modifi-cations are metathesis and direct polymerization of triolein triglycerides. In some embodiments, the chemical modifi-cations result in high performance foam padding that is used in automobiles or furniture.

Some aspects of the present disclosure relate to a high-value distilled grade of oleic acid containing the oil of the present disclosure including an oleic acid content of at least 91%.

Fatty Acid Desaturase 2 (FAD2) Genes

The present disclosure generally relates to plants having mutations in fatty acid desaturase 2 (FAD2) genes. In some embodiments, one or more mutations in two or more FAD2 genes results in the production of seed oil with a high oleic acid content. In some embodiments, the seed oil further has a low linoleic acid content.

In some aspects, plants of the present disclosure are *Brassica napus* (e.g., *Brassica napus* L. spp. *oleifera*), *Brassica rapa*, or *Brassica juncea* plants, also known as canola. Canola plants contain four fatty acid desaturase 2 (FAD2) genes, designated BnFAD2-1, BnFAD2-2, BnFAD2-3, and BnFAD2-4. In some aspects, plants of the present disclosure have at least one mutation in at least two FAD2 genes. In some embodiments, plants of the present disclosure do not have a mutation in BnFAD2-3.

Certain aspects of the present disclosure relate to BnFAD2-1. The nucleotide coding sequence of BnFAD2-1 is set forth in SEQ ID NO: 1. Provided herein are also homologs and orthologs of BnFAD2-1. In some embodiments, a homolog or ortholog of BnFAD2-1 has a nucleic acid coding sequence that is at least 50%, at least 55%, at least 60%, at least 65%, at least 70%, at least 75% at least 80%, at least 85%, at least 90%, at least 91%, at least 92%, at least 93%, at least 94%, at least 95%, at least 96%, at least 97%, at least 98%, or at least 99% identical to SEQ ID NO: 1. In some embodiments, a nucleic acid sequence encoding a homolog or ortholog of BnFAD2-1 may also have one or more mutations.

Certain aspects of the present disclosure relate to BnFAD2-2. The nucleotide coding sequence of BnFAD2-2 is set forth in SEQ ID NO: 2. Provided herein are also homologs and orthologs of BnFAD2-2. In some embodiments, a homolog or ortholog of BnFAD2-2 has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2. In some embodiments, a nucleic acid sequence encoding a homolog or ortholog of BnFAD2-2 may also have one or more mutations.

Certain aspects of the present disclosure relate to BnFAD2-3. The nucleotide coding sequence of BnFAD2-3 is set forth in SEQ ID NO: 3. Provided herein are also homologs and orthologs of BnFAD2-3. In some embodiments, a homolog or ortholog of BnFAD2-3 has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3. In some embodiments, a nucleic acid sequence encoding a homolog or ortholog of BnFAD2-3 may also have one or more mutations.

Certain aspects of the present disclosure relate to BnFAD2-4. The nucleotide coding sequence of BnFAD2-4 is set forth in SEQ ID NO: 4. Provided herein are also homologs and orthologs of BnFAD2-4. In some embodiments, a homolog or ortholog of BnFAD2-4 has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 4. In some embodiments, a nucleic acid sequence encoding a homolog or ortholog of BnFAD2-4 may also have one or more mutations.

In some aspects, plants of the present disclosure have a mutation in BnFAD2-1. In some embodiments, these plants may also have mutations in one or more FAD2 genes selected from BnFAD2-2, BnFAD2-3, and BnFAD2-4. In some embodiments, these plants may also have mutations in one or more FAD2 genes selected from BnFAD2-2 and BnFAD2-4.

In some aspects, plants of the present disclosure have a mutation in BnFAD2-2. In some embodiments, these plants may also have mutations in one or more FAD2 genes selected from BnFAD2-1, BnFAD2-3, and BnFAD2-4. In some embodiments, these plants may also have mutations in one or more FAD2 genes selected from BnFAD2-1 and BnFAD2-4.

In some aspects, plants of the present disclosure have a mutation in BnFAD2-3. In some embodiments, these plants may also have mutations in one or more FAD2 genes selected from BnFAD2-1, BnFAD2-2, and BnFAD2-4.

In some aspects, plants of the present disclosure have a mutation in BnFAD2-4. In some embodiments, these plants may also have mutations in one or more FAD2 genes selected from BnFAD2-1, BnFAD2-2, and BnFAD2-3. In some embodiments, these plants may also have mutations in one or more FAD2 genes selected from BnFAD2-1 and BnFAD2-2.

In some aspects, plants of the present disclosure do not have a mutation in BnFAD2-3. In some embodiments, these plants may have mutations in one or more FAD2 genes selected from BnFAD2-1, BnFAD2-2, and BnFAD2-4.

In some aspects, plants of the present disclosure have a mutation in at least one, at least two, at least three, or four of the FAD2 genes. In some aspects, plants of the present disclosure have a mutation in at least two, at least three, or four of the FAD2 genes.

In some aspects, the mutation may be a frameshift mutation, a frameshift mutation resulting in one or more nucleotide insertions or deletions as compared to the corresponding endogenous gene without the frameshift mutation, or a frameshift mutation resulting in a premature stop codon, wherein the mutation reduces or eliminates expression of the FAD2 gene and/or FAD2 polypeptide.

A modified nucleic acid of the present disclosure (e.g., a mutated FAD2 gene) in a plant cell may have its expression reduced by at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% as compared to a corresponding control. Various controls will be readily apparent to one of skill in the art. For example, a control may be a corresponding plant or plant cell that does not contain a mutated nucleic acid encoding a FAD2 polypeptide of the present disclosure.

A modified polypeptide of the present disclosure (e.g., a modified FAD2 polypeptide having reduced activity) in a plant cell may have its expression or activity reduced by at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% as compared to a corresponding control. Various controls will be readily apparent to one of skill in the art. For example, a control may be a corresponding plant or plant cell that does not contain a modified FAD2 polypeptide of the present disclosure.

Methods of Identifying Sequence Similarity

Two polynucleotides or polypeptides are identical if the sequence of nucleotides or amino acid residues, respectively, in the two sequences is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. For polypeptides where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4: 11-17 (1988) e.g., as implemented in the program PC/GENE (Intelligenetics, Mountain View, Calif., USA).

The phrases "substantially identical," and "percent identity" in the context of two nucleic acids or polypeptides, refer to sequences or subsequences that have at least 50%, advantageously 60%, preferably 70%, more preferably 80%, and most preferably 90-95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides displays significant variation. Therefore, a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence relative to the reference sequence, based on the designated program parameters.

The percentage of "sequence similarity" is the percentage of amino acids or nucleotides which is either identical or changed viz. "sequence similarity"=percent sequence identity)+percent changes). Thus, whenever the term sequence "similarity" is used it embraces sequence "identity" and "changes" to the sequence at some percentage. In certain embodiments, the changes in a sequence permitted by the referenced percent sequence identity are all or nearly all conservative changes; that is, in those embodiments when a sequence is 90% identical, the remaining 10% are all or nearly all conservative changes. The term "nearly all" in this context refers to at least 75% of the permitted sequence changes are conservative changes, more preferably at least 85%, still more preferably at least 90%, and most preferably at least 95%.

Optimal alignment of sequences for comparison can be conducted, e.g., by the local homology algorithm of Smith & Waterman, 0.4dv. Appl. Math. 2:482 (I 98 I), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by software for alignments such as VECTOR NTI Version #11.5 by Life Technologies, Carlsbad, Calif., USA, by the procedures described in ClustalW, Thompson, J. D., Higgins, D. G. and Gibson, T. J. (1994) CLUSTALW: improving the sensitivity of progressive multiple sequence alignment through sequence weighting, position—specific gap penalties and weight matrix choice. Nucleic Acids Research, 22:4673-4680 or by visual inspection (see generally, Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 33 89-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)). In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleic Acids and Delivery Thereof to Cells

Certain aspects of the present disclosure involve nucleic acids (e.g. FAD2 genes), as well as nucleic acids having one or more mutations. Various methods exist for inducing mutations in a nucleic acid, as described herein. In some embodiments, one or more nucleic acids may be delivered to a cell, as described herein.

Oligonucleobases

As used herein, an "oligonucleobase" is a polymer of nucleobases, which polymer can hybridize by Watson-Crick base pairing to a DNA having the complementary sequence.

Nucleobases comprise a base, which may be a purine, pyrimidine, or a derivative or analog thereof. Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides.

An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When an oligonucleobase strand is coextensive with a chain, the 3' and 5' ends of the strand are also 3' and 5' termini of the chain.

The oligonucleobase can be introduced into a plant cell using any method commonly used in the art, including but not limited to, microcarriers (biolistic delivery), microfibers (whiskers), electroporation, nucleofection, PEG-mediated delivery, direct DNA uptake and microinjection. Illustrative examples of a oligonucleobase are described below.

The description can be practiced with oligonucleobases having the conformations and chemistries described in the Kmiec I and Kmiec II patents which are incorporated herein by reference. Kmiec I discloses a method for introducing specific genetic alterations into a target gene. The oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; WO 99/40789; U.S. Pat. No. 6,870,075; and US Published Patent Application 20030084473, which are each hereby incorporated in their entirety, disclose additional molecules that can be used for the present description. The term "oligonucleobase" is used herein to denote the molecules that can be used in the methods of the present disclosure and include mixed duplex oligonucleotides, non-nucleotide containing molecules taught in Kmiec II, single stranded oligodeoxynucleotides and other molecules taught in the above noted patents and patent publications.

In one embodiment, the oligonucleobase is a mixed duplex oligonucleotide in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are incorporated herein by reference. As used herein, a 2'-fluoro, chloro or bromo derivative of a ribonucleotide or a ribonucleotide having a 2'-OH substituted with a substituent described in the Martin Applications or Sproat is termed a "2'-substituted ribonucleotide." As used herein the term "RNA-type nucleotide" means a 2'-hydroxyl or 2'-substituted nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

In one embodiment of the present disclosure, the oligonucleobase or GRON is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-substituted nucleotide. Particularly preferred embodiments of 2'-substituted ribonucleotides are 2'-fluoro, 2'-methoxy, 2'-propyloxy, 2'-allyloxy, 2'-hydroxylethyloxy, 2'-methoxy, ethyloxy, 2'-fluoropropyloxy and 2'-trifluoropropyloxy substituted ribonucleotides. More preferred embodiments of 2'-substituted ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotide having only a single type of 2'-substituted RNA-type nucleotide are more conveniently synthesized, the methods of the disclosure can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target FAD2 gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

The change to be introduced into the target gene is encoded by the heterologous region. The change to be introduced into the FAD2 gene may be a change in one or more bases of the target gene sequence that changes the native amino acid in that position to the desired amino acid.

In another embodiment of the present disclosure, the oligonucleobase is a single stranded oligodeoxynucleotide mutational vector or SSOMV, which is disclosed in International Patent Application PCT/US00/23457, which is incorporated herein by reference in its entirety. The sequence of the SSOMV is based on the same principles as the mutational vectors described in U.S. Pat. Nos. 5,756, 325; 5,871,984; 5,760,012; 5,888,983; 5,795,972; 5,780, 296; 5,945,339; 6,004,804; and 6,010,907 and in International Publication Nos. WO 98/49350; WO 99/07865; WO 99/58723; WO 99/58702; WO 99/40789; U.S. Pat. No. 6,870,075; and US Published Patent Application 20030084473. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region will cause a substitution.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotides be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling VA (acquired by Maravai LifeSciences), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is the most preferred. When the indocarbocyanine is N-oxyalkyl substituted it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings.

Without limitation as to theory these substitutions prevent the dye from being an intercalating dye. The identity of the substituents at these positions is not critical. The SSOMV can in addition have a 3' blocking substituent. Again the chemistry of the 3' blocking substituent is not critical.

In another embodiment the oligonucleotide may be a single-stranded oligodeoxynucleotide having a 3' end nucleotide, a 5' end nucleotide, having at least 25 deoxynucleotides and not more than 65 deoxynucleotides, and having a sequence comprising at least two regions each of at least 8 deoxynucleotides that are each, respectively, identical to at least two regions of the targeted chromosomal gene, which regions together are at least 24 nucleotides in length, and which regions are separated by at least one nucleotide in the sequence of the targeted chromosomal gene or in the sequence of the oligodeoxynucleotide or both such that the sequence of the oligodeoxynucleotide is not identical to the sequence of the targeted chromosomal gene. See U.S. Pat. No. 6,271,360 which is incorporated herein by reference.

The mutations herein described might also be obtained by mutagenesis (random, somatic or directed) and other DNA editing or nucleases using a repair template including, but not limited to, gene targeting using zinc finger nucleases, using Transcription Activator-Like Effector Nucleases (TALENs), using Clustered Regularly Interspaced Short Palindromic Repeats (CRISPRs). These nucleases can be plasmid (DNA) based, RNA and/or protein.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204, 253 describe general techniques for selecting microcarriers and devices for projecting them. U.S. Pat. Nos. 5,484,956 and 5,489,520 describe the preparation of fertile transgenic corn using microprojectile bombardment of corn callus tissue. The biolistic techniques are also used in transforming immature corn embryos.

Specific conditions for using microcarriers in the methods of the present disclosure are described in International Publication WO 99/07865. In an illustrative technique, ice cold microcarriers (60 mg/ml), mixed duplex oligonucleotide (60 mg/ml) 2.5 M $CaCl_2$ and 0.1 M spermidine are added in that order; the mixture is gently agitated, e.g., by vortexing, for 10 minutes and let stand at room temperature for 10 minutes, whereupon the microcarriers are diluted in 5 volumes of ethanol, centrifuged and resuspended in 100% ethanol. Good results can be obtained with a concentration in the adhering solution of 8-10 µg/µl microcarriers, 14-17 µg/ml mixed duplex oligonucleotide, 1.1-1.4 M $CaCl_2$ and 18-22 mM spermidine. Optimal results were observed under the conditions of 8 µg/µl microcarriers, 16.5 µg/ml mixed duplex oligonucleotide, 1.3 M $CaCl_2$ and 21 mM spermidine.

Oligonucleobases can also be introduced into plant cells for the practice of the present disclosure using microfibers to penetrate the cell wall and cell membrane. U.S. Pat. No. 5,302,523 to Coffee et al. describes the use of 30×0.5 µm and 10×0.3 µm silicon carbide fibers to facilitate transformation of suspension maize cultures of Black Mexican Sweet. Any mechanical technique that can be used to introduce DNA for transformation of a plant cell using microfibers can be used to deliver oligonucleobases for use in making the present FAD2 mutants. The process disclosed by Coffee et al. in U.S. Pat. No. 5,302,523 can be employed with regenerable plant cell materials to introduce the present oligonucleobases to effect the mutation of the FAD2 gene.

An illustrative technique for microfiber delivery of an oligonucleobase is as follows: Sterile microfibers (2 µg) are suspended in 150 µl of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 hours as is appropriate for the particular trait.

Electroporation

In an alternative embodiment, the oligonucleobases can be delivered to the plant cell by electroporation of a protoplast derived from a plant part according to techniques that are well-known to one of ordinary skill in the art. See, e.g., Gallois et al., 1996, in Methods in Molecular Biology 55:89-107, Humana Press, Totowa, N.J.; Kipp et al., 1999, in Methods in Molecular Biology 133:213-221, Humana Press, Totowa, N.J.

Oligonucleobases can also be introduced into microspores by electroporation. Upon release of the tetrad, the microspore is uninucleate and thin-walled. It begins to enlarge and develops a germpore before the exine forms. A microspore at this stage is potentially more amenable to transformation with exogenous DNA than other plant cells. In addition, microspore development can be altered in vitro to produce either haploid embryos or embryogenic callus that can be regenerated into plants (Coumans et al., Plant Cell Rep. 7:618-621, 1989; Dana et al., Plant Sci. 67:83-88, 1990; Maheshwari et al., Am. J Bot. 69:865-879, 1982; Schaeffer, Adv. In Cell Culture 7:161-182, 1989; Swanson et al., Plant Cell Rep. 6:94-97, 1987). Thus, transformed microspores can be regenerated directly into haploid plants or dihaploid fertile plants upon chromosome doubling by standard methods. See also co-pending application U.S. Ser. No. 09/680,858 entitled Compositions and Methods for Plant Genetic Modification which is incorporated herein by reference.

Microspore electroporation can be practiced with any plant species for which microspore culture is possible, including but not limited to plants in the families Graminae, Leguminoceae, Cruciferaceae, Solanaceac, Cucurbitaceae, Rosaccae, Poaceae, Lilaceae, Rutaceae, Vitaceae, including such species as corn (*Zea mays*), wheat (*Triticum aestivum*), rice (*Oryza sativa*), oats, barley, canola (*Brassica napus, Brassica rapa, Brassica oleracea*, and *Brassica juncea*), cotton (*Gossypium hirsuitum* L.), various legume species (e.g., soybean (*Glycine max*), pea (*Pisum sativum*), etc.), grapes (*Vitis vinifera*), and a host of other important crop plants. Microspore embryogenesis, both from anther and microspore culture, has been described in more than 170 species, belonging to 68 genera and 28 families of dicotyledons and monocotyledons (Raghavan, Embryogenesis in Agniosperms: A Developmental and Experimental Study, Cambridge University Press, Cambridge, England, 1986; Rhagavan, Cell Differentiation 21:213-226, 1987; Raemakers et al., Euphytica 81:93-107, 1995). For a detailed discussion of microspore isolation, culture, and regeneration of double haploid plants from microspore-derived embryos (MDE) in *Brassica napus* L., see Nehlin, The Use of Rapeseed (*Brassica napus* L.) Microspores as a Tool for Biotechnological Applications, doctoral thesis, Swedish University of Agricultural Sciences, Uppsala, Sweden, 1999; also Nehlin et al., Plant Sci. 111:219-227, 1995, and Nehlin et al., Plant Sci. 111:219-227, 1995). Chromosome doubling from microspore or anther culture is a wellestablished technique for production of double-haploid homozygous plant lines in several crops (Heberle-Bors et al., In vitro pollen cultures: Progress and perspectives. In: Pollen Biotechnology. Gene expression and allergen characterization, vol. 85-109, ed. Mohapatra, S. S., and Knox, R. B., Chapman and Hall, New York, 1996).

Microspore electroporation methods are described in Jardinaud et al., Plant Sci. 93:177-184, 1993, and Fennell and Hauptman, Plant Cell Reports 11:567-570, 1992. Methods for electroporation of MDON into plant protoplasts can also be adapted for use in microspore electroporation.

Whiskers Technique

In yet another alternative embodiment, the oligonucleobase can be delivered to the plant cell by whiskers or microinjection of the plant cell. The so called whiskers technique is performed essentially as described in Frame et al., 1994, Plant J. 6:941-948. The oligonucleobase is added to the whiskers and used to transform the plant cells. The oligonucleobase may be co-incubated with plasmids comprising sequences encoding proteins capable of forming recombinase complexes in plant cells such that recombination is catalyzed between the oligonucleotide and the target sequence in the FAD2 gene.

Other Delivery Methods

In an alternative embodiment, nucleic acids are embedded in microbeads composed of calcium alginate and taken up by plant protoplasts in the presence of the membrane-modifying agent polyethylene glycol (see, e.g., Sone et al., 2002; Liu et al., 2004).

In an alternative embodiment, nucleic acids frozen in water and introduced into plant cells by bombardment in the form of microparticles (see, e.g., Gilmore, 1991, U.S. Pat. No. 5,219,746; Brinegar et al.).

In an alternative embodiment, nucleic acids attached to nanoparticles are introduced into intact plant cells by incubation of the cells in a suspension containing the nanoparticle (see, e.g., Pasupathy et al., 2008) or by delivering them into intact cells through particle bombardment or into protoplasts by co-incubation (see, e.g., Torney et al., 2007).

In an alternative embodiment, nucleic acids complexed with penetrating peptides are delivered into cells by co-incubation (see, e.g., Chugh et al., 2008, WO 2008148223 A1; Eudes and Chugh).

In an alternative embodiment, nucleic acids are introduced into intact cells through electroporation (see, e.g., He et al., 1998, U.S. 2003/0115641 A1, Dobres et al.).

In an alternative embodiment, nucleic acids are delivered into cells of dry embryos by soaking them in a solution with nucleic acids (by soaking dry embryos in (see, e.g., Topfer et al., 1989, Senaratna et al., 1991).

Targeted Gene Modification

Targeted genetic modification mediated by oligonucleotides is a valuable technique for use in the specific alteration of short stretches of DNA to create or make deletions, short insertions, and point mutations and may be used in conjunction with the disclosures herein, for example to cause one or more of the FAD2 mutations contemplated herein. These methods may in some embodiments involve DNA pairing/annealing, followed by a DNA repair event. First, the nucleic acid anneals with its complementary strand in the double-stranded DNA in a process mediated by cellular protein factors. This annealing creates a centrally located mismatched base pair (in the case of a point mutation), resulting in a structural perturbation that most likely stimulates the endogenous protein machinery to initiate the second step in the repair process: site-specific modification of the chromosomal sequence and/or that in organelles (e.g., mitochondria and chloroplasts). This newly introduced mismatch induces the DNA repair machinery to perform a second repair event, leading to the final revision of the target site. The present methods and compositions in various aspects and embodiments disclosed herein, may improve the methods by providing novel approaches which increase the availability of DNA repair components, thus increasing the efficiency and reproducibility of gene repair-mediated modifications to targeted nucleic acids.

Efficient methods for site-directed genomic modifications are desirable for research, clinical gene therapy, industrial microbiology and agriculture. One approach utilizes triplex-forming oligonucleotides (TFO) which bind as third strands to duplex DNA in a sequence-specific manner, to mediate directed mutagenesis. Such TFO can act either by delivering a tethered mutagen, such as psoralen or chlorambucil (Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997), or by binding with sufficient affinity to provoke error-prone repair (Wang et al., Science 271:802-805, 1996).

Another strategy for genomic modification that may be used in conjunction with the compositions and methods herein involves the induction of homologous recombination between an exogenous DNA fragment and the targeted gene. This approach has been used successfully to target and disrupt selected genes in mammalian cells and has enabled the production of transgenic mice carrying specific gene knockouts (Capeechi et al., Science 244:1288-1292, 1989; Wagner, U.S. Pat. No. 4,873,191). This approach involves the transfer of selectable markers to allow isolation of the desired recombinants. Without selection, the ratio of homologous to non-homologous integration of transfected DNA in typical gene transfer experiments is low, usually in the range of 1:1000 or less (Sedivy et al., Gene Targeting, W. H. Freeman and Co., New York, 1992). This low efficiency of homologous integration limits the utility of gene transfer for experimental use or gene therapy. The frequency of targeted mutation can be enhanced by damage to the target site from UV irradiation and selected carcinogens (Wang et al., Mol Cell Biol 8:196-202, 1988) as well as by site-specific endonucleases (Sedivy et al, Gene Targeting, W. H. Freeman and Co., New York, 1992; Rouet et al., Proc Nat'l Acad Sci, U.S.A. 91:6064-6068, 1994; Segal et al., Proc Nat'l Acad Sci, U.S.A. 92:806-810, 1995). In addition, DNA damage induced by triplex-directed psoralen photoadducts can stimulate recombination within and between extrachromosomal vectors (Segal et al., Proc Nat'l Acad Sci, U.S.A. 92:806-810, 1995; Faruqi et al., Mol Cell Biol 16:6820-6828, 1996; Glazer, U.S. Pat. No. 5,962,426).

Linear donor fragments are more efficacious for targeted mutation than their circular counterparts (Folger et al., Mol Cell Biol 2:1372-1387, 1982). Recombination can in certain embodiments also be influenced by the length of uninterrupted homology between both the donor and target sites, with short fragments often appearing to be ineffective substrates (Rubnitz et al., Mol Cell Biol 4:2253-2258, 1984). Nonetheless, the use of short fragments of DNA or DNA/RNA hybrids for gene correction is the focus of various strategies. (Kunzelmann et al., Gene Ther 3:859-867, 1996).

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotide" and "oligomer" refer to a polymer of nucleobases. In some embodiments an "oligonucleotide" or "oligomer" may be of at least about 8 nucleobases or may have as many as about 1,500 nucleobases or more. In certain embodiments, an "oligonucleotide" or "oligomer" may be any length as contemplated herein.

The terms "DNA-modifying molecule" and "DNA-modifying reagent" as used herein refer to a molecule which is capable of recognizing and specifically binding to a nucleic acid sequence in the genome of a cell, and which is capable of modifying a target nucleotide sequence within the genome, wherein the recognition and specific binding of the DNA-modifying molecule to the nucleic acid sequence is protein-independent. The term "protein-independent" as used herein in connection with a DNA-modifying molecule means that the DNA-modifying molecule does not require the presence and/or activity of a protein and/or enzyme for the recognition of, and/or specific binding to, a nucleic acid sequence. DNA-modifying molecules are exemplified, but not limited to triplex forming oligonucleotides, peptide nucleic acids, polyamides, and oligonucleotides which are intended to promote gene conversion. The DNA-modifying molecules of the present disclosure are in certain embodiments distinguished from the prior art's nucleic acid sequences which are used for homologous recombination (Wong & Capecchi, Molec. Cell. Biol. 7:2294-2295, 1987) in that the prior art's nucleic acid sequences which are used for homologous recombination are protein-dependent. The term "protein-dependent" as used herein in connection with a molecule means that the molecule requires the presence and/or activity of a protein and/or enzyme for the recognition of, and/or specific binding of the molecule to, a nucleic acid sequence. Methods for determining whether a DNA-modifying molecule requires the presence and/or activity of a protein and/or enzyme for the recognition of, and/or specific binding to, a nucleic acid sequence are within the skill in the art (see, e.g., Dennis et al. Nucl. Acids Res. 27:4734-4742, 1999). For example, the DNA-modifying molecule may be incubated in vitro with the nucleic acid sequence in the absence of any proteins and/or enzymes. The detection of specific binding between the DNA-modifying molecule and the nucleic acid sequence demonstrates that the DNA-modifying molecule is protein-independent. On the other hand, the absence of specific binding between the DNA-modifying molecule and the nucleic acid sequence demonstrates that the DNA-modifying molecule is protein-dependent and/or requires additional factors.

"Triplex forming oligonucleotide" (TFO) is defined as a sequence of DNA or RNA that is capable of binding in the major grove of a duplex DNA or RNA helix to form a triple helix. Although the TFO is not limited to any particular length, a preferred length of the TFO is 250 nucleotides or less, 200 nucleotides or less, or 100 nucleotides or less, or from 5 to 50 nucleotides, or from 10 to 25 nucleotides, or from 15 to 25 nucleotides. Although a degree of sequence specificity between the TFO and the duplex DNA is necessary for formation of the triple helix, no particular degree of specificity is required, as long as the triple helix is capable of forming. Likewise, no specific degree of avidity or affinity between the TFO and the duplex helix is required as long as the triple helix is capable of forming. While not intending to limit the length of the nucleotide sequence to which the TFO specifically binds in one embodiment, the nucleotide sequence to which the TFO specifically binds is from 1 to 100, in some embodiments from 5 to 50, yet other embodiments from 10 to 25, and in other embodiments from 15 to 25, nucleotides. Additionally, "triple helix" is defined as a double-helical nucleic acid with an oligonucleotide bound to a target sequence within the double-helical nucleic acid. The "double-helical" nucleic acid can be any double-stranded nucleic acid including double-stranded DNA, double-stranded RNA and mixed duplexes of DNA and RNA. The double-stranded nucleic acid is not limited to any particular length. However, in preferred embodiments it has a length of greater than 500 bp, in some embodiments greater than 1 kb and in some embodiments greater than about 5 kb. In many applications the double-helical nucleic acid is cellular, genomic nucleic acid. The triplex forming oligonucleotide may bind to the target sequence in a parallel or anti-parallel manner.

"Peptide Nucleic Acids," "polyamides" or "PNA" are nucleic acids wherein the phosphate backbone is replaced with an N-aminoethylglycine-based polyamide structure. PNAs have a higher affinity for complementary nucleic acids than their natural counter parts following the Watson-Crick base-pairing rules. PNAs can form highly stable triple helix structures with DNA of the following stoichiometry: (PNA)2.DNA. Although the peptide nucleic acids and polyamides are not limited to any particular length, a preferred length of the peptide nucleic acids and polyamides is 200 nucleotides or less, in some embodiments 100 nucleotides or less, and in some embodiments from 5 to 50 nucleotides long. While not intending to limit the length of the nucleotide sequence to which the peptide nucleic acid and polyamide specifically binds, in one embodiment, the nucleotide sequence to which the peptide nucleic acid and polyamide specifically bind is from 1 to 100, in some embodiments from 5 to 50, yet other embodiments from 5 to 25, and other embodiments from 5 to 20, nucleotides.

The term "capable of modifying DNA" or "DNA modifying means" refers to procedures, as well as endogenous or exogenous agents or reagents that have the ability to induce, or can aid in the induction of, changes to the nucleotide sequence of a targeted segment of DNA. Such changes may be made by the deletion, addition or substitution of one or more bases on the targeted DNA segment. It is not necessary that the DNA sequence changes confer functional changes to any gene encoded by the targeted sequence. Furthermore, it is not necessary that changes to the DNA be made to any particular portion or percentage of the cells.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequence, enhancer sequence, polyadenylation sequence, termination sequence, regulatory RNAs such as miRNA, etc.).

"Amino acid sequence," "polypeptide sequence," "peptide sequence" and "peptide" are used interchangeably herein to refer to a sequence of amino acids.

"Target sequence," as used herein, refers to a double-helical nucleic acid comprising a sequence that is the subject of interest. In some embodiments a target sequence may be greater than 8 nucleotides in length and in some embodiments less than 1,500 nucleotides in length. In some embodiments, the target sequence is between 8 to 30 bases.

In some embodiments the target sequence may be between about 75 and 250 bases in length. In certain embodiments the target sequence may be a length complimentary to the length of an oligonucleotide as contemplated herein. The target sequence, in general, is defined by the nucleotide sequence on one of the strands on the double-helical nucleic acid.

As used herein, a "purine-rich sequence" or "polypurine sequence" when made in reference to a nucleotide sequence on one of the strands of a double-helical nucleic acid sequence is defined as a contiguous sequence of nucleotides wherein greater than 50% of the nucleotides of the target sequence contain a purine base. However, it is preferred that the purine-rich target sequence contain greater than 60% purine nucleotides, in some embodiments greater than 75% purine nucleotides, in other embodiments greater than 90% purine nucleotides and yet other embodiments 100% purine nucleotides.

As used herein, a "pyrimidine-rich sequence" or "polypyrimidine sequence" when made in reference to a nucleotide sequence on one of the strands of a double-helical nucleic acid sequence is defined as a contiguous sequence of nucleotides wherein greater that 50% of the nucleotides of the target sequence contain a pyrimidine base. However, it is preferred that the pyrimidine-rich target sequence contain greater than 60% pyrimidine nucleotides and in some embodiments greater than 75% pyrimidine nucleotides. In some embodiments, the sequence contains greater than 90% pyrimidine nucleotides and, in other embodiments, is 100% pyrimidine nucleotides.

A "variant" of a first nucleotide sequence is defined as a nucleotide sequence which differs from the first nucleotide sequence (e.g., by having one or more deletions, insertions, or substitutions that may be detected using hybridization assays or using DNA sequencing). Included within this definition is the detection of alterations or modifications to the genomic sequence of the first nucleotide sequence. For example, hybridization assays may be used to detect (1) alterations in the pattern of restriction enzyme fragments capable of hybridizing to the first nucleotide sequence when comprised in a genome (i.e., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g., using fluorescent in situ hybridization (FISH) to metaphase chromosomes spreads, etc.). One example of a variant is a mutated wild type sequence.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

As used herein, the terms "mutation" and "modification" and grammatical equivalents thereof when used in reference to a nucleic acid sequence are used interchangeably to refer to a deletion, insertion, substitution, strand break, and/or introduction of an adduct. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Pyrimidine to pyrimidine (e.g. C to T or T to C nucleotide substitutions) or purine to purine (e.g. G to A or A to G nucleotide substitutions) are termed transitions, whereas pyrimidine to purine or purine to pyrimidine (e.g. G to T or G to C or A to T or A to C) are termed transversions. Alternatively, a nucleic acid may be replaced by a modified nucleic acid as exemplified by replacement of a thymine by thymine glycol. Mutations may result in a mismatch. The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch (a transition) is present. The terms "introduction of an adduct" or "adduct formation" refer to the covalent or non-covalent linkage of a molecule to one or more nucleotides in a DNA sequence such that the linkage results in a reduction (in some embodiments from 10% to 100%, in other embodiments from 50% to 100%, and in some embodiments from 75% to 100%) in the level of DNA replication and/or transcription.

The term "DNA cutter" refers to a moiety that effects a strand break. Non-limited examples include meganucleases, TALEs/TALENs, antibiotics, zinc fingers and CRISPRs, which include but are not limited to Cas9, Cpf1 and their corresponding homologues, orthologues and/or paralogues, a base editor, or CRISPR/Cas systems.

The term "strand break" when made in reference to a double stranded nucleic acid sequence includes a single-strand break and/or a double-strand break. A single-strand break (a nick) refers to an interruption in one of the two strands of the double stranded nucleic acid sequence. This is in contrast to a double-strand break which refers to an interruption in both strands of the double stranded nucleic acid sequence, which may result in blunt or staggered ends. Strand breaks may be introduced into a double stranded nucleic acid sequence either directly (e.g., by ionizing radiation or treatment with certain chemicals) or indirectly (e.g., by enzymatic incision at a nucleic acid base). In certain embodiments, a DNA cutter may have selectivity for certain specific sequences, such as in the case of a CRISPR, which includes but is not limited to Cas9, Cpf1 and their corresponding homologues, orthologues and/or paralogues, a base editor, a zinc finger, a meganuclease, a TALEN as described herein.

The terms "mutant cell" and "modified cell" refer to a cell which contains at least one modification in the cell's genomic sequence.

The term "portion" when used in reference to a nucleotide sequence refers to fragments of that nucleotide sequence. The fragments may range in size from 5 nucleotide residues to the entire nucleotide sequence minus one nucleic acid residue.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer one or more DNA segment from one cell to another.

The terms "in operable combination," "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofectin, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids. For the sake of convenience, the terms "polynucleotides" and "oligonucleotides" include molecules which include nucleosides.

The terms "homology" and "homologous" as used herein in reference to nucleotide sequences refer to a degree of complementarity with other nucleotide sequences. There may be partial homology or complete homology (i.e., identity). When used in reference to a double-stranded nucleic acid sequence such as a cDNA or genomic clone, the term "substantially homologous" refers to any nucleic acid sequence (e.g., probe) which can hybridize to either or both strands of the double-stranded nucleic acid sequence under conditions of low stringency as described above. A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 68° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 2.0×SSPE, 0.1% SDS at room temperature when a probe of about 100 to about 1000 nucleotides in length is employed.

In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 μg/ml denatured salmon sperm DNA followed by washing in a solution comprising 0.1×SSPE and 0.1% SDS at 68° C. when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm = 81.5 + 0.41(\% \, G+C)$, when a nucleic acid is in aqueous solution at 1 M NaCl (see e.g., Anderson and Young, Quantitative Filter Hybridization, in Nucleic Acid Hybridization, 1985). Other references include more sophisticated computations which take structural as well as sequence characteristics into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm-5° C. (5° C. below the melting temperature of the probe) to about 20° C. to 25° C. below Tm. As will be understood by those of skill in the art, a stringent hybridization can be used to identify or detect identical polynucleotide sequences or to identify or detect similar or related polynucleotide sequences.

The terms "specific binding," "binding specificity," and grammatical equivalents thereof when made in reference to the binding of a first nucleotide sequence to a second nucleotide sequence, refer to the preferential interaction between the first nucleotide sequence with the second nucleotide sequence as compared to the interaction between the second nucleotide sequence with a third nucleotide sequence. Specific binding is a relative term that does not require absolute specificity of binding; in other words, the term "specific binding" does not require that the second nucleotide sequence interact with the first nucleotide sequence in the absence of an interaction between the second nucleotide sequence and the third nucleotide sequence. Rather, it is sufficient that the level of interaction between the first nucleotide sequence and the second nucleotide sequence is greater than the level of interaction between the second nucleotide sequence with the third nucleotide sequence. "Specific binding" of a first nucleotide sequence with a second nucleotide sequence also means that the interaction between the first nucleotide sequence and the second nucleotide sequence is dependent upon the presence of a particular structure on or within the first nucleotide sequence; in other words the second nucleotide sequence is recognizing and binding to a specific structure on or within the first nucleotide sequence rather than to nucleic acids or to nucleotide sequences in general. For example, if a second nucleotide sequence is specific for structure "A" that is on or within a first nucleotide sequence, the presence of a third nucleic acid sequence containing structure A will reduce the amount of the second nucleotide sequence which is bound to the first nucleotide sequence.

As used herein, the term "amplifiable nucleic acid" is used in reference to nucleic acids which may be amplified by any amplification method. It is contemplated that "amplifiable nucleic acid" will usually comprise "sample template."

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined as the production of additional copies of a nucleic acid sequence and is generally carried out using polymerase chain reaction technologies well known in the art (Dieffenbach and Dveksler (1995) PCR Primer, a Laboratory Manual, Cold Spring Harbor Press, Plainview, N.Y.). As used herein, the term "polymerase chain reaction" ("PCR") refers to the method of K. B. Mullis U.S. Pat. Nos. 4,683,195, and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

One such preferred method, particularly for commercial applications, is based on the widely used TaqMan® real-time PCR technology, and combines Allele-Specific PCR with a Blocking reagent (ASB-PCR) to suppress amplification of the wildtype allele. ASB-PCR can be used for detection of germ line or somatic mutations in either DNA or RNA extracted from any type of tissue, including formalin-fixed paraffin-embedded tumor specimens. A set of reagent design rules are developed enabling sensitive and selective detection of single point substitutions, insertions, or deletions against a background of wild-type allele in thousand-fold or greater excess. (Morlan, Baker, Sinicropi, Mutation Detection by Real-Time PCR: A Simple, Robust and Highly Selective Method. PLoS ONE 4(2): e4584, 2009)

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). In some embodiments, the primer is single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present disclosure will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present disclosure be limited to any particular detection system or label.

As used herein, the terms "restriction endonucleases" and "restriction enzymes" refer to bacterial enzymes, each of which cut or nick double- or single-stranded DNA at or near a specific nucleotide sequence, for example, an endonuclease domain of a type IIS restriction endonuclease (e.g., FokI can be used, as taught by Kim et al., 1996, Proc. Nat'l. Acad. Sci. USA, 6:1 156-60).

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Additionally "an oligonucleotide having a nucleotide sequence encoding a gene" may include suitable control elements such as enhancers, promoters, splice junctions, polyadenylation signals, etc. if needed to permit proper initiation of transcription and/or correct processing of the primary RNA transcript. Further still, the coding region of the present disclosure may contain endogenous enhancers, splice junctions, intervening sequences, polyadenylation signals, etc.

Transcriptional control signals in eukaryotes comprise "enhancer" elements. Enhancers consist of short arrays of DNA sequences that interact specifically with cellular proteins involved in transcription (Maniatis, T. et al., Science 236:1237, 1987). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York, pp. 16.7-16.8, 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element" or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

The term "tissue specific" as it applies to a promoter refers to a promoter that is capable of directing selective expression of an oligonucleotide sequence to a specific type of tissue in the relative absence of expression of the same oligonucleotide in a different type of tissue. Tissue specificity of a promoter may be evaluated by, for example, operably linking a reporter gene to the promoter sequence to generate a reporter construct, introducing the reporter construct into the genome of a plant or an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic plant or animal. Selectivity need not be absolute. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of an oligonucleotide sequence in a specific type of cell in the relative absence of expression of the same oligonucleotide sequence in a different type of cell within the same tissue. The term "cell type specific" when applied to a promoter also means a promoter capable of promoting selective expression of an oligonucleotide in a region within a single tissue. Again, selectivity need not be absolute. Cell type specificity of a promoter may be assessed using methods well known in the art, e.g., immunohistochemical staining as described herein. Briefly, tissue sections are embedded in paraffin, and paraffin sections are reacted with a primary antibody which is specific for the polypeptide product encoded by the oligonucleotide sequence whose expression is controlled by the promoter. As an alternative to paraffin sectioning, samples may be cryosectioned. For example, sections may be frozen prior to and during sectioning thus avoiding potential interference by residual paraffin. A labeled (e.g., peroxidase conjugated) secondary antibody which is specific for the primary antibody is allowed to bind to the sectioned tissue and specific binding detected (e.g., with avidin/biotin) by microscopy.

The terms "selective expression," "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "contiguous" when used in reference to two or more nucleotide sequences means the nucleotide sequences are ligated in tandem either in the absence of intervening sequences, or in the presence of intervening sequences which do not comprise one or more control elements.

As used herein, the terms "nucleic acid molecule encoding," "nucleotide encoding," "DNA sequence encoding" and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "substantially purified" refers to molecules, either nucleic or amino acid sequences, that are removed from their natural environment, isolated or separated, and are at least 60% free, in some embodiments 75% free and other embodiments 90% free from other components with which they are naturally associated. An "isolated polynucleotide" is, therefore, a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side generally by the nucleotide triplet "ATG" which encodes the initiator methionine and on the 3' side by one of the three triplets which specify stop codons (i.e., TAA, TAG, TGA).

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "peptide transcription factor binding site" or "transcription factor binding site" refers to a nucleotide sequence which binds protein transcription factors and, thereby, controls some aspect of the expression of nucleic acid sequences. For example, Sp-1 and AP1 (activator protein 1) binding sites are examples of peptide transcription factor binding sites.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, ayes, etc. Preferred non-human animals are selected from the order Rodentia. "Non-human animal" additionally refers to amphibians (e.g. *Xenopus*), reptiles, insects (e.g. *Drosophila*) and other non-mammalian animal species.

As used herein, the term "transgenic" refers to an organism or cell that has DNA derived from another organism inserted into which becomes integrated into the genome either of somatic and/or germ line cells of the plant or animal. A "transgene" means a DNA sequence which is partly or entirely heterologous (i.e., not present in nature) to the plant or animal in which it is found, or which is homologous to an endogenous sequence (i.e., a sequence that is found in the animal in nature) and is inserted into the plant' or animal's genome at a location which differs from that of the naturally occurring sequence. Transgenic plants or animals which include one or more transgenes are within the scope of this disclosure. Additionally, a "transgenic" as used herein refers to an organism that has had one or more genes modified and/or "knocked out" (made non-functional or made to function at reduced level, i.e., a "knockout" mutation) by the disclosure's methods, by homologous recombination, TFO mutation or by similar processes. For example, in some embodiments, a transgenic organism or cell includes inserted DNA that includes a foreign promoter and/or coding region.

A "transformed cell" is a cell or cell line that has acquired the ability to grow in cell culture for multiple generations, the ability to grow in soft agar, and/or the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, nucleofection and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein "exogenous" means that the gene encoding the protein is not normally expressed in the cell. Additionally, "exogenous" refers to a gene transfected into a cell to augment the normal (i.e. natural) level of expression of that gene.

A peptide sequence and nucleotide sequence may be "endogenous" or "heterologous" (i.e., "foreign"). The term "endogenous" refers to a sequence which is naturally found in the cell into which it is introduced so long as it does not contain some modification relative to the naturally-occurring sequence. The term "heterologous" refers to a sequence which is not endogenous to the cell into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes heterologous RNA and heterologous proteins that are not normally produced by the cell into which it is introduced.

Examples of heterologous DNA include reporter genes, transcriptional and translational regulatory sequences, DNA sequences which encode selectable marker proteins (e.g., proteins which confer drug resistance), etc.

In certain aspects and embodiments of the disclosures herein, provided are methods for introducing a gene repair oligonucleobase (GRON)-mediated mutation into a target deoxyribonucleic acid (DNA) sequence in a plant cell; for example for the purpose of modifying an FAD2 gene such as provided herein. In certain embodiments the methods may include, inter alia, culturing the plant cell under conditions that increase one or more cellular DNA repair processes prior to, and/or coincident with, delivery of a GRON into the plant cell; and/or delivery of a GRON into the plant cell greater than 15 bases in length, the GRON optionally comprising one or more; or two or more; mutation sites (such as FAD2 mutation sites as provided herein) for introduction into the target DNA.

A "gene repair oligonucleotide" or "GRON" as used herein means an oligonucleobase (e.g., mixed duplex oligonucleotides, non-nucleotide containing molecules, single stranded oligodeoxynucleotides, double stranded oligodeoxynucleotides and other gene repair molecules) that can under certain conditions direct single, or in some embodiments multiple, nucleotide deletions, insertions or substitutions in a DNA sequence. This oligonucleotide-mediated gene repair editing of the genome may comprise both non-homology based repair systems (e.g., non-homologous end joining) and homology-based repair systems (e.g., homology-directed repair). The GRON is typically designed to align in register with a genomic target except for the designed mismatch(es). These mismatches can be recognized and corrected by harnessing one or more of the cell's endogenous DNA repair systems. In some embodiments a GRON or oligonucleotide can be designed to contain multiple differences when compared to the organisms target sequence. These differences may not all affect the protein sequence translated from said target sequence and in one or more cases be known as silent changes. Numerous variations of GRON structure, chemistry and function are described elsewhere herein. In various embodiments, a GRON as used herein may have one or more modifications. For example, a GRON as used herein may have one or more modifications that attract DNA repair machinery to the targeted (mismatch) site and/or that prevent recombination of part or all of the GRON (other than the desired targeted deletions, insertions, substitutions or the like) into the genomic DNA of the target DNA sequence and/or that increase the stability of the GRON.

In various embodiments, a GRON may have both RNA and DNA nucleotides and/or other types of nucleobases. In some embodiments, one or more of the DNA or RNA nucleotides comprise a modification.

In one aspect, provided is a method of causing a genetic change in a plant cell (for example a genetic change in a FAD2 gene), wherein the method involves exposing the cell to a DNA cutter and a GRON, for example a GRON that is modified as contemplated herein. In some embodiments the GRON may be modified such as with a Cy3 group, 3PS group, a 2'O-methyl group or other modification such as contemplated herein. In another aspect, provided is a plant cell that includes a DNA cutter and a GRON (such as a GRON that binds and/or modifies a FAD2 gene), for example where the GRON is modified such as with a Cy3 group, 3PS group, a 2'O-methyl group or other modification. In some embodiments, the DNA cutter is one or more selected from a CRISPR, which includes but is not limited to Cas9, Cpf1 and their corresponding homologues, orthologues and/or paralogues, a base editor, a TALEN, a zinc finger, meganuclease, and a DNA-cutting antibiotic. In some embodiments, the DNA cutter is a CRISPR which includes but is not limited to Cas9, Cpf1 and their corresponding homologues, orthologues and/or paralogues, a base editor. In some embodiments, the DNA cutter is a TALEN. The DNA cutter can be plasmid (DNA) based, RNA and/or protein. In some embodiments, the GRON is between 15 and 60 nucleobases in length; or between 30 and 40 nucleobases in length; or between 35 and 45 nucleobases in length; or between 20 and 70 nucleobases in length; or between 20 and 200 nucleobases in length; or between 30 and 180 nucleobases in length; or between 50 and 160 nucleobases in length; or between 70 and 150 nucleobases in length; or between 80 and 120 nucleobases in length; or between 90 and 110 nucleobases in length; or between 95 and 105 nucleobases in length; or between 80 and 300 nucleobases in length; or between 90 and 250 nucleobases in length; or between 100 and 150 nucleobases in length; or between 100 and 300 nucleobases in length; or between 150 and 200 nucleobases in length; or between 200 and 300 nucleobases in length; or between 250 and 350 nucleobases in length; or between 50 and 110 nucleobases in length; or between 50 and 200 nucleobases in length; or between 150 and 210 nucleobases in length; or between 20 and 1000 nucleobases in length; or between 100 and 1000 nucleobases in length; or between 200 and 1000 nucleobases in length; or between 300 and 1000 nucleobases in length; or between 400 and 1000 nucleobases in length; or between 500 and 1000 nucleobases in length; or between 600 and 1000 nucleobases in length; or between 700 and 1000 nucleobases in length; or between 800 and 1000 nucleobases in length; or between 900 and 1000 nucleobases in length; or between 300 and 800 nucleobases in length; or between 400 and 600 nucleobases in length; or between 500 and 700 nucleobases in length; or between 600 and 800 nucleobases in length; or longer than 30 nucleobases in length; or longer than 35 nucleobases in length; or longer than 40 nucleobases in length; or longer than 50 nucleobases in length; or longer than 60 nucleobases in length; or longer than 65 nucleobases in length; or longer than 70 nucleobases in length; or longer than 75 nucleobases in length; or longer than 80 nucleobases in length; or longer than 85 nucleobases in length; or longer than 90 nucleobases in length; or longer than 95 nucleobases in length; or longer than 100 nucleobases in length; or longer than 110 nucleobases in length; or longer than 125 nucleobases in length; or longer than 150 nucleobases in length; or longer than 165 nucleobases in length; or longer than 175 nucleobases in length; or longer than 200 nucleobases in length; or longer than 250 nucleobases in length; or longer than 300 nucleobases in length; or longer than 350 nucleobases in length; or longer than 400 nucleobases in length; or longer than 450 nucleobases in length; or longer than 500 nucleobases in length; or longer than 550 nucleobases in length; or longer than 600 nucleobases in length; or longer than 700 nucleobases in length; or longer than 800 nucleobases in length; or longer than 900 nucleobases in length.

GRONs may be targeted at both non-coding (NC) and coding (C) regions of a target gene.

The term "CRISPR" as used herein refers to elements; i.e., a Cas (CRISPR associated) gene, transcript (e.g., mRNA) and/or protein and at least one CRISPR spacer sequence (Clustered Regularly Interspaced Short Palindromic Repeats, also known as SPIDRs—SPacer Interspersed Direct Repeats); that when effectively present or expressed in a cell could effect cleavage of a target DNA sequence via CRISPR/CAS cellular machinery such as described in e.g., Cong et al., Science, vol. 339 no 6121 pp. 819-823 (2013); Jinek et al, Science, vol. 337:816-821 (2013); Wang et al., RNA, vol. 14, pp. 903-913 (2008); Zhang et al., Plant Physiology, vol. 161, pp. 20-27 (2013), Zhang et al, PCT Application No. PCT/US2013/074743; and Charpentier et al., PCT Application No. PCT/US2013/032589. In some embodiments, such as for example a CRISPR for use in a eukaryotic cell, a CRISPR as contemplated herein may also include an additional element that includes a sequence for one or more functional nuclear localization signals. CRISPRs as contemplated herein can be expressed in, administered to and/or present in a cell (such as a plant cell) in any of many ways or manifestations. For example a CRISPR as contemplated herein may include or involve one or more of a CRISPR on a plasmid, a CRISPR nickase on a plasmid, a CRISPRa on a plasmid, or a CRISPRi on a plasmid as follows:

CRISPR on a plasmid: A recombinant expression vector comprising:

(i) a nucleotide sequence encoding a DNA-targeting RNA (e.g., guide RNA), wherein the DNA-targeting RNA comprises:

a. a first segment comprising a nucleotide sequence that is complementary to a sequence in a target DNA (e.g., protospacer, spacer, or crRNA); and b. a second segment that interacts with a site-directed modifying polypeptide (e.g., trans-activating crRNA or tracrRNA); and (ii) a nucleotide sequence encoding the site-directed modifying polypeptide (e.g., Cas gene), wherein the site-directed polypeptide comprises:

a. an RNA-binding portion that interacts with the DNA-targeting RNA (e.g., REC lobe); and b. an activity portion that causes double-stranded breaks within the target DNA (e.g., NUC lobe), wherein the site of the double-stranded breaks within the target DNA is determined by the DNA-targeting RNA.

CRISPR nickase on a plasmid. A recombinant expression vector comprising:

(i) a nucleotide sequence encoding a DNA-targeting RNA (e.g., guide RNA), wherein the DNA-targeting RNA comprises:

a. a first segment comprising a nucleotide sequence that is complementary to a sequence in a target DNA (e.g., protospacer, spacer, or crRNA); and b. a second segment that interacts with a site-directed modifying polypeptide (e.g., trans-activating crRNA or tracrRNA); and (ii) a nucleotide sequence encoding the site-directed modifying polypeptide (e.g., Cas gene), wherein the site-directed polypeptide comprises:

a. an RNA-binding portion that interacts with the DNA-targeting RNA (e.g., REC lobe); and b. an activity portion that causes single-stranded breaks within the target DNA (e.g., NUC lobe), wherein the site of the single-stranded breaks within the target DNA is determined by the DNA-targeting RNA.

CRISPRa on a plasmid. A recombinant expression vector comprising:

(i) a nucleotide sequence encoding a DNA-targeting RNA (e.g., guide RNA), wherein the DNA-targeting RNA comprises:

a. a first segment comprising a nucleotide sequence that is complementary to a sequence in a target DNA (e.g., protospacer, spacer, or crRNA); and b. a second segment that interacts with a site-directed modifying polypeptide (e.g., trans-activating crRNA or tracrRNA); and (ii) a nucleotide sequence encoding the site-directed modifying polypeptide (e.g., Cas gene), wherein the site-directed polypeptide comprises:

a. an RNA-binding portion that interacts with the DNA-targeting RNA (e.g., REC lobe); and b. an activity portion that modulates transcription (e.g., NUC lobe; in certain embodiments increases transcription) within the target DNA, wherein the site of the transcriptional modulation within the target DNA is determined by the DNA-targeting RNA.

CRISPRi on a plasmid. A recombinant expression vector comprising:

(i) a nucleotide sequence encoding a DNA-targeting RNA (e.g., guide RNA), wherein the DNA-targeting RNA comprises:

a. a first segment comprising a nucleotide sequence that is complementary to a sequence in a target DNA (e.g., protospacer, spacer, or crRNA); and b. a second segment that interacts with a site-directed modifying polypeptide (e.g., trans-activating crRNA or tracrRNA); and (ii) a nucleotide sequence encoding the site-directed modifying polypeptide (e.g., Cas gene), wherein the site-directed polypeptide comprises:

a. an RNA-binding portion that interacts with the DNA-targeting RNA (e.g., REC lobe); and b. an activity portion that modulates transcription/ translation (e.g., NUC lobe; in some embodiments decreases transcription/translation) within the target DNA, wherein the site of transcriptional/translational modulation within the target DNA is determined by the DNA-targeting RNA.

Each of the CRISPR on a plasmid, CRISPR nickase on a plasmid, CRISPRa on a plasmid, and CRISPRi on a plasmid may in some embodiments alternatively have one or more appropriate elements be administered, expressed or present in a cell as an RNA (e.g., mRNA) or a protein rather than on a plasmid. Delivery of protected mRNA may be as described in Kariko, et al, U.S. Pat. No. 8,278,036.

In some embodiments, each of the CRISPRi and CRISPRa may include a deactivated cas9 (dCas9). A deactivated cas9 still binds to target DNA, but does not have cutting activity. Nuclease-deficient Cas9 can result from D10A and H840A point mutations which inactivates its two catalytic domains.

In some embodiments, a CRISPRi inhibits transcription initiation or elongation via steric hindrance of RNA Polymerase II. CRISPRi can optionally be enhanced (CRISPRei) by fusion of a strong repressor domain to the C-terminal end of a dCas9 protein. In some embodiments, a repressor domain recruits and employs chromatin modifiers. In some embodiments, the repressor domain may include, but is not limited to domains as described in Kagale et al., Epigenetics, vol. 6 no 2 pp 141-146 (2011):

```
1.
                                          (SEQ ID NO: 9)
LDLNRPPPVEN
OsERF3 repressor domain ("LxLxPP" motif)
```

-continued

```
2.
                                    (SEQ ID NO: 10)
LRLFGVNM
AtBRD repressor domain ("R/KLFGV" motif)

3.
                                    (SEQ ID NO: 11)
LKLFGVWL
AtHsfB1 repressor domain ("R/KLFGV" motif)

4.
                                    (SEQ ID NO: 12)
LDLELRLGFA
AtSUP repressor domain ("EAR" motif)

5.
                                    (SEQ ID NO: 13)
ERSNSIELRNSFYGRARTSPWSYGDYDNCQQDHDYLLGFSWPPRSYTCSF

CKREFRSAQALGGHMNVHRRDRARLRLQQSPSSSSTPSPPYPNPNYSYST

MANSPPPHHSPLTLFPTLSPPSSPRYRAGLIRSLSPKSKHTPENACKTKK

SSLLVEAGEATRFTSKDACKILRNDEIISLELEIGLINESEQDLDLELRL

GFA*
full AtSUP gene containing repressor domain
("EAR" motif)
```

In some embodiments, a CRISPRa activation of transcription achieved by use of dCas9 protein containing a fused C-terminal end transcriptional activator. In some embodiments, an activation may include, but is not limited to VP64 (4× VP16), AtERF98 activation domain, or AtERF98x4 concatemers such as described in Cheng et al., Cell Research, pp 1-9 (2013); Perez-Pinera et al., Nature Methods, vol. 10 pp 913-976 (2013); Maeder et al., Nature Methods, vol. 10 pp 977-979 (2013) and Mali et al., Nature Biotech., vol. 31 pp 833-838 (2013).

In some embodiments the CRISPR includes a nickase. In certain embodiments, two or more CRISPR nickases are used. In some embodiments, the two or more nickases cut on opposite strands of target nucleic acid. In other embodiments, the two or more nickases cut on the same strand of target nucleic acid.

As used herein, "repressor protein" or "repressor" refers to a protein that binds to operator of DNA or to RNA to prevent transcription or translation, respectively.

As used herein, "repression" refers to inhibition of transcription or translation by binding of repressor protein to specific site on DNA or mRNA. In some embodiments, repression includes a significant change in transcription or translation level of at least 1.5-fold, in other embodiments at least two-fold, and in other embodiments at least five-fold.

As used herein, an "activator protein" or "activator" with regard to gene transcription and/or translation, refers to a protein that binds to operator of DNA or to RNA to enhance or increase transcription or translation, respectively.

As used herein with regard to gene transcription and/or translation, "activation" with regard to gene transcription and/or translation, refers to enhancing or increasing transcription or translation by binding of activator protein to specific site on DNA or mRNA. In some embodiments, activation includes a significant change in transcription or translation level of at least 1.5-fold, in some embodiments at least two-fold, and in some embodiments at least five-fold.

In certain embodiments, conditions that increase one or more cellular DNA repair processes may include one or more of: introduction of one or more sites into the GRON or into the plant cell DNA that are targets for base excision repair, introduction of one or more sites into the GRON or into the plant cell DNA that are targets for non-homologous end joining, introduction of one or more sites into the GRON or into the plant cell DNA that are targets for microhomology-mediated end joining, introduction of one or more sites into the GRON or into the plant cell DNA that are targets for homologous recombination, and introduction of one or more sites into the GRON or into the plant cell DNA that are targets for effecting repair (e.g., base-excision repair (BER); homologous recombination repair (HR); mismatch repair (MMR); non-homologous end-joining repair (NHEJ) which include classical and alternative NHEJ; and nucleotide excision repair (NER)).

As described herein, GRONs for use herein may include one or more of the following (non-limiting) alterations from conventional RNA and DNA nucleotides:

one or more abasic nucleotides;
   one or more 8'oxo dA and/or 8'oxo dG nucleotides;
   a reverse base at the 3' end thereof;
   one or more 2'O-methyl nucleotides;
   one or more RNA nucleotides;
   one or more RNA nucleotides at the 5' end thereof, and in some embodiments 2, 3, 4, 5, 6, 7, 8, 9, 10, or more; wherein one or more of the RNA nucleotides may further be modified; one or more RNA nucleotides at the 3' end thereof, and in some embodiments 2, 3, 4, 5, 6, 7, 8, 9, 10, or more; wherein one or more of the RNA nucleotides may further be modified;
   one or more 2'O-methyl RNA nucleotides at the 5' end thereof, and in some embodiments 2, 3, 4, 5, 6, 7, 8, 9, 10, or more;
   an intercalating dye;
   a 5' terminus cap;
   a backbone modification selected from the group consisting of a phosphothioate modification, a methyl phosphonate modification, a locked nucleic acid (LNA) modification, a O-(2-methoxyethyl) (MOE) modification, a diPS modification, and a peptide nucleic acid (PNA) modification;
   one or more intrastrand crosslinks;
   one or more fluorescent dyes conjugated thereto, and in some embodiments at the 5' or 3' end of the GRON; and
   one or more bases which increase hybridization energy.

The term "wobble base" as used herein refers to a change in a one or more nucleotide bases of a reference nucleotide sequence wherein the change does not change the sequence of the amino acid coded by the nucleotide relative to the reference sequence.

The term "non-nucleotide" or "abasic nucleotide" as use herein refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. It may have substitutions for a 2' or 3' H or OH as described in the art and herein.

As described herein, in certain embodiments GRON quality and conversion efficiency may be improved by synthesizing all or a portion of the GRON using nucleotide multimers, such as dimers, trimers, tetramers, etc. improving its purity.

In certain embodiments, the target deoxyribonucleic acid (DNA) sequence is within a plant cell, for example the target DNA sequence is in the plant cell genome. The plant cell may be non-transgenic or transgenic, and the target DNA sequence may be a transgene or an endogenous gene of the plant cell.

In certain embodiments, the conditions that increase one or more cellular DNA repair processes comprise introducing one or more compounds which induce single or double DNA strand breaks into the plant cell prior to, or coincident to, or after delivering the GRON into the plant cell. Exemplary compounds are described herein.

In certain embodiments, the methods further comprise regenerating a plant having a mutation introduced by the GRON from the plant cell, and may comprise collecting seeds from the plant.

In related aspects, the present disclosure relates to plant cells comprising a genomic modification introduced by a GRON according to the methods described herein, a plant comprising a genomic modification introduced by a GRON according to the methods described herein, or a seed comprising a genomic modification introduced by a GRON according to the methods described herein; or progeny of a seed comprising a genomic modification introduced by a GRON according to the methods described herein.
Constructs The nucleic acid molecules disclosed herein (e.g., site specific nucleases, or guide RNA for CRISPRs) can be used in the production of recombinant nucleic acid constructs. In one embodiment, the nucleic acid molecules of the present disclosure can be used in the preparation of nucleic acid constructs, for example, expression cassettes for expression in the plant, microorganism, or animal of interest such as FAD2 expression constructs optionally having one or more mutations as described herein. This expression may be transient for instance when the construct is not integrated into the host genome or maintained under the control offered by the promoter and the position of the construct within the host's genome if it becomes integrated.

Expression cassettes may include regulatory sequences operably linked to the site specific nuclease or guide RNA sequences disclosed herein. The cassette may additionally contain at least one additional gene to be co-transformed into the organism. Alternatively, the additional gene or genes can be provided on multiple expression cassettes.

The nucleic acid constructs may be provided with a plurality of restriction sites for insertion of the site specific nuclease coding sequence to be under the transcriptional regulation of the regulatory regions. The nucleic acid constructs may additionally contain nucleic acid molecules encoding for selectable marker genes.

Any promoter can be used in the production of the nucleic acid constructs. The promoter may be native or analogous, or foreign or heterologous, to the plant, microbial, or animal host nucleic acid sequences disclosed herein. Additionally, the promoter may be the natural sequence or alternatively a synthetic sequence. Where the promoter is "foreign" or "heterologous" to the plant, microbial, or animal host, it is intended that the promoter is not found in the native plant, microbial, or animal into which the promoter is introduced. As used herein, a chimeric gene comprises a coding sequence operably linked to a transcription initiation region that is heterologous to the coding sequence.

The site directed nuclease sequences disclosed herein may be expressed using heterologous promoters.

Any promoter can be used in the preparation of constructs to control the expression of the site directed nuclease sequences, such as promoters providing for constitutive, tissue-preferred, inducible, or other promoters for expression in plants, microbes, or animals. Constitutive promoters include, for example, the core promoter of the Rsyn7 promoter and other constitutive promoters disclosed in WO 99/43 838 and U.S. Pat. No. 6,072,050; the core CaMV 35S promoter (Odell et al. Nature 313:810-812; 1985); rice actin (McElroy et al., Plant Cell 2:163-171, 1990); ubiquitin (Christensen et al., Plant Mol. Biol. 12:619-632, 1989 and Christensen et al., Plant Mol. Biol. 18:675-689, 1992); pEMU (Last et al., Theor. Appl. Genet. 81:581-588, 1991); MAS (Velten et al., EMBO J. 3:2723-2730, 1984); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to direct site directed nuclease expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al., Plant J. 12(2): 255-265, 1997; Kawamata et al., Plant Cell Physiol. 38(7): 792-803, 1997; Hansen et al., Mol. Gen Genet. 254(3):337-343, 1997; Russell et al., Transgenic Res. 6(2):157-168, 1997; Rinehart et al., Plant Physiol. 1 12(3):1331-1341, 1996; Van Camp et al., Plant Physiol. 1 12(2):525-535, 1996; Canevascini et al., Plant Physiol. 112(2): 513-524, 1996; Yamamoto et al., Plant Cell Physiol. 35(5):773-778, 1994; Lam, Results Probl. Cell Differ. 20:181-196, 1994; Orozco et al. Plant Mol Biol. 23(6):1129-1138, 1993; Matsuoka et al., Proc Nat'l. Acad. Sci. USA 90(20):9586-9590, 1993; and Guevara-Garcia et al., Plant J. 4(3):495-505, 1993.

The nucleic acid constructs may also include transcription termination regions. Where transcription terminations regions are used, any termination region may be used in the preparation of the nucleic acid constructs. For example, the termination region may be derived from another source (i.e., foreign or heterologous to the promoter). Examples of termination regions that are available for use in the constructs of the present disclosure include those from the Ti-plasmid of A. tumefaciens, such as the octopine synthase and nopaline synthase termination regions. See also Guerineau et al., Mol. Gen. Genet. 262:141-144, 1991; Proudfoot, Cell 64:671-674, 1991; Sanfacon et al., Genes Dev. 5:141-149, 1991; Mogen et al., Plant Cell 2:1261-1272, 1990; Munroe et al., Gene 91:151-158, 1990; Ballas et al., Nucleic Acids Res. 17:7891-7903, 1989; and Joshi et al., Nucleic Acid Res. 15:9627-9639, 1987.

In conjunction with any of the aspects, embodiments, methods and/or compositions disclosed herein, the nucleic acids may be optimized for increased expression in the transformed plant. That is, the nucleic acids encoding the site directed nuclease proteins can be synthesized using plant-preferred codons for improved expression. See, for example, Campbell and Gowri, (Plant Physiol. 92:1-11, 1990) for a discussion of host-preferred codon usage. Methods are available in the art for synthesizing plant-preferred genes. See, for example, U.S. Pat. Nos. 5,380,831, and 5,436,391, and Murray et al., Nucleic Acids Res. 17:477-498, 1989. See also e.g., Lanza et al., BMC Systems Biology 8:33-43, 2014; Burgess-Brown et al., Protein Expr. Purif. 59:94-102, 2008; Gustafsson et al., Trends Biotechnol 22:346-353, 2004.

In addition, other sequence modifications can be made to the nucleic acid sequences disclosed herein. For example, additional sequence modifications are known to enhance gene expression in a cellular host. These include elimination of sequences encoding spurious polyadenylation signals, exon/intron splice site signals, transposon-like repeats, and other such well-characterized sequences that may be deleterious to gene expression. The G-C content of the sequence may also be adjusted to levels average for a target cellular host, as calculated by reference to known genes expressed in the host cell. In addition, the sequence can be modified to avoid predicted hairpin secondary mRNA structures.

Other nucleic acid sequences may also be used in the preparation of the constructs of the present disclosure, for example to enhance the expression of the site directed nuclease coding sequence. Such nucleic acid sequences include the introns of the maize Adhl, intronl gene (Callis et al., Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al., Nucleic Acid Res. 15:8693-8711, 1987; and Skuzeski et al., Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize site directed nuclease gene expression, the plant expression vectors disclosed herein may also contain DNA sequences containing matrix attachment regions (MARs). Plant cells transformed with such modified expression systems, then, may exhibit overexpression or constitutive expression of a nucleotide sequence of the disclosure.

The expression constructs disclosed herein can also include nucleic acid sequences capable of directing the expression of the site directed nuclease sequence to the chloroplast or other organelles and structures in both prokaryotes and eukaryotes. Such nucleic acid sequences include chloroplast targeting sequences that encodes a chloroplast transit peptide to direct the gene product of interest to plant cell chloroplasts. Such transit peptides are known in the art. With respect to chloroplast-targeting sequences, "operably linked" means that the nucleic acid sequence encoding a transit peptide (i.e., the chloroplast-targeting sequence) is linked to the site directed nuclease nucleic acid molecules disclosed herein such that the two sequences are contiguous and in the same reading frame. See, for example, Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233:478-481, 1986.

Chloroplast targeting sequences are known in the art and include the chloroplast small subunit of ribulose-1,5-bisphosphate carboxylase (Rubisco) (de Castro Silva Filho et al., Plant Mol. Biol. 30:769-780, 1996; Schnell et al., J. Biol. Chem. 266(5):3335-3342, 1991); 5-(enolpyruvyl)shikimate-3-phosphate synthase (EPSPS) (Archer et al., J. Bioenerg. Biomemb. 22(6):789-810, 1990); tryptophan synthase (Zhao et al., J. Biol. Chem. 270(1 1):6081-6087, 1995); plastocyanin (Lawrence et al., J. Biol. Chem. 272(33):20357-20363, 1997); chorismate synthase (Schmidt et al., J. Biol. Chem. 268(36):27447-27457, 1993); and the light harvesting chlorophyll a/b binding protein (LHBP) (Lamppa et al., J. Biol. Chem. 263:14996-14999, 1988). See also Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233: 478-481, 1986.

In conjunction with any of the aspects, embodiments, methods and/or compositions disclosed herein, the nucleic acid constructs may be prepared to direct the expression of the mutant site directed nuclease coding sequence from the plant cell chloroplast. Methods for transformation of chloroplasts are known in the art. See, for example, Svab et al., Proc. Nat'l. Acad. Sci. USA 87:8526-8530, 1990; Svab and Maliga, Proc. Nat'l. Acad. Sci. USA 90:913-917, 1993; Svab and Maliga, EMBO J. 12:601-606, 1993. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. Proc. Nat'l. Acad. Sci. USA 91:7301-7305, 1994.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The nucleic acid constructs can be used to transform plant cells and regenerate transgenic plants comprising the site directed nuclease coding sequences. Numerous plant transformation vectors and methods for transforming plants are available. See, for example, U.S. Pat. No. 6,753,458, An et al., Plant Physiol., 81:301-305, 1986; Fry et al., Plant Cell Rep. 6:321-325, 1987; Block Theor. Appl Genet. 76:767-774, 1988; Hinchee et al., Stadler. Genet. Symp. 203212.203-212, 1990; Cousins et al., Aust. J. Plant Physiol. 18:481-494, 1991; Chee and Slightom Gene. 118:255-260, 1992; Christou et al., Trends. Biotechnol. 10:239-246, 1992; D'Halluin et al., Bio/Technol. 10:309-3 14, 1992; Dhir et al., Plant Physiol. 99:81-88, 1992; Casas et al., Proc. Nat'l. Acad Sci. USA 90:11212-11216, 1993; Christou, P., In Vitro Cell. Dev. Biol.-Plant 29P:1 19-124, 1993; Davies, et al., Plant Cell Rep. 12:180-183, 1993; Dong and Mc Hughen Plant Sci. 91:139-148, 1993; Franklin Trieu Cassidy Dixon Nelson 1993, Plant Cell Report 12, 74-79; Golovkin et al., Plant Sci. 90:41-52, 1993; Guo Chin Sci. Bull. 38:2072-2078; Asano et al., Plant Cell Rep. 13, 1994; Ayeres and Park Crit. Rev. Plant. Sci. 13:219-239, 1994; Barcelo et al., Plant. J. 5:583-592, 1994; Becker, et al., Plant. J. 5:299-307, 1994; Borkowska et al., Acta. Physiol Plant. 16:225-230, 1994; Christou Agro. Food. Ind. Hi Tech. 5:17-27, 1994; Eapen et al., Plant Cell Rep. 13:582-586, 1994; Hartman et al., Bio-Technology 12:919923, 1994; Ritala et al., Plant. Mol. Biol. 24:317-325, 1994; and Wan and Lemaux Plant Physiol. 104:3748, 1994. The constructs may also be transformed into plant cells using homologous recombination.

The term "wild-type" when made in reference to a peptide sequence and nucleotide sequence refers to a peptide sequence and nucleotide sequence (locus/gene/allele), respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. "Wild-type" may also refer to the sequence at a specific nucleotide position or positions, or the sequence at a particular codon position or positions, or the sequence at a particular amino acid position or positions.

"Consensus sequence" is defined as a sequence of amino acids or nucleotides that contain identical amino acids or nucleotides or functionally equivalent amino acids or nucleotides for at least 25% of the sequence. The identical or functionally equivalent amino acids or nucleotides need not be contiguous.

A nucleobase is a base, which in certain preferred embodiments is a purine, pyrimidine, or a derivative or analog thereof. Nucleosides are nucleobases that contain a pentose-furanosyl moiety, e.g., an optionally substituted riboside or 2'-deoxyriboside. Nucleosides can be linked by one of several linkage moieties, which may or may not contain phosphorus. Nucleosides that arc linked by unsubstituted phosphodiester linkages are termed nucleotides. The term "nucleobase" as used herein includes peptide nucleobases, the subunits of peptide nucleic acids, and morpholine nucleobases as well as nucleosides and nucleotides.

An oligonucleobase is a polymer comprising nucleobases; in some embodiments at least a portion of which can hybridize by Watson-Crick base pairing to a DNA having the complementary sequence. An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that may be complementary and hybridized by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In certain embodiments, an oligonucleobase strand may include both oligonucleobase chains and segments or regions of oligonucleobase chains. An oligonucleobase strand may have a 3' end and a 5' end, and when an oligonucleobase strand is coextensive with a chain, the 3' and 5' ends of the strand are also 3' and 5' termini of the chain.

As used herein the term "codon" refers to a sequence of three adjacent nucleotides (either RNA or DNA) constituting the genetic code that determines the insertion of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

"Heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

As used herein, "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted, or is not present on the homologous chromosome segment. As used herein "hemizygous" may also refer to a sample, a cell, a cell population or an organism in which an allele at one or more genetic loci may be detected only once in the genotype.

The term "zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in at a single nucleotide position in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele).

As used herein, the term "RTDS" refers to the Rapid Trait Development System™ (RTDS™) developed by Cibus. RTDS™ is a suite of technologies enabling site-specific gene modification using a system that is effective at making precise changes in a gene sequence without the incorporation of foreign genes or control sequences. Site-specific gene modification is followed by regeneration of cells with these precise changes into plants bearing these changes.

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

RTDS and Repair Oligonucleotides (GRONs)

Various aspects and embodiments of the methods and compositions contemplated herein include methods to improve the efficiency of the targeting of modifications to specific locations in genomic or other nucleotide sequences (for example modifications to an FAD2 gene such as contemplated herein).

RTDS in some embodiments is based on altering a targeted gene by utilizing the cell's own gene repair system to specifically modify the gene sequence in situ and not insert foreign DNA and gene expression control sequences. This procedure can effect a precise change in the genetic sequence while the rest of the genome is left unaltered. In some embodiments, in contrast to conventional transgenic GMOs, there is no integration of foreign genetic material, nor is any foreign genetic material left in the plant. The changes in the genetic sequence introduced by RTDS are not randomly inserted. Since affected genes remain in their native location, no random, uncontrolled or adverse pattern of expression occurs.

The molecule that effects this change is a chemically synthesized oligonucleotide (GRON) as described herein which may be composed of both DNA and modified RNA bases as well as other chemical moieties, and is designed to hybridize at the targeted gene location to create or make a mismatched base-pair. This mismatched base-pair acts as a signal to attract the cell's own natural gene repair system to that site and correct (replace, insert or delete) the designated nucleotide or nucleotides within the gene. Once the correction process is complete the GRON molecule is degraded and the now-modified or repaired gene is expressed under that gene's normal endogenous control mechanisms.

The methods and compositions disclosed herein can be practiced or made with "gene repair oligonucleobases" (GRON) having the conformations and chemistries as described in detail herein and below. The "gene repair oligonucleobases" as contemplated herein have also been described in published scientific and patent literature using other names including "recombinagenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "Single stranded oligodeoxynucleotide mutational vectors" (SSOMVs); "duplex mutational vectors;" and "heteroduplex mutational vectors." The gene repair oligonucleobase can be introduced into a plant cell using any method commonly used in the art, including but not limited to, microcarriers (biolistic delivery), microfibers, polyethylene glycol (PEG)-mediated uptake, electroporation, and microinjection.

In one embodiment, the gene repair oligonucleobase is a mixed duplex oligonucleotides (MDON) in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a T-OH substituted with a substituent described in the Martin Applications or Sproat is termed a "T-substituted ribonucleotide." As used herein the term "RNA-type nucleotide" means a T-hydroxyl or 2'-substituted nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a T-H, which can be linked to other nucleotides of a gene repair oligonucleobase by an unsubstituted phosphodiester linkage or any of the non-natural linkages taught by Kmiec I or Kmiec II.

In particular embodiments of the present disclosure, the gene repair oligonucleobase may be a mixed duplex oligonucleotide (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, T-methoxy, 2'-propyloxy, 2'-allyloxy, 2'-hydroxylethyloxy, 2'-methoxyethyloxy, T-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotides (MDONs) having only a single type of 2'-substituted RNA-type nucleotide are more conveniently synthesized, the methods of the disclosure can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides in some embodiments have fewer than 100 nucleotides and other embodiments fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene/allele, i.e., have the same sequence as the target gene/allele. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene/allele. Alternatively, the heterologous region can also contain an insertion or one, two, three or of five or fewer nucleotides. Alternatively, the sequence of the mixed duplex oligonucleotide may differ from the sequence of the target gene/allele only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene/allele, and the converse is applicable when the heterologous region encodes a deletion.

The RNA segments of the mixed duplex oligonucleotides are each a part of a homologous region, i.e., a region that is identical in sequence to a fragment of the target gene, which segments together in some embodiments contain at least 13 RNA-type nucleotides and in some embodiments from 16 to 25 RNA-type nucleotides or yet other embodiments 18-22 RNA-type nucleotides or in some embodiments 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the methods and compositions of the present disclosure, a gene repair oligonucleobase (GRON) is a single stranded oligodeoxynucleotide mutational vector (SSOMV), such as disclosed in International Patent Application PCT/USOO/23457, U.S. Pat. Nos. 6,271, 360, 6,479,292, and 7,060,500 which is incorporated by reference in its entirety. The sequence of the SSOMV is based on the same principles as the mutational vectors described in U.S. Pat. Nos. 5,756,325; 5,871,984; 5,760, 012; 5,888,983; 5,795,972; 5,780,296; 5,945,339; 6,004, 804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene. In certain embodiments, a SSOMV does not anneal to itself.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene.

When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSOMVs that encode transversion mutations, i.e., a C or T mutator nucleotide is mismatched, respectively, with a C or T nucleotide in the complementary strand.

2'-OME GRON Design. In various embodiments, a GRON may have both RNA and DNA nucleotides and/or other types of nucleobases. In some embodiments, one or more of the DNA or RNA nucleotides comprise a modification. In certain embodiments, the first 5' nucleotide is an RNA nucleotide and the remainder of the nucleotides are DNA. In still further embodiments, the first 5' RNA nucleotide is modified with a 2-O-Me. In other embodiments, the first two, three, four, five, six, seven, eight, nine, ten or more 5' nucleotides are an RNA nucleotide and the remainder of the nucleotides are DNA. In still further embodiments, one or more of the first two, three, four, five, six, seven, eight, nine, ten or more 5' RNA nucleotide are modified with a 2'-0-Me. In plant cells, double-strand beaks in DNA are typically repaired by the NHEJ DNA repair pathway. This pathway does not require a template to repair the DNA and is therefore error prone. The advantage of using this pathway to repair DNA for a plant cell is that it is quick, ubiquitous and most importantly can occur at times when a cell is not undergoing DNA replication. Another DNA repair pathway that functions in repairing double-strand breaks outside of the replication fork in plant cells is called templated repair; however, unlike the NHEJ pathway this type of repair is precise and requires the use of a DNA template (GRON).

Improving Efficiency

The present disclosure may include any of a number of approaches to increase the effectiveness of conversion of a target gene using repair oligonucleotides, and which may be used alone or in combination with one another. These include, for example:

1. Introducing modifications to the repair oligonucleotides which attract DNA repair machinery to the targeted (mismatch) site.
   A. Introduction of one or more abasic sites in the oligonucleotide (e.g., within 10 bases, and in some embodiments with 5 bases of the desired mismatch site) generates a lesion which is an intermediate in base excision repair (BER), and which attracts BER machinery to the vicinity of the site targeted for conversion by the repair oligonucleotide. dSpacer (abasic furan) modified oligonucleotides may be prepared as described in, for example, Takeshita et al., *J. Biol. Chem.*, 262:10171-79, 1987.
   B. Inclusion of compounds which induce single or double strand breaks, either into the oligonucleotide or together with the oligonucleotide, generates a lesion which is repaired by NHEJ, microhomology-mediated end joining (MMEJ), and homologous recombination. By way of example, the bleomycin family of antibiotics, zinc fingers, FokI (or any type IIS class of restriction enzyme) and other nucleases may be covalently coupled to the 3' or 5' end of repair oligonucleotides, in order to introduce double strand breaks in the vicinity of the site targeted for conversion by the repair oligonucleotide. The bleomycin family of antibiotics are DNA cleaving glycopeptides which include bleomycin, zeocin, phleomycin, tallysomycin, pepleomycin and others.

C. Introduction of one or more 8' oxo dA or dG incorporated in the oligonucleotide (e.g., within 10 bases, and in some embodiments with 5 bases of the desired mismatch site) generates a lesion which is similar to lesions created by reactive oxygen species. These lesions induce the so-called "pushing repair" system. See, e.g., Kim et al., J. Biochem. Mol. Biol. 37:657-62, 2004.

2. Increase stability of the repair oligonucleotides:

Introduction of a reverse base (idC) at the 3' end of the oligonucleotide to create a 3' blocked end on the repair oligonucleotide.

Introduction of one or more 2'O-methyl nucleotides or bases which increase hybridization energy (see, e.g., WO2007/073149) at the 5' and/or 3' of the repair oligonucleotide.

Introduction of one or a plurality of 2'O-methyl RNA nucleotides at the 5' end of the repair oligonucleotide, leading into DNA bases which provide the desired mismatch site, thereby creating an Okazaki Fragment-like nucleic acid structure.

Conjugated (5' or 3') intercalating dyes such as acridine, psoralen, ethidium bromide and Syber stains.

Introduction of a 5' terminus cap such as a T/A clamp, a cholesterol moiety, SIMA (HEX), riboC and amidite.

Backbone modifications such as phosphothioate, 2'-O methyl, methyl phosphonates, locked nucleic acid (LNA), MOE (methoxyethyl), diPS and peptide nucleic acid (PNA).

Crosslinking of the repair oligonucleotide, e.g., with intrastrand crosslinking reagents agents such as cisplatin and mitomycin C.

Conjugation with fluorescent dyes such as Cy3, DY547, Cy3.5, Cy3B, Cy5 and DY647.

3. Increase hybridization energy of the repair oligonucleotide through incorporation of bases which increase hybridization energy (see, e.g., WO2007/073149).

4. Increase the quality of repair oligonucleotide synthesis by using nucleotide multimers (dimers, trimers, tetramers, etc.) as building blocks for synthesis. This results in fewer coupling steps and easier separation of the full length products from building blocks.

5. Use of long repair oligonucleotides (i.e., greater than 55 nucleotides in length, for example such as the lengths described herein, for example having one or more mutations or two or more mutations targeted in the repair oligonucleotide.

Examples of the foregoing approaches are provided in Table A.

TABLE A

Exemplary GRON chemistries.

| | Oligo type | Modifications |
|---|---|---|
| 5' mods | T/A clamp | T/A clamp |
| Backbone modifications | Phosphothioate | PS |
| Intercalating dyes | 5' Acridine 3' | idC Acridine, idC |
| 2'-O-methyl | | DNA/RNA |
| Cy3 replacements | | DY547 |
| Facilitators | 2'-O-Me oligos designed 5' and 3' of the converting oligo | 2'-O-Me |
| Abasic | Abasic site placed in various locations 5' and 3' to the converting base. 44 mer | Abasic 2 |

58

TABLE A-continued

Exemplary GRON chemistries.

| | Oligo type | Modifications |
|---|---|---|
| Assist | Assist approach Overlap: 2 oligos: 1 with Cy3/idC, 1 unmodified repair oligo | Cy3, idC on one, none on the other: |
| Assist | Assist approach No overlap: 2 oligos: 1 with Cy3/idC, 1 unmodified repair oligo | only make the unmodified oligo |
| Abasic | THF site placed in various locations 5' and 3' to the converting base. 44 mer | Tetrahydrofuran (dspacer) |
| Backbone modifications | 9 | 2'-O-Me |
| Trimers | | Trimer amidites, Cy3. idC |
| Pushing repair | | 8'oxo dA, 5' Cy3, idC |
| Pushing repair | | 8'oxo dA, 5' Cy3, idC |
| Double Strand Break | | Bleomycin |
| Crosslinker | | Cisplatin |
| Crosslinker | | Mitomycin C |
| Facilitators | super bases 5' and 3' of converting oligo | 2 amino dA and 2-thio T |
| Super oligos | | 2'amino d, 5' Cy3, idC |
| Super oligos | | 2-thio T, 5' Cy3, idC |
| Super oligos | | 7-deaza A, 5' Cy3, idC |
| Super oligos | | 7-deaza G, 5' Cy3, idC |
| Super oligos | | propanyl dC, 5' Cy3, idC |
| Intercalating dyes | 5' Psoralen/3' idC | Psoralen, idC |
| Intercalating dyes | 5' Ethidium bromide | Ethidium bromide |
| Intercalating dyes | 5' Syber stains | Syber stains |
| 5' mods | 5' Chol/3' idC | Cholesterol |
| Double mutation | Long oligo (55+ bases) w/ 2 mutation | Any modification |
| 5' mods | 5' SIMA HEX/3'idC | SIMA HEX, idC |
| Backbone modifications | 9 | Methyl phosphonates |
| Backbone modifications | | LNA |
| Backbone modifications | 1 | MOE (methoxyethyl) |
| Cy3 replacements | | Cy3.5 |
| Cy3 replacements | | Cy5 |
| Backbone modifications | | diPS |
| 5' mods | | riboC for branch nm |
| Backbone modifications | | PNA |
| Cy3 replacements | | DY647 |
| 5' mods | 5' branch | symmetric branch amidite/idC |

The foregoing modifications may also include known nucleotide modifications such as methylation, 5' intercalating dyes, modifications to the 5' and 3' ends, backbone modifications, crosslinkers, cyclization and 'caps' and substitution of one or more of the naturally occurring nucleotides with an analog such as inosine. Modifications of nucleotides include the addition of acridine, amine, biotin, cascade blue, cholesterol, Cy3@, Cy5@, Cy5.5@ Daboyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S", SE, BODIPY®, Marina Blue@, Pacific Blue@, Oregon Green@, Rhodamine Green@, Rhodamine Red@, Rhodol Green@ and Texas Red@. Polynucleotide backbone modifications include methylphosphonate, 2'-OMe-methylphosphonate RNA, phosphorothiorate, RNA, 2'-OMeRNA. Base modifications include 2-amino-dA, 2-aminopurine, 3'-(ddA), 3'dA (cordycepin), 7-deaza-dA, 8-Br-dA, 8-oxo-dA, N6-Me-dA, abasic site (dSpacer), biotin dT, 2'-OMe-SMe-C, 2'-OMe-propynyl-C, 3'-(5-Me-dC), 3'-(ddC), 5-Br-dC, 5-1-duc, 5-Me-dC, 5-F-dC, carboxy-dT, convertible dC, convertible dA, convertible dG, convertible dT, convertible dU, 7-deaza-dG, 8-Br-dG, 8-oxo-dG, 06-Me-dG, S6-DNP-dG, 4-methyl-indole, 5-nitroindole, 2'-OMe-inosine, 2'-dI, o6-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, 04-Me-dT, 04-triazol dT, 2'-OMe-propynyl-U, 5-Br-dU, 2'-dU, 5-F-dU, 5-1-dU, 04-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

Oligonucleobases may have nick(s), gap(s), modified nucleotides such as modified oligonucleotide backbones, abasic nucleotides, or other chemical moieties. In a further embodiment, at least one strand of the oligonucleobase includes at least one additional modified nucleotide, e.g., a 2'-O-methyl modified nucleotide such as a MOE (methoxyethyl), a nucleotide having a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide (the nucleobase is missing or has a hydroxyl group in place thereof (see, e.g., Glen Research, http://www.glenresearch-.com/GlenReports/GR21-14.html)), a 2'-amino-modified nucleotide, a 2'-alkyl-modified nucleotide, a morpholino nucleotide, a phosphoramidite, and a non-natural base comprising nucleotide. Various salts, mixed salts and free acid forms are also included.

Preferred modified oligonucleotide backbones include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3 '-amino phosphoramidate and aminoalkylphosphoramidates, thionophosphoramidates, thionoalkyl-phosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). The most common use of a linkage inversion is to add a 3'-3' linkage to the end of an antisense oligonucleotide with a phosphorothioate backbone. The 3'-3' linkage further stabilizes the antisense oligonucleotide to exonuclease degradation by creating an oligonucleotide with two 5'-OH ends and no 3'-OH end. Linkage inversions can be introduced into specific locations during oligonucleotide synthesis through use of "reversed phosphoramidites". These reagents have the phosphoramidite groups on the 5'-OH position and the dimethoxytrityl (DMT) protecting group on the 3'-OH position. Normally, the DMT protecting group is on the 5'-OH and the phosphoramidite is on the 3'-OH.

Examples of modified bases include, but are not limited to, 2-aminopurine, 2'-amino-butyryl pyrene-uridine, 2'-aminouridine, 2'-deoxyuridine, 2'-fluoro-cytidine, 2'-fluoro-uridine, 2,6-diaminopurine, 4-thio-uridine, 5-bromo-uridine, 5-fluoro-cytidine, 5-fluorouridine, 5-indo-uridine, 5-methylcytidine, inosine, N3-methyl-uridine, 7-deaza-guanine, 8-aminohexyl-amino-adenine, 6-thio-guanine, 4-thio-thymine, 2-thio-thymine, 5-iodo-uridine, 5-iodo-cytidine, 8-bromo-guanine, 8-bromo-adenine, 7-deaza-adenine, 7-diaza-guanine, 8-oxo-guanine, 5,6-dihydro-uridine, and 5-hydroxymethyl-uridine. These synthetic units are commercially available; (for example, purchased from Glen Research Company) and can be incorporated into DNA by chemical synthesis.

Examples of modification of the sugar moiety are 3'-deoxylation, 2'-fluorination, and arabanosidation, however, it is not to be construed as being limited thereto. Incorporation of these into DNA is also possible by chemical synthesis.

Examples of the 5' end modification are 5'-amination, 5'-biotinylation, 5'-fluoresceinylation, 5'-tetrafluoro-fluoreceinyaltion, 5'-thionation, and 5'-dabsylation, however it is not to be construed as being limited thereto.

Examples of the 3' end modification are 3'-amination, 3'-biotinylation, 2,3-dideoxidation, 3'-thionation, 3'-dabsylation, 3'-carboxylation, and 3'-cholesterylation, however, it is not to be construed as being limited thereto.

In one preferred embodiment, the oligonucleobase can contain a 5' blocking substituent that is attached to the 5' terminal carbons through a linker. The chemistry of the linker is not critical other than its length, which should in some embodiments be at least 6 atoms long and that the linker should be flexible. A variety of non-toxic substituents such as biotin, cholesterol or other steroids or a non-intercalating cationic fluorescent dye can be used. Particularly preferred reagents to make oligonucleobases are the reagents sold as Cy3™ and Cy5™ by Glen Research, Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is particularly preferred. When the indocarbocyanine is N-oxyalkyl substituted it can be conveniently linked to the 5' terminal of the oligodeoxynucleotide as a phosphodiester with a 5' terminal phosphate. When the commercially available Cy3 phosphoramidite is used as directed, the resulting 5' modification consists of a blocking substituent and linker together which are a N-hydroxypropyl, N'-phosphatidylpropyl 3,3,3',3'-tetramethyl indomonocarbocyanine. Other dyes contemplated include Rhodamine6G, Tetramethylrhodamine, Sulforhodamine 101, Merocyanine 540, Atto565, Atto550 26, Cy3.5, Dy547, Dy548, Dy549, Dy554, Dy555, Dy556, Dy560, mStrawberry and mCherry.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical.

The oligo designs herein described might also be used as more efficient donor templates in combination with other DNA editing or recombination technologies including, but not limited to, gene targeting using site-specific homologous recombination by zinc finger nucleases, meganucleases, Transcription Activator-Like Effector Nucleases (TALENs) or Clustered Regularly Interspaced Short Palindromic Repeats (CRISPRs).

The present disclosure in certain aspects and embodiments may include methods and compositions relating to methods for the efficient modification of genomic cellular DNA and/or recombination of DNA into the genomic DNA of cells. Although not limited to any particular use, some methods provided herein may in certain embodiments be useful in, for example, introducing a modification into the genome of a cell for the purpose of determining the effect of the modification on the cell. For example, a modification may be introduced into the nucleotide sequence which encodes an enzyme to determine whether the modification alters the enzymatic activity of the enzyme, and/or determine the location of the enzyme's catalytic region. Alternatively, the modification may be introduced into the coding sequence of a DNA-binding protein to determine whether the DNA binding activity of the protein is altered, and thus to delineate the particular DNA-binding region within the protein. Yet another alternative is to introduce a modification into a non-coding regulatory sequence (e.g., promoter, enhancer, regulatory RNA sequence (miRNA), etc.) in order to determine the effect of the modification on the level of expression of a second sequence which is operably linked to the non-coding regulatory sequence. This may be desirable to, for example, define the particular sequence which possesses regulatory activity.

DNA Cutters

One strategy for producing targeted gene disruption is through the generation of single strand or double strand DNA breaks using a DNA cutter such as a site-specific endonuclease. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

Certain aspects of the present disclosure related to introducing one or more mutations into a targeted nucleic acid using a DNA endonuclease. In some embodiments, the DNA endonuclease is an RNA-guided DNA endonuclease. Exemplary RNA-guided DNA endonucleases include Cas9, Cpf1, and the like. RNA-guided DNA endonucleases suitable for use in the methods and compositions described herein will be readily apparent to one of skill in the art. Additional DNA endonucleases for use in the methods and compositions of the present disclosure are described herein.

Zinc Fingers

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. As FokI endonuclease cleaves as a dimer, one strategy to prevent off-target cleavage events has been to design zinc finger domains that bind at adjacent 9 base pair sites. See also U.S. Pat. Nos. 7,285,416; 7,521,241; 7,361, 635; 7,273,923; 7,262,054; 7,220,719; 7,070,934; 7,013, 219; 6,979,539; 6,933,113; 6,824,978; each of which is hereby herein incorporated by reference in its entirety.

TALENs

TALENs are targetable nucleases are used to induce single- and double-strand breaks into specific DNA sites, which are then repaired by mechanisms that can be exploited to create sequence alterations at the cleavage site.

The fundamental building block that is used to engineer the DNA-binding region of TALENS is a highly conserved repeat domain derived from naturally occurring TALEs encoded by *Xanthomonas* spp. proteobacteria. DNA binding by a TALEN is mediated by arrays of highly conserved 33-35 amino acid repeats that are flanked by additional TALE-derived domains at the amino-terminal and carboxy-terminal ends of the repeats.

These TALE repeats specifically bind to a single base of DNA, the identity of which is determined by two hyper-variable residues typically found at positions 12 and 13 of the repeat, with the number of repeats in an array corresponded to the length of the desired target nucleic acid, the identity of the repeat selected to match the target nucleic acid sequence. In some embodiments, the target nucleic acid is between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al., Nucleic Acids Res. 2011 July; 39(12): e82.

Once designed to match the desired target sequence, TALENs can be expressed recombinantly and introduced into protoplasts as exogenous proteins, or expressed from a plasmid within the protoplast or administered as mRNA or as protein.

Meganucleases

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease. See e.g., U.S. Pat. Nos. 8,338,157, and 8,445,251.

CRISPRs or CRISPR/Cas Systems

CRISPR-Cas system contains three basic design components: 1) Cas gene, transcript (e.g., mRNA) or protein; 2) guide RNA (gRNA); and 3) crRNAs (CRISPR RNA) are RNA segments processed from RNA transcripts encoding the CRISPR repeat arrays, which harbor a "protospacer" region that are complementary to a foreign DNA site (e.g., endogenous DNA target region) and a part of the CRISPR repeat. See e.g., PCT Application Nos WO/2014/093661 and WO/2013/176772.

Cas (CRISPR Associated) Gene, Transcript (e.g., mRNA) or Protein

Transient Cas expression from a plasmid vector, direct delivery of Cas protein and or direct delivery of Cas mRNA into plant cells. Cas genes are codon optimized for expression in higher plants, algae or yeast and are driven by either a constitutive, inducible, tissue-specific or species-specific promoter when applicable. Cas transcript termination and polyadenlyation signals are either NosT, RBCT, HSP18.2T or other gene specific or species—specific terminators. Cas gene cassettes may contain introns, either native or in combination with gene-specific promoters and or synthetic promoters. Cas protein may contain one or more nuclear localization signal sequences (NLS), mutations, deletions, alterations or truncations. In transient expression systems, Cas gene cassettes may be combined with other components of the CRISPR-Cas system such as gRNA cassettes on the same transient expression vector. Alternatively, Cas gene cassettes may be located and expressed from constructs independent of gRNA cassettes or from other components of the CRISPR-Cas system. CRISPR associated (Cas) gene—encode for proteins with a variety of predicted nucleic acid-manipulating activities such as nucleases, helicases and polymerase. Cas genes include Cas9. Cas9 is a gene encoding a large protein containing a predicted RuvC-like and HNH endonuclease domains and is associated with the CRISPR adaptive immunity system that is present in most archaea and many bacteria. Cas9 protein consists of two lobes:

1) Recognition (REC) lobe—consists of three domains:
   a) BH (bridge helix)
   b) REC1—facilitates RNA-guided DNA targeting
   c) REC2—facilitates RNA-guided DNA targeting
2) Nuclease (NUC) lobe—consists of three domains:
   a) RuvC—facilitates RNA-guided DNA targeting; endonuclease activity
   b) HNH—endonuclease activity
   c) PI—PAM interacting In other embodiments, the Cas gene may be a homolog of Cas9 in which the RuvC, HNH, REC and BH domains are highly conserved. In some embodiments, Cas genes are those from the following species listed in Table B.

TABLE B

| Exemplary Cas Genes | | | |
|---|---|---|---|
| Locus ID/GI | Species | Cas profile ID | Cas gene |
| 352684361 | Acidaminococcus__intestini__RyC__MR95__uid74445 | mkCas0193 | cas9 |
| 117929158 | Acidothermus__cellulolyticus__11B__uid58501 | cd09643 | cas9 |
| 326315085 | Acidovorax__avenae__ATCC__19860__uid42497 | cd09643 | cas9 |
| 222109285 | Acidovorax__ebreus__TPSY__uid59233 | COG3513 | cas9 |
| 152978060 | Actinobacillus__succinogenes__130Z__uid58247 | COG3513 | cas9 |
| 407692091 | Actinobacillus__suis__H91__0380__uid176363 | COG3513 | cas9 |
| 187736489 | Akkermansia__muciniphila__ATCC__BAA__835__uid58985 | cd09643 | cas9 |
| 319760940 | Alicycliphilus__denitrificans__BC__uid49953 | cd09643 | cas9 |
| 330822845 | Alicycliphilus__denitrificans__K601__uid66307 | cd09643 | cas9 |
| 288957741 | Azospirillum__B510__uid46085 | cd09643 | cas9 |
| 549484339 | Bacteroides__CF50__uid222805 | cd09643, COG3513 | cas9 |
| 375360193 | Bacteroides__fragilis__638R__uid84217 | COG3513, COG3513 | cas9 |
| 60683389 | Bacteroides__fragilis__NCTC__9343__uid57639 | COG3513, COG3513 | cas9 |
| 471261880 | Bdellovibrio__exovorus__JSS__uid194119 | COG3513 | cas9 |
| 390944707 | Belliella__baltica__DSM__15883__uid168182 | cd09643, COG3513 | cas9 |
| 470166767 | Bibersteinia__trehalosi__192__uid193709 | COG3513 | cas9 |
| 310286728 | Bifidobacterium__bifidum__S17__uid59545 | mkCas0193 | cas9 |
| 283456135 | Bifidobacterium__dentium__Bd1__uid43091 | cd09643 | cas9 |
| 189440764 | Bifidobacterium__longum__DJO10A__uid58833 | cd09643 | cas9 |
| 384200944 | Bifidobacterium__longum__KACC__91563__uid158861 | cd09643 | cas9 |
| 479188345 | Butyrivibrio__fibrisolvens__uid197155 | cd09643 | cas9 |
| 544063172 | Campylobacter__jejuni__00__2425__uid219359 | COG3513 | cas9 |
| 543948719 | Campylobacter__jejuni__00__2426__uid219324 | COG3513 | cas9 |
| 543946932 | Campylobacter__jejuni__00__2538__uid219325 | COG3513 | cas9 |
| 543950499 | Campylobacter__jejuni__00__2544__uid219326 | COG3513 | cas9 |
| 549693479 | Campylobacter__jejuni__4031__uid222817 | COG3513 | cas9 |
| 157415744 | Campylobacter__jejuni__81116__uid58771 | COG3513 | cas9 |
| 384448746 | Campylobacter__jejuni__IA3902__uid159531 | COG3513 | cas9 |
| 384442102 | Campylobacter__jejuni__M1__uid159535 | COG3513 | cas9 |
| 384442103 | Campylobacter__jejuni__M1__uid159535 | COG3513 | cas9 |
| 403056243 | Campylobacter__jejuni__NCTC__11168__BN148__uid174152 | COG3513 | cas9 |
| 218563121 | Campylobacter__jejuni__NCTC__11168__ATCC__700819__uid57587 | COG3513 | cas9 |
| 407942868 | Campylobacter__jejuni__PT14__uid176499 | COG3513 | cas9 |
| 153952471 | Campylobacter__jejuni__doylei__269__97__uid58671 | COG3513 | cas9 |
| 294086111 | Candidatus__Puniceispirillum__marinum__IMCC1322__uid47081 | cd09643 | cas9 |
| 340622236 | Capnocytophaga__canimorsus__Cc5__uid70727 | COG3513, cd09643 | cas9 |
| 220930482 | Clostridium__cellulolyticum__H10__uid58709 | COG3513 | cas9 |
| 479136975 | Coprococcus__catus__GD__7__uid197174 | mkCas0193 | cas9 |
| 328956315 | Coriobacterium__glomerans__PW2__uid65787 | mkCas0193 | cas9 |
| 375289763 | Corynebacterium__diphtheriae__241__uid83607 | cd09643 | cas9 |
| 376283539 | Corynebacterium__diphtheriae__31A__uid84309 | cd09643 | cas9 |
| 376286566 | Corynebacterium__diphtheriae__BH8__uid84311 | cd09643 | cas9 |
| 376289243 | Corynebacterium__diphtheriae__C7__beta__uid84313 | cd09643 | cas9 |
| 376244596 | Corynebacterium__diphtheriae__HC01__uid84297 | cd09643 | cas9 |
| 376292154 | Corynebacterium__diphtheriae__HC02__uid84317 | cd09643 | cas9 |
| 38232678 | Corynebacterium__diphtheriae__NCTC__13129__uid57691 | cd09643 | cas9 |
| 376256051 | Corynebacterium__diphtheriae__VA01__uid84305 | cd09643 | cas9 |
| 159042956 | Dinoroseobacter__shibae__DFL__12__uid58707 | cd09643 | cas9 |
| 339445983 | Eggerthella__YY7918__uid68707 | mkCas0193 | cas9 |
| 187250660 | Elusimicrobium__minutum__Pei191__uid58949 | cd09643 | cas9 |
| 479180325 | Enterococcus__7L76__uid197170 | cd09643 | cas9 |
| 397699066 | Enterococcus__faecalis__D32__uid171261 | mkCas0193 | cas9 |
| 384512368 | Enterococcus__faecalis__OG1RF__uid54927 | mkCas0193 | cas9 |

TABLE B-continued

Exemplary Cas Genes

| Locus ID/GI | Species | Cas profile ID | Cas gene |
|---|---|---|---|
| 392988474 | Enterococcus__hirae__ATCC__9790__uid70619 | mkCas0193 | cas9 |
| 558685081 | Enterococcus__mundtii__QU__25__uid229420 | mkCas0193 | cas9 |
| 238924075 | Eubacterium__rectale__ATCC__33656__uid59169 | cd09643 | cas9 |
| 385789535 | Fibrobacter__succinogenes__S85__uid161919 | cd09643, cd09643 | cas9 |
| 261414553 | Fibrobacter__succinogenes__S85__uid41169 | cd09643, cd09643 | cas9 |
| 374307738 | Filifactor__alocis__ATCC__35896__uid46625 | mkCas0193 | cas9 |
| 169823755 | Finegoldia__magna__ATCC__29328__uid58867 | mkCas0193 | cas9 |
| 150025575 | Flavobacterium__psychrophilum__JIP02__86__uid61627 | cd09643, cd09643 | cas9 |
| 327405121 | Fluviicola__taffensis__DSM__16823__uid65271 | cd09643, cd09643 | cas9 |
| 387824704 | Francisella__cf__novicida__3523__uid162107 | cd09704 | cas9 |
| 118497352 | Francisella__novicida__U112__uid58499 | cd09704 | cas9 |
| 134302318 | Francisella__tularensis__WY96__3418__uid58811 | cd09704 | cas9 |
| 89256630 | Francisella__tularensis__holarctica__LVS__uid58595 | cd09704 | cas9 |
| 89256631 | Francisella__tularensis__holarctica__LVS__uid58595 | cd09704 | cas9 |
| 534508854 | Fusobacterium__3__1__36A2__uid55995 | mkCas0193 | cas9 |
| 530600688 | Geobacillus__JF8__uid215234 | COG3513 | cas9 |
| 209542524 | Gluconacetobacter__diazotrophicus__PA1__5__uid59075 | COG3513 | cas9 |
| 162147907 | Gluconacetobacter__diazotrophicus__PA1__5__uid61587 | COG3513 | cas9 |
| 479173968 | Gordonibacter__pamelaeae__7__10__1__b__uid197167 | mkCas0193 | cas9 |
| 345430422 | Haemophilus__parainfluenzae__T3T1__uid72801 | COG3513 | cas9 |
| 471315929 | Helicobacter__cinaedi__ATCC__BAA__847__uid193765 | COG3513 | cas9 |
| 386762035 | Helicobacter__cinaedi__PAGU611__uid162219 | COG3513 | cas9 |
| 291276265 | Helicobacter__mustelae__12198__uid46647 | COG3513 | cas9 |
| 385811609 | Ignavibacterium__album__JCM__16511__uid162097 | cd09643, COG3513 | cas9 |
| 310780384 | Ilyobacter__polytropus__DSM__2926__uid59769 | COG3513 | cas9 |
| 331702228 | Lactobacillus__buchneri__NRRL__B__30929__uid66205 | mkCas0193 | cas9 |
| 406027703 | Lactobacillus__buchneri__uid73657 | mkCas0193 | cas9 |
| 385824065 | Lactobacillus__casei__BD__II__uid162119 | mkCas0193 | cas9 |
| 191639137 | Lactobacillus__casei__BL23__uid59237 | mkCas0193 | cas9 |
| 385820880 | Lactobacillus__casei__LC2W__uid162121 | mkCas0193 | cas9 |
| 523514789 | Lactobacillus__casei__LOCK919__uid210959 | mkCas0193 | cas9 |
| 409997999 | Lactobacillus__casei__W56__uid178736 | mkCas0193 | cas9 |
| 301067199 | Lactobacillus__casei__Zhang__uid50673 | mkCas0193 | cas9 |
| 385815562 | Lactobacillus__delbrueckii__bulgaricus__2038__uid161929 | mkCas0193 | cas9 |
| 385815563 | Lactobacillus__delbrueckii__bulgaricus__2038__uid161929 | mkCas0193 | cas9 |
| 385815564 | Lactobacillus__delbrueckii__bulgaricus__2038__uid161929 | mkCas0193 | cas9 |
| 385826041 | Lactobacillus__johnsonii__DPC__6026__uid162057 | mkCas0193 | cas9 |
| 532357525 | Lactobacillus__paracasei__8700__2__uid55295 | mkCas0193 | cas9 |
| 448819853 | Lactobacillus__plantarum__ZJ316__uid188689 | mkCas0193 | cas9 |
| 385828839 | Lactobacillus__rhamnosus__GG__uid161983 | mkCas0193 | cas9 |
| 258509199 | Lactobacillus__rhamnosus__GG__uid59313 | mkCas0193 | cas9 |
| 523517690 | Lactobacillus__rhamnosus__LOCK900__uid210957 | mkCas0193 | cas9 |
| 385839898 | Lactobacillus__salivarius__CECT__5713__uid162005 | mkCas0193 | cas9 |
| 385839899 | Lactobacillus__salivarius__CECT__5713__uid162005 | mkCas0193 | cas9 |
| 385839900 | Lactobacillus__salivarius__CECT__5713__uid162005 | mkCas0193 | cas9 |
| 90961083 | Lactobacillus__salivarius__UCC118__uid58233 | mkCas0193 | cas9 |
| 90961084 | Lactobacillus__salivarius__UCC118__uid58233 | mkCas0193 | cas9 |
| 347534532 | Lactobacillus__sanfranciscensis__TMW__1__1304__uid72937 | mkCas0193 | cas9 |
| 54296138 | Legionella__pneumophila__Paris__uid58211 | cd09704 | cas9 |
| 406600271 | Leuconostoc__gelidum__JB7__uid175682 | mkCas0193 | cas9 |
| 16801805 | Listeria__innocua__Clip11262__uid61567 | cd09643, COG3513 | cas9 |
| 386044902 | Listeria__monocytogenes__10403S__uid54461 | COG3513, COG3513 | cas9 |
| 550898770 | Listeria__monocytogenes__EGD__uid223288 | COG3513, COG3513 | cas9 |
| 386048324 | Listeria__monocytogenes__J0161__uid54459 | COG3513, COG3513 | cas9 |
| 405756714 | Listeria__monocytogenes__SLCC2540__uid175106 | COG3513, COG3513 | cas9 |
| 404411844 | Listeria__monocytogenes__SLCC5850__uid175110 | COG3513, COG3513 | cas9 |
| 404282159 | Listeria__monocytogenes__serotype__1__2b__SLCC2755__uid52455 | COG3513, COG3513 | cas9 |
| 404287973 | Listeria__monocytogenes__serotype__7__SLCC2482__uid174871 | COG3513, COG3513 | cas9 |
| 433625054 | Mycoplasma__cynos__C142__uid184824 | cd09643 | cas9 |
| 401771107 | Mycoplasma__gallisepticum__CA06__2006__052__5__2P__uid172630 | cd09643 | cas9 |
| 385326554 | Mycoplasma__gallisepticum__F__uid162001 | cd09643 | cas9 |
| 401767318 | Mycoplasma__gallisepticum__NC95__13295__2__2P__uid172625 | cd09643 | cas9 |
| 401768090 | Mycoplasma__gallisepticum__NC96__1596__4__2P__uid172626 | cd09643 | cas9 |
| 401768851 | Mycoplasma__gallisepticum__NY01__2001__047__5__1P__uid172627 | cd09643 | cas9 |
| 385325798 | Mycoplasma__gallisepticum__R__high__uid161999 | cd09643 | cas9 |
| 294660600 | Mycoplasma__gallisepticum__R__low__uid57993 | cd09643 | cas9 |
| 565627373 | Mycoplasma__gallisepticum__S6__uid200523 | cd09643 | cas9 |
| 401769598 | Mycoplasma__gallisepticum__WI01__2001__043__13__2P__uid172628 | cd09643 | cas9 |
| 47458868 | Mycoplasma__mobile__163K__uid58077 | cd09643 | cas9 |
| 71894592 | Mycoplasma__synoviae__53__uid58061 | cd09643 | cas9 |
| 313669044 | Neisseria__lactamica__020__06__uid60851 | COG3513 | cas9 |
| 161869390 | Neisseria__meningitidis__053442__uid58587 | COG3513 | cas9 |
| 385324780 | Neisseria__meningitidis__8013__uid161967 | COG3513 | cas9 |
| 385337435 | Neisseria__meningitidis__WUE__2594__uid162093 | COG3513 | cas9 |
| 218767588 | Neisseria__meningitidis__Z2491__uid57819 | COG3513 | cas9 |
| 254804356 | Neisseria__meningitidis__alpha14__uid61649 | COG3513 | cas9 |

TABLE B-continued

Exemplary Cas Genes

| Locus ID/GI | Species | Cas profile ID | Cas gene |
|---|---|---|---|
| 319957206 | Nitratifractor_salsuginis_DSM_16511_uid62183 | cd09643 | cas9 |
| 325983496 | Nitrosomonas_AL212_uid55727 | COG3513 | cas9 |
| 302336020 | Olsenella_uli_DSM_7084_uid51367 | mkCas0193 | cas9 |
| 392391493 | Ornithobacterium_rhinotracheale_DSM_15997_uid168256 | cd09643 | cas9 |
| 154250555 | Parvibaculum_lavamentivorans_DS_1_uid58739 | cd09643 | cas9 |
| 15602992 | Pasteurella_multocida_Pm70_uid57627 | COG3513 | cas9 |
| 557607382 | Pediococcus_pentosaceus_SL4_uid227215 | mkCas0193 | cas9 |
| 294674019 | Prevotella_ruminicola_23_uid47507 | COG3513 | cas9 |
| 408489713 | Psychroflexus_torquis_ATCC_700755_uid54205 | cd09643, cd09643 | cas9 |
| 90425961 | Rhodopseudomonas_palustris_BisB_18_uid58443 | COG3513 | cas9 |
| 91975509 | Rhodopseudomonas_palustris_BisB5_uid58441 | COG3513 | cas9 |
| 83591793 | Rhodospirillum_rubrum_ATCC_11170_uid57655 | cd09643 | cas9 |
| 386348484 | Rhodospirillum_rubrum_F11_uidl62149 | cd09643 | cas9 |
| 383485594 | Riemerella_anatipestifer_ATCC_11845_DSM_15868_uid159857 | COG3513, cd09643 | cas9 |
| 407451859 | Riemerella_anatipestifer_RA_CH_1_uid175469 | COG3513, cd09643 | cas9 |
| 442314523 | Riemerella_anatipestifer_RA_CH_2_uid186548 | COG3513, cd09643 | cas9 |
| 386321727 | Riemerella_anatipestifer_RA_GD_uid162013 | COG3513, cd09643 | cas9 |
| 479204792 | Roseburia_intestinalis_uid197164 | COG3513 | cas9 |
| 470213512 | Sphingomonas_MM_1_uid193771 | COG3513 | cas9 |
| 325972003 | Spirochaeta_Buddy_uid63633 | cd09643 | cas9 |
| 563693590 | Spiroplasma_apis_B31_uid230613 | cd09643 | cas9 |
| 507384108 | Spiroplasma_syrphidicola_EA_1_uid205054 | cd09643 | cas9 |
| 556591142 | Staphylococcus_pasteuri_SP1_uid226267 | cd09643 | cas9 |
| 386318630 | Staphylococcus_pseudintermedius_ED99_uid162109 | mkCas0193 | cas9 |
| 269123826 | Streptobacillus_moniliformis_DSM_12112_uid41863 | COG3513 | cas9 |
| 552737657 | Streptococcus_I_G2_uid224251 | cd09643 | cas9 |
| 512539130 | Streptococcus_agalactiae_09mas018883_uid208674 | mkCas0193 | cas9 |
| 22537057 | Streptococcus_agalactiae_2603V_R_uid57943 | mkCas0193 | cas9 |
| 494703075 | Streptococcus_agalactiae_2_22_uid202215 | mkCas0193 | cas9 |
| 76788458 | Streptococcus_agalactiae_A909_uid57935 | mkCas0193 | cas9 |
| 406709383 | Streptococcus_agalactiae_GD201008_001_uid175780 | mkCas0193 | cas9 |
| 512544670 | Streptococcus_agalactiae_ILRI005_uid208676 | mkCas0193 | cas9 |
| 512698372 | Streptococcus_agalactiae_ILRI112_uid208675 | mkCas0193 | cas9 |
| 25010965 | Streptococcus_agalactiae_NEM316_uid61585 | mkCas0193 | cas9 |
| 410594450 | Streptococcus_agalactiae_SA20_06_uid178722 | mkCas0193 | cas9 |
| 538370328 | Streptococcus_anginosus_C1051_uid218003 | cd09643 | cas9 |
| 410494913 | Streptococcus_dysgalactiae_equisimilis_AC_2713_uid178644 | COG3513 | cas9 |
| 386317166 | Streptococcus_dysgalactiae_equisimilis_ATCC_12394_uid161979 | COG3513 | cas9 |
| 251782637 | Streptococcus_dysgalactiae_equisimilis_GGS_124_uid59103 | COG3513 | cas9 |
| 408401787 | Streptococcus_dysgalactiae_equisimilis_RE378_uid176684 | COG3513 | cas9 |
| 195978435 | Streptococcus_equi_zooepidemicus_MGCS10565_uid59263 | COG3513 | cas9 |
| 386338081 | Streptococcus_gallolyticus_ATCC_43143_uid162103 | cd09643 | cas9 |
| 386338091 | Streptococcus_gallolyticus_ATCC_43143_uid162103 | mkCas0193 | cas9 |
| 325978669 | Streptococcus_gallolyticus_ATCC_BAA_2069_uid63617 | mkCas0193 | cas9 |
| 288905632 | Streptococcus_gallolyticus_UCN34_uid46061 | cd09643 | cas9 |
| 288905639 | Streptococcus_gallolyticus_UCN34_uid46061 | mkCas0193 | cas9 |
| 157150687 | Streptococcus_gordonii_Challis_substr_CH1_uid57667 | cd09643 | cas9 |
| 379705580 | Streptococcus_infantarius_CJ18_uid87033 | mkCas0193 | cas9 |
| 508127396 | Streptococcus_iniae_SF1_uid206041 | mkCas0193 | cas9 |
| 508127399 | Streptococcus_iniae_SF1_uid206041 | COG3513 | cas9 |
| 538379999 | Streptococcus_intermedius_B196_uid218000 | cd09643 | cas9 |
| 527330434 | Streptococcus_lutetiensis_033_uid213397 | mkCas0193 | cas9 |
| 374338350 | Streptococcus_macedonicus_ACA_DC_198_uid81631 | cd09643 | cas9 |
| 397650022 | Streptococcus_mutans_GS_5_uid169223 | mkCas0193 | cas9 |
| 387785882 | Streptococcus_mutans_LJ23_uid162197 | mkCas0193 | cas9 |
| 290580220 | Streptococcus_mutans_NN2025_uid46353 | mkCas0193 | cas9 |
| 24379809 | Streptococcus_mutans_UA159_uid57947 | mkCas0193 | cas9 |
| 336064611 | Streptococcus_pasteurianus_ATCC_43144_uid68019 | cd09643 | cas9 |
| 410680443 | Streptococcus_pyogenes_A20_uid178106 | COG3513 | cas9 |
| 470200927 | Streptococcus_pyogenes_M1_476_uid193766 | COG3513 | cas9 |
| 15675041 | Streptococcus_pyogenes_M1_GAS_uid57845 | COG3513 | cas9 |
| 94990395 | Streptococcus_pyogenes_MGAS10270_uid58571 | COG3513 | cas9 |
| 94994317 | Streptococcus_pyogenes_MGAS10750_uid58575 | COG3513 | cas9 |
| 383479946 | Streptococcus_pyogenes_MGAS15252_uid158037 | COG3513 | cas9 |
| 383493861 | Streptococcus_pyogenes_MGAS_1882_uid158061 | COG3513 | cas9 |
| 94992340 | Streptococcus_pyogenes_MGAS2096_uid58573 | COG3513 | cas9 |
| 21910213 | Streptococcus_pyogenes_MGAS315_uid57911 | COG3513 | cas9 |
| 71910582 | Streptococcus_pyogenes_MGAS5005_uid58337 | COG3513 | cas9 |
| 71903413 | Streptococcus_pyogenes_MGAS6180_uid58335 | COG3513 | cas9 |
| 94988516 | Streptococcus_pyogenes_MGAS9429_uid58569 | COG3513 | cas9 |
| 209559356 | Streptococcus_pyogenes_NZ131_uid59035 | COG3513 | cas9 |
| 28896088 | Streptococcus_pyogenes_SSI_1_uid57895 | COG3513 | cas9 |
| 387783792 | Streptococcus_salivarius_JIM8777_uid162145 | cd09643 | cas9 |
| 386584496 | Streptococcus_suis_D9_uid162125 | cd09643 | cas9 |
| 389856936 | Streptococcus_suis_ST1_uid167482 | mkCas0193 | cas9 |
| 330833104 | Streptococcus_suis_ST3_uid66327 | cd09643 | cas9 |

TABLE B-continued

Exemplary Cas Genes

| Locus ID/GI | Species | Cas profile ID | Cas gene |
|---|---|---|---|
| 55822627 | Streptococcus_thermophilus_CNRZ1066_uid58221 | cd09643 | cas9 |
| 386344353 | Streptococcus_thermophilus_JIM__8232_uid162157 | cd09643 | cas9 |
| 116627542 | Streptococcus_thermophilus_LMD__9_uid58327 | cd09643 | cas9 |
| 116628213 | Streptococcus_thermophilus_LMD__9_uid58327 | mkCas0193 | cas9 |
| 55820735 | Streptococcus_thermophilus_LMG__18311_uid58219 | cd09643 | cas9 |
| 387909441 | Streptococcus_thermophilus_MN_ZLW__002_uid166827 | cd09643 | cas9 |
| 387910220 | Streptococcus_thermophilus_MN_ZLW__002_uid166827 | mkCas0193 | cas9 |
| 386086348 | Streptococcus_thermophilus_ND03_uid162015 | cd09643 | cas9 |
| 386087120 | Streptococcus_thermophilus_ND03_uid162015 | mkCas0193 | cas9 |
| 389874754 | Tistrella__mobilis__KA081020__065_uid167486 | COG3513 | cas9 |
| 42525843 | Treponema__denticola__ATCC__35405_uid57583 | mkCas0193 | cas9 |
| 530892607 | Treponema__pedis__T__A4_uid215715 | COG3513, COG3513 | cas9 |
| 121608211 | Verminephrobacter__eiseniae__EF01__2_uid58675 | cd09643 | cas9 |
| 525888882 | Vibrio__parahaemolyticus__O1__K33__CDC__K4557_uid212977 | COG3513, COG3513 | cas9 |
| 525913263 | Vibrio__parahaemolyticus__O1__K33__CDC__K4557_uid212977 | COG3513 | cas9 |
| 525919586 | Vibrio__parahaemolyticus__O1__K33__CDC__K4557_uid212977 | COG3513, COG3513 | cas9 |
| 525927253 | Vibrio__parahaemolyticus__O1__K33__CDC__K4557_uid212977 | COG3513, COG3513 | cas9 |
| 325955459 | Weeksella__virosa_DSM__16922_uid63627 | cd09643, cd09643 | cas9 |
| 34557790 | Wolinella__succinogenes_DSM__1740_uid61591 | cd09643 | cas9 |
| 34557932 | Wolinella__succinogenes_DSM__1740_uid61591 | cd09704 | cas9 |
| 295136244 | Zunongwangia__profunda__SM__A87_uid48073 | COG3513, cd09643 | cas9 |
| 304313029 | gamma__proteobacterium__HdN1_uid51635 | cd09643 | cas9 |
| 189485058 | uncultured_Termite_group_1_bacterium_phylotype_Rs_D17_uid59059 | cd09643 | cas9 |
| 189485059 | uncultured_Termite_group_1_bacterium_phylotype_Rs_D17_uid59059 | cd09643 | cas9 |
| 189485225 | uncultured_Termite_group_1_bacterium_phylotype_Rs_D17_uid59059 | COG3513 | cas9 |
| 347536497 | Flavobacterium__branchiophilum__FL__15_uid73421 | COG3513, cd09643, COG3513 | cas9, cas9 |
| 365959402 | Flavobacterium__columnare__ATCC__49512_uid80731 | COG3513, cd09643, COG3513 | cas9, cas9 |
| 387132277 | Prevotella__intermedia__17_uid163151 | cd09643, COG3513, COG0188 | cas9, Type IIA topoisomerase |

Guide RNA (gRNA)

gRNA or sgRNA (single guide RNA) is engineered as a fusion between a crRNA and part of the transactivating CRISPR RNA (tracrRNA) sequence, which guides the Cas9 to a specific target DNA sequence that is complementary to the protospacer region. Guide RNA may include an expression cassette containing a chimeric RNA design with a long tracrRNA hybrid, short tracrRNA hybrid or a native CRISPR array+tracrRNA conformation. Chimeric gRNA combines the targeting specificity of the crRNA with the scaffolding properties of the tracrRNA into a single transcript. gRNA transient expression is controlled by species-specific higher plant RNA Polymerase III promoters such as those from the U6 or U3 snRNA gene family (Wang et al., 2008). gRNA transcript termination is controlled by a 6-20 nucleotide tract of poly dT as per Wang et al. (2008). gRNA expression cassettes are located on the same or different transient expression vectors from other components of the CRISPR-Cas system. gRNA transcripts may be synthesized in-vitro and delivered directly into plant cells, independent of or in combination with gRNA transient expression vectors.

In some embodiments, the native S. pyogenes type II CRISPR-Cas system consists of a Crispr ASsociated (Cas9) nuclease and two disparate non-coding RNAs, trans-activating RNA (tracrRNA) and CRISPR RNA (crRNA). The RNA components of this system direct Cas9 nuclease to a sequence specific target in a genome. All three components can be expressed separately as tracrRNA and crRNA and Cas9 protein The crRNA provides the target specificity and consists of a spacer sequence of 20 bases that are complementary to the target DNA (protospacer sequence) that is cleaved by Cas9 (Cong et al., 2013). The tracrRNA acts as an RNA scaffold when associated with crRNA by way of RNA:RNA base pairing and it is this complex that associates with Cas9. The tracrRNA can be engineered to be shorter than 89 bases, as is the case in the Alt-R™ system developed by Integrated DNA Technologies (IDT). In this system tracrRNA as short as 67 bases have increased on-target performance when compare to native tracrRNA. When the crRNA and tracrRNA are artificially combined into a single fused functional RNA or single guide RNA (sgRNA) targeting of Cas9 protein can be greatly simplified over the native system. Similar to the native tracerRNA:crRNA complex, the engineered sgRNA guides the Cas9 to a specific target DNA sequence.

Target Region

Guide RNAs contain two components that define specificity to a DNA target region, a proto-spacer and a proto-spacer adjacent motif (PAM). Proto-spacer sequence, typically 20 nucleotides but can vary based on the DNA target, provides DNA sequence specificity for the CRISPR-Cas complex. DNA targets also contain an NNG or NAG trinucleotide sequence (PAM) where N denotes any nucleotide, immediately 3' or downstream of the proto-spacer.

One Component Approach

Similar to Le Cong et al. (2013) and others, a simplified "one component approach" to CRISPR-Cas gene editing wherein a single transient expression construct contains all components of the CRISPR-Cas complex, i.e. both the gRNA and the Cas expressions cassettes. This allows for an easy modular design for targeting single or multiple loci in any given plant or crop. Targeting multiple loci can be achieved by simply swapping in the target-specific gRNA cassettes. Additionally, species specific promoters, terminators or other expressing enhancing elements can easily be shuttled in and out of "one component approach" transient vectors allowing for optimal expression of both gRNA and Cas protein in a species specific manner.

Two Component Approach

In the two component approach, Cas and gRNA expression cassettes are located on different transient expression vectors. This allows for delivery of a CRISPR-Cas editing components separately, allowing for different ratios of gRNA to Cas within the same cell. Similar to the one component approach, the two component approach also allows for promoters, terminators or other elements affecting expression of CRISPR-Cas components to be easily altered and allow targeting of DNA in a species-specific manner.
Antibiotics Another class of endonucleases are antibiotics which are DNA cleaving glycopeptides such as the bleomycin family of antibiotics are DNA cleaving glycopeptides which include bleomycin, zeocin, phleomycin, tallysomycin, pepleomycin and others which are further described herein.
Other DNA-Modifying Molecules Other DNA-modifying molecules may be used in targeted gene recombination. For example, peptide nucleic acids may be used to induce modifications to the genome of the target cell or cells (see, e.g., Ecker, U.S. Pat. No. 5,986,053 herein incorporated by reference). In brief, synthetic nucleotides comprising, at least, a partial peptide backbone are used to target a homologous genomic nucleotide sequence. Upon binding to the double-helical DNA, or through a mutagen ligated to the peptide nucleic acid, modification of the target DNA sequence and/or recombination is induced to take place. Targeting specificity is determined by the degree of sequence homology between the targeting sequence and the genomic sequence.

In some embodiments of the methods and compositions of the present disclosure genes (such as the FAD2 gene) may be targeted using triple helix forming oligonucleotides (TFO). TFOs may be generated synthetically, for example, by PCR or by use of a gene synthesizer apparatus. Additionally, TFOs may be isolated from genomic DNA if suitable natural sequences are found. TFOs may be used in a number of ways, including, for example, by tethering to a mutagen such as, but not limited to, psoralen or chlorambucil (see, e.g., Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997). Furthermore, for example, TFOs may be tethered to donor duplex DNA (see, e.g., Chan et al., J Biol Chem 272:11541-11548, 1999). TFOs can also act by binding with sufficient affinity to provoke error-prone repair (Wang et al., Science 271:802-805, 1996).

The methods disclosed herein are not necessarily limited to the nature or type of DNA-modifying reagent which is used. For example, such DNA-modifying reagents release radicals which result in DNA strand breakage. Alternatively, the reagents alkylate DNA to form adducts which would block replication and transcription. In another alternative, the reagents generate crosslinks or molecules that inhibit cellular enzymes leading to strand breaks. Examples of DNA-modifying reagents which have been linked to oligonucleotides to form TFOs include, but are not limited to, indolocarbazoles, napthalene diimide (NDI), transplatin, bleomycin, analogues of cyclopropapyrroloindole, and phenanthodihydrodioxins. In particular, indolocarbazoles are topoisomerase I inhibitors. Inhibition of these enzymes results in strand breaks and DNA protein adduct formation (Arimondo et al., Bioorganic and Medicinal Chem. 8, 777, 2000). NDI is a photooxidant that can oxidize guanines which could cause mutations at sites of guanine residues (Nunez, et al., Biochemistry, 39, 6190, 2000). Transplatin has been shown to react with DNA in a triplex target when the TFO is linked to the reagent. This reaction causes the formation of DNA adducts which would be mutagenic (Columbier, et al., Nucleic Acids Research, 24: 4519, 1996). Bleomycin is a DNA breaker, widely used as a radiation mimetic. It has been linked to oligonucleotides and shown to be active as a breaker in that format (Sergeyev, Nucleic Acids Research 23, 4400, 1995; Kane, et al., Biochemistry, 34, 16715, 1995). Analogues of cyclopropapyrroloindole have been linked to TFOs and shown to alkylate DNA in a triplex target sequence. The alkylated DNA would then contain chemical adducts which would be mutagenic (Lukhtanov, et al., Nucleic Acids Research, 25, 5077, 1997). Phenanthodihydrodioxins are masked quinones that release radical species upon photoactivation. They have been linked to TFOs and have been shown to introduce breaks into duplex DNA on photoactivation (Bendinskas et al., Bioconjugate Chem. 9, 555, 1998).

Other methods of inducing modifications and/or recombination are contemplated by the present disclosure. For example, another embodiment involves the induction of homologous recombination between an exogenous DNA fragment and the targeted gene (see e.g., Capecchi et al., Science 244:1288-1292, 1989) or by using peptide nucleic acids (PNA) with affinity for the targeted site. Still other methods include sequence specific DNA recognition and targeting by polyamides (see e.g., Dervan et al., Curr Opin Chem Biol 3:688-693, 1999; Biochemistry 38:2143-2151, 1999) and the use nucleases with site specific activity (e.g., zinc finger proteins, TALENs, Meganucleases and/or CRISPRs).

The present disclosure is not limited to any particular frequency of modification and/or recombination. In some embodiments the methods disclosed herein result in a frequency of modification in the target nucleotide sequence of from 0.01% to 3%. Nonetheless, any frequency (i.e., between 0% and 100%) of modification and/or recombination is contemplated to be within the scope of the present disclosure. The frequency of modification and/or recombination is dependent on the method used to induce the modification and/or recombination, the cell type used, the specific gene targeted and the DNA mutating reagent used, if any. Additionally, the method used to detect the modification and/or recombination, due to limitations in the detection method, may not detect all occurrences of modification and/or recombination. Furthermore, some modification and/or recombination events may be silent, giving no detectable indication that the modification and/or recombination has taken place. The inability to detect silent modification and/or recombination events gives an artificially low estimate of modification and/or recombination. Because of these reasons, and others, the disclosure is not necessarily limited to any particular modification and/or recombination frequency. In one embodiment, the frequency of modification and/or recombination is between 0.01% and 100%. In another embodiment, the frequency of modification and/or recombination is between 0.01% and 50%. In yet another embodiment, the frequency of modification and/or recombination is between 0.1% and 10%. In still yet another embodiment, the frequency of modification and/or recombination is between 0.1% and 5%.

The term "frequency of mutation" as used herein in reference to a population of cells which are treated with a DNA-modifying molecule that is capable of introducing a mutation into a target site in the cells' genome, refers to the number of cells in the treated population which contain the mutation at the target site as compared to the total number of cells which are treated with the DNA-modifying molecule. For example, with respect to a population of cells which is treated with the DNA-modifying molecule TFO tethered to psoralen which is designed to introduce a mutation at a target site in the cells' genome, a frequency of mutation of 5% means that of a total of 100 cells which are treated with TFO-psoralen, 5 cells contain a mutation at the target site.

Although the present disclosure is not necessarily limited to any degree of precision in the modification and/or recombination of DNA in the cell, it is contemplated that some embodiments of the present disclosure require higher degrees of precision, depending on the desired result. For example, the specific sequence changes required for gene repair (e.g., particular base changes) require a higher degree of precision as compared to producing a gene knockout wherein only the disruption of the gene is necessary. With the methods of the present disclosure, achievement of higher levels of precision in modification and/or homologous recombination techniques is greater than with prior art methods.

Delivery of Gene Repair Oligonucleobases into Plant Cells

Any commonly known method used to transform a plant cell can be used for delivering the gene repair oligonucleobases. Illustrative methods are listed below. The methods and compositions herein may involve any of many methods to transfect the cells with the DNA-modifying reagent or reagents. Methods for the introduction of DNA modifying reagents into a cell or cells are well known in the art and include, but are not limited to, microinjection, electroporation, passive adsorption, calcium phosphate-DNA co-precipitation, DEAE-dextran-mediated transfection, polybrene-mediated transfection, liposome fusion, lipofectin, nucleofection, protoplast fusion, retroviral infection, biolistics (i.e., particle bombardment) and the like.

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them.

Specific conditions for using microcarriers in the methods disclosed herein may include the conditions described in International Publication WO 99/07865. In an illustrative technique, ice cold microcarriers (60 mg/ml), mixed duplex oligonucleotide (60 mg/ml) 2.5 M CaCl$_2$ and 0.1 M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 µg/µl microcarriers, 14-17 µg/ml mixed duplex oligonucleotide, 1.1-1.4 M CaCl$_2$ and 18-22 mM spermidine. Optimal results were observed under the conditions of 8 µg/µl microcarriers, 16.5 µg/ml mixed duplex oligonucleotide, 1.3 M CaCl$_2$ and 21 mM spermidine.

Gene repair oligonucleobases can also be introduced into plant cells using microfibers to penetrate the cell wall and cell membrane. U.S. Pat. No. 5,302,523 to Coffee et al. describes the use of silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases for transmutation.

An illustrative technique for microfiber delivery of a gene repair oligonucleobase is as follows: Sterile microfibers (2

µg) are suspended in 150 µl of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 hours as is appropriate for the particular trait.

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al., 1996, in Methods in Molecular Biology 55:89-107, Humana Press, Totowa, N.J.; Kipp et al., 1999, in Methods in Molecular Biology 133: 213-221, Humana Press, Totowa, NJ The protoplasts need not be cultured in growth media prior to electroporation. Illustrative conditions for electroporation are 300,000 protoplasts in a total volume of 0.3 ml with a concentration of gene repair oligonucleobase of between 0.6-4 µg/ml.

In an alternative embodiment, nucleic acids are taken up by plant protoplasts in the presence of the membrane-modifying agent polyethylene glycol, according to techniques well known to those skilled in the art. In another alternative embodiment, the gene repair oligonucleobases can be delivered by injecting it with a microcapillary into plant cells or into protoplasts.

In an alternative embodiment, nucleic acids are embedded in microbeads composed of calcium alginate and taken up by plant protoplasts in the presence of the membrane-modifying agent polyethylene glycol (see, e.g., Sone et al., 2002, Liu et al., 2004).

In an alternative embodiment, nucleic acids frozen in water and introduced into plant cells by bombardment in the form of microparticles (see, e.g., Gilmore, 1991, U.S. Pat. No. 5,219,746; Brinegar et al.).

In an alternative embodiment, nucleic acids attached to nanoparticles are introduced into intact plant cells by incubation of the cells in a suspension containing the nanoparticle (see, e.g., Pasupathy et al., 2008) or by delivering them into intact cells through particle bombardment or into protoplasts by co-incubation (see, e.g., Torney et al., 2007).

In an alternative embodiment, nucleic acids complexed with penetrating peptides and delivered into cells by co-incubation (see, e.g., Chugh et al., 2008, WO 2008148223 A1; Eudes and Chugh).

In an alternative embodiment, nucleic acids are introduced into intact cells through electroporation (see, e.g., He et al., 1998, US 2003/0115641 A1, Dobres et al.).

In an alternative embodiment, nucleic acids are delivered into cells of dry embryos by soaking them in a solution with nucleic acids (see, e.g., Topfer et al., 1989, Senaratna et al., 1991) or in other embodiments are introduced by Cellsqueeze (SQZ Biotech).

Methods of Reducing Polypeptide Activity and Other Mutagenesis Techniques

Certain aspects of the present disclosure relate to reducing levels and/or activity of a polypeptide (e.g. a FAD2 polypeptide). Methods of modifying decreasing the quantity/level or the activity of one or more polypeptides of the present disclosure are well-known in the art and are described herein.

Cells (e.g. plant cells) of the present disclosure may contain one or more polypeptides with decreased activity as compared to a corresponding control cell, such as a wild-type cell. In some embodiments, one or more FAD2 proteins have decreased activity in a host cell as compared to a corresponding control cell. Methods of decreasing the expression, abundance, and/or activity of a polypeptide are well-known in the art and are described herein.

In some embodiments, decreasing the activity of a polypeptide such as, for example, one or more FAD2 proteins involves decreasing the expression of a nucleic acid encoding the polypeptide.

Decreasing the expression of a nucleic acid may be accomplished by introducing a genetic mutation into a target nucleic acid. Mutagenesis approaches may be used to disrupt or "knockout" the expression of a target gene by generating mutations. In some embodiments, the mutagenesis results in a partial deletion of the target gene. In other embodiments, the mutagenesis results in a complete deletion of the target gene. Methods of mutagenizing microorganisms are well known in the art and include, for example, random mutagenesis and site-directed mutagenesis to induce mutations. Examples of methods of random mutagenesis include, for example, chemical mutagenesis (e.g., using ethane methyl sulfonate), insertional mutagenesis, and irradiation.

One method for reducing or inhibiting the expression of a target gene is by genetically modifying the target gene and introducing it into the genome of a host cell to replace the wild-type version of the gene by homologous recombination (for example, as described in U.S. Pat. No. 6,924,146).

Another method for reducing or inhibiting the expression of a target gene is by insertion mutagenesis using the T-DNA of *Agrobacterium tumefaciens*, or transposons (see Winkler et al., Methods Mol. Biol. 82:129-136, 1989, and Martienssen Proc. Natl. Acad. Sci. 95:2021-2026, 1998). After generating the insertion mutants, the mutants can be screened to identify those containing the insertion in a target gene. Methods to disrupt a target gene by insertional mutagenesis are described in for example, U.S. Pat. No. 5,792,633. Methods to disrupt a target gene by transposon mutagenesis are described in for example, U.S. Pat. No. 6,207,384.

A further method to disrupt a target gene is by use of the cre-lox system (for example, as described in U.S. Pat. No. 4,959,317).

Another method to disrupt a target gene is by use of PCR mutagenesis (for example, as described in U.S. Pat. No. 7,501,275).

Endogenous gene expression may also be reduced or inhibited by means of RNA interference (RNAi), which uses a double-stranded RNA having a sequence identical or similar to the sequence of the target gene. RNAi may include the use of micro RNA, such as artificial miRNA, to suppress expression of a gene.

RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA.

Thus, in some embodiments, reduction or inhibition of gene expression is achieved using RNAi techniques. For example, to achieve reduction or inhibition of the expression of a DNA encoding a protein using RNAi, a double-stranded RNA having the sequence of a DNA encoding the protein, or a substantially similar sequence thereof (including those engineered not to translate the protein) or fragment thereof, is introduced into a host cell of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting cells may then be screened for a phenotype associated with the reduced expression of the target gene, e.g., reduced cellulase expression, and/or by monitoring steady-state RNA levels for transcripts of the target gene. Although the sequences used for RNAi need not be completely identical to the target gene, they may be at least 70%, 80%, 90%, 91%, 92%, 93%, 94%, 95%, 96%, 97%, 98%, 99%, or more identical to the target gene sequence. See, e.g., U.S. Patent Application Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Application Publication No. 2003/0221211.

The RNAi nucleic acids may encompass the full-length target RNA or may correspond to a fragment of the target RNA. In some cases, the fragment will have fewer than 100, 200, 300, 400, or 500 nucleotides corresponding to the target sequence. In addition, in some aspects, these fragments are at least, e.g., 50, 100, 150, 200, or more nucleotides in length. Interfering RNAs may be designed based on short duplexes (i.e., short regions of double-stranded sequences). Typically, the short duplex is at least about 15, 20, or 25-50 nucleotides in length (e.g., each complementary sequence of the double stranded RNA is 15-50 nucleotides in length), often about 20-30 nucleotides, e.g., 20, 21, 22, 23, 24, 25, 26, 27, 28, 29, or 30 nucleotides in length. In some cases, fragments for use in RNAi will correspond to regions of a target protein that do not occur in other proteins in the organism or that have little similarity to other transcripts in the organism, e.g., selected by comparison to sequences in analyzing publicly-available sequence databases. Similarly, RNAi fragments may be selected for similarity or identity with a conserved sequence of a gene family of interest, such as those described herein, so that the RNAi targets multiple different gene transcripts containing the conserved sequence.

RNAi may be introduced into a host cell as part of a larger DNA construct. Often, such constructs allow stable expression of the RNAi in cells after introduction, e.g., by integration of the construct into the host genome. Thus, expression vectors that continually express RNAi in cells transfected with the vectors may be employed for this disclosure. For example, vectors that express small hairpin or stem-loop structure RNAs, or precursors to microRNA, which get processed in vivo into small RNAi molecules capable of carrying out gene-specific silencing (Brummelkamp et al, Science 296:550-553, (2002); and Paddison, et al., Genes & Dev. 16:948-958, (2002)) can be used. Post-transcriptional gene silencing by double-stranded RNA is discussed in further detail by Hammond et al., Nature Rev Gen 2: 110-119, (2001); Fire et al., Nature 391: 806-811, (1998); and Timmons and Fire, Nature 395: 854, (1998).

Methods for selection and design of sequences that generate RNAi are well-known in the art (e.g. U.S. Pat. Nos. 6,506,559; 6,511,824; and 6,489,127).

A reduction or inhibition of gene expression in a host cell of a target gene may also be obtained by introducing into host cells antisense constructs based on a target gene nucleic acid sequence. For antisense suppression, a target sequence is arranged in reverse orientation relative to the promoter sequence in the expression vector. The introduced sequence need not be a full length cDNA or gene, and need not be identical to the target cDNA or a gene found in the cell to be transformed. Generally, however, where the introduced sequence is of shorter length, a higher degree of homology to the native target sequence is used to achieve effective antisense suppression. In some aspects, the introduced antisense sequence in the vector will be at least 30 nucleotides in length, and improved antisense suppression will typically be observed as the length of the antisense sequence increases. In some aspects, the length of the antisense sequence in the vector will be greater than 100 nucleotides. Transcription of an antisense construct as described results in the production of RNA molecules that are the reverse complement of mRNA molecules transcribed from an endogenous target gene. Suppression of a target gene expression can also be achieved using a ribozyme. The production and use of ribozymes are disclosed in U.S. Pat. Nos. 4,987,071 and 5,543,508.

Expression cassettes containing nucleic acids that encode target gene expression inhibitors, e.g., an antisense or siRNA, can be constructed using methods well known in the art. Constructs include regulatory elements, including promoters and other sequences for expression and selection of cells that express the construct. Typically, fungal and/or bacterial transformation vectors include one or more cloned coding sequences (genomic or cDNA) under the transcriptional control of 5' and 3' regulatory sequences and a dominant selectable marker. Such transformation vectors typically also contain a promoter (e.g., a regulatory region controlling inducible or constitutive, environmentally- or developmentally-regulated expression), a transcription initiation start site, an RNA processing signal (such as intron splice sites), a transcription termination site, and/or a poly-adenylation signal.

In certain embodiments, a portion of the target nucleic acid may be modified, such as the region encoding the catalytic domain, the coding region, or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification may include, for example, a leader sequence, a propeptide sequence, a signal sequence, a transcription terminator, and a transcriptional activator.

Plants of the Present Disclosure

The methods and compositions described herein may in certain aspects and embodiments be applicable to plants generally. For example, in some aspects and/or embodiments a plant species may be selected from the Brassicaceae family, including a number of important crops such as *Brassica napus* (canola, oilseed rape), *Brassica rapa* (e.g., turnip, Chinese cabbage), *Brassica oleracea* (broccoli, cabbage, cauliflower, etc.), *Brassica juncea* (mustard), *Camelina sativa*, or *Raphanus sativus* (common radish), as well as many important legume crops such as peas, beans, lentils, and soybeans. In some embodiments, plants of the present disclosure are *Brassica napus, Brassica rapa*, or *Brassica juncea* plants, also known as canola. In some embodiments, plants of the present disclosure are *Brassica napus* L. spp. *oleifera*.

According to the present description, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild type FAD2 protein.

According to the present description, substantially normal development of a plant, plant organ, plant tissue or plant cell is defined as the occurrence of one or more developmental events in the plant, plant organ, plant tissue or plant cell that are substantially the same as those occurring in a corresponding plant, plant organ, plant tissue or plant cell expressing the wild type FAD2 protein.

According to the present description plant organs include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants of the present disclosure include those plants that have the potential to produce seed oil with a high oleic acid content. In some embodiments, those plants have the potential to produce seed oil which also has a low linoleic acid content. For example, the present disclosure includes *Brassica* spp. plants that produce seed oil with a high oleic acid content and a low linoleic acid content.

In various embodiments, plants as disclosed herein are principally focused on monocotyledonous plants including any woody plant species that grows as a tree or shrub, any herbaceous species, or any species that produces edible fruits, seeds or vegetables, or any species that produces colorful or aromatic flowers. For example, the plant maybe selected from a species of plant from the group consisting of canola, sunflower, corn, tobacco, sugar beet, cotton, maize, wheat, barley, rice, alfalfa, barley, sorghum, tomato, mango, peach, apple, pear, strawberry, banana, melon, cassava, potato, carrot, lettuce, onion, soy bean, soya spp, sugar cane, pea, chickpea, field pea, fava bean, lentils, turnip, rutabaga, brussel sprouts, lupin, cauliflower, kale, field beans, poplar, pine, eucalyptus, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, lily, and nut producing plants insofar as they are not already specifically mentioned.

Plants and plant cells can be tested for seed oil with a high oleic acid content and a low linoleic acid content using commonly known methods in the art.

In some embodiments, plants of the present disclosure with one or more mutations in one or more FAD2 genes produce seed oil with a high oleic acid content as compared to a corresponding control plant (e.g. a plant of the same species that does not have any mutations in any FAD2 genes, such as a wild-type plant). The oleic acid content in seed oil of plants producing seed oil with a high oleic acid content may be, for example, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% of the total fatty acid content in seed oil. In some embodiments, plants of the present disclosure with one or more mutations in one or more FAD2 genes produce seed oil which further contains low linoleic acid content as compared to a corresponding control plant (e.g. a plant of the same species that does not have any mutations in any FAD2 genes, such as a wild-type plant). The linoleic acid content in seed oil of plants producing seed oil with a low linoleic acid content may be, for example, at most about 20%, at most about 19%, at most about 18%, at most about 17%, at most about 16%, at most about 15%, at most about 14%, at most about 13%, at most about 12%, at most about 11%, at most about 10%, at most about 9%, at most about 8%, at most about 7%, at most about 6%, at most about 5%, at most about 4%, at most about 3%, at most about 2%, at most about 1%, or at most about 0% of the total fatty acid content in seed oil.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type protein of interest.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.
Generation of Plants Tissue culture of various tissues of plant species and regeneration of plants therefrom is known. For example, the propagation of a canola cultivar by tissue culture is described in any of the following but not limited to any of the following: Li et al., "Somatic embryogenesis in quite a direct way in cultures of mesophyll protoplasts of *Brassica napus* L.", Plant Cell Reports 1: 209-211, 1982; Chuong et al., "A Simple Culture Method for *Brassica* hypocotyls Protoplasts," Plant Cell Reports 4:4-6, 1985; Barsby et al., "A Rapid and Efficient Alternative Procedure for the Regeneration of Plants from Hypocotyl Protoplasts of *Brassica napus*," Plant Cell Reports (Spring, 1996); Kartha et al., "In vitro Plant Formation from Stem Explants of Rape," Physiol. Plant, 31:217-220, 1974; Narasimhulu et al., "Species Specific Shoot Regeneration Response of Cotyledonary Explants of Brassicas," Plant Cell Reports (Spring 1988); Sun et al., "Cotyledon-derived diploid and haploid protoplast culture and diploid plant regeneration in *Brassica napus* cv. 'Topas'," Can. J. Bot. 76: 530-541, 1998; Swanson, "Microspore Culture in *Brassica*," Methods in Molecular Biology, Vol. 6, Chapter 17, p. 159, 1990.

Further reproduction of the variety can occur by tissue culture and regeneration. Tissue culture of various tissues of soybeans and regeneration of plants therefrom is well known and widely published. For example, see Komatsuda et al., "Genotype X Sucrose Interactions for Somatic Embryogenesis in Soybeans," Crop Sci. 31:333-337, 1991; Stephens et al., "Agronomic Evaluation of Tissue-Culture-Derived Soybean Plants," Theor. Appl. Genet. 82:633-635, 1991; Komatsuda et al., "Maturation and Germination of Somatic Embryos as Affected by Sucrose and Plant Growth Regulators in Soybeans *Glycine gracilis* Skvortz and *Glycine max* (L.) Merr." Plant Cell, Tissue and Organ Culture, 28:103-113, 1992; Dhir et al., "Regeneration of Fertile Plants from Protoplasts of Soybean (*Glycine max* L. Merr.); Genotypic Differences in Culture Response," Plant Cell Reports 11:285-289, 1992; Pandey et al., "Plant Regeneration from Leaf and Hypocotyl Explants of *Glycine wightii* (W. and A.) VERDC. var. *longicauda*," Japan J. Breed. 42:1-5, 1992; and Shetty et al., "Stimulation of In Vitro Shoot Organogenesis in *Glycine max* (Merrill.) by Allantoin and Amides," Plant Science 81:245-251, 1992. The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference.

Certain aspects of the present disclosure also related to plants derived from plants having one or more mutations in a nucleic acid (e.g. a FAD2 gene) of the present disclosure. For example, plants having one or more FAD2 mutations may be crossed with the same or different plants to give rise to an $F_1$ progeny plant, where at least one of the parents of the $F_1$ progeny plant had the one or more FAD2 mutations. These $F_1$ plants can be further self-crossed or crossed with a different plant line, and resulting $F_2$ progeny can be screened for one or more FAD2 mutations.

EXAMPLES

The following examples are provided to further illustrate aspects of the present disclosure. These examples are non-limiting and should not be construed as limiting any aspect of the present disclosure.

Example 1: Molecular Characterization of FAD2 Genes

Using the publicly available FAD2 cDNA and genomic sequences of *Arabidopsis* FAD2 and those for *Brassica napus*, we designed PCR primers to amplify four BnFAD2 gene sequences from a BN2SU canola line genomic DNA. PCR-amplified FAD2 genomic fragments were cloned and sequenced (BnFAD2-1=SEQ ID NO: 1; BnFAD2-2=SEQ ID NO: 2; BnFAD2-3=SEQ ID NO: 3; BnFAD2-4=SEQ ID NO: 4). Next Generation Sequencing of genomic DNA fragments was performed to complete this analysis. Deduced amino acid sequences of the FAD2 genes isolated from the BN2SU canola line are provided (BnFAD2-1=SEQ ID NO: 5; BnFAD2-2=SEQ ID NO: 6; BnFAD2-3=SEQ ID NO: 7 or SEQ ID NO: 30; BnFAD2-4=SEQ ID NO: 31).

Example 2: Generation of FAD2 Gene Knock-Out Canola Plants Using RTDS™ Technology In this Example RTDS™ reagents used to target BnFAD2 genes in order to generate BnFAD2 loss of function (LOF) lines include a CRISPR/Cas9 protein complexed with gRNAs (RNPs, Table 1), along with single-stranded oligonucleotides (ssODNs) (Table 2). The CRISPR/Cas9 consists of two components: the plant codon-optimized *Streptococcus pyogenes* Cas9 (SpCas9) and sgRNAs that are expressed as protein and RNA respectively. The sgRNA is in vitro transcribed from a DNA template, and it is a fusion of CRISPR RNA (crRNA) and trans-activating crRNA (tracrRNA). The crRNA region contains the spacer sequences described in Table 1, which are used to guide the Cas9 nuclease protein to each of the target FAD2 genes. The ssODNs, also called GRONs (gene repair oligonucleotides) contain the coding sequence of the targeted FAD2 genes around the site of conversion, carry precise gene specific mutations (+1 insertion, −1, and −2 deletions), and are labeled with a 2'-O-Me group at the first 5' base, which is a RNA base instead of a DNA base (Table 2).

RNPs and GRONs are introduced into protoplasts by PEG mediated delivery at a final concentration of 1.0 μg/μl and 0.05 μM, respectively (SOP CB2016-2). Before delivery to protoplasts, the recombinant Cas9 protein is complexed in vitro with the gRNA. Canola protoplasts are isolated from leaves of in vitro micropropagated plants, following our standard protocol (SOPs CB2014-1 and CB2026-3). Protoplasts are cultured in liquid medium ($1.25 \times 10^5$ cells/ml), and incubated in the dark at 25° C. (SOP CB2052-2). Cell samples are obtained after one or three weeks, and analyzed by deep sequencing, to determine the frequency of mutations in target genes. After 6-8 weeks, protoplast-derived microcalli are transferred to solid regeneration medium, and shoots start differentiating from regenerated calli after about 2-4 weeks. Leaf samples from fully differentiated shoots are analyzed by NGS to determine the occurrence of targeted mutations in each of the 4 FAD2 genes. Shoots with targeted mutations in individual and multiple genes, covering all 15 possible gene LOF combinations or genotypes are then screened for ploidy (SOP CB2053), micropropagated in vitro (SOP 2018), and transferred to soil in a growth chamber (SOP GH3516-1). Hardened plants are transferred to the greenhouse and grown to maturation (seed setting).

TABLE 1 gRNAs used in application experiments

| gRNA ID | Gene Target | Spacer Sequence (5'-3') | Sequence VO (5'-3') |
|---|---|---|---|
| CR-FAD2-8 | BnFAD 2-1 (A05) and BnFAD 2-2 (C05) | ATCGAGCGTTT GAAACAGTG (SEQ ID NO: 14) | TGTAATACGACTC ACTATAGGTCGAG CGTTTGAAACAGT GGTTTTAGAGCTA GAAATAGCAAG (SEQ ID NO: 15) |
| CR-FAD2-9 | BnFAD 2-3 and BnFAD 2-4 | ATGGAGCGTTT GAAGCAGTG (SEQ ID NO: 16) | TGTAATACGACTC ACTATAGGTGGAG CGTTTGAAGCAGT GGTTTTAGAGCTA GAAATAGCAAG (SEQ ID NO: 17) |

TABLE 2

Sequence of ssODNs used in application experiment.

| GRON ID | Gene Target | SEQUENCE (5' to 3') |
|---|---|---|
| BnFAD2-1,2/C/42 + 1A 5` (1RNA)2`-O-Me-(1) (CR-8) | BnFAD2-1 (A05) and BnFAD2-2 (C05) | GAAAGCAATCCCACCGCACATG TTTCAAACGCTCGATCCCT (SEQ ID NO: 18) |
| BnFAD2-1,2/C/42 + 1C5` (1RNA)2`-O-Me-(1) (CR-8) | BnFAD2-1 (A05) and BnFAD2-2 (C05) | GAAAGCAATCCCACCGCACCTG TTTCAAACGCTCGATCCCT (SEQ ID NO: 19) |
| BnFAD2-1,2/C/42 + 1G5` (1RNA)2`-O-Me-(1) (CR-8) | BnFAD2-1 (A05) and BnFAD2-2 (C05) | GAAAGCAATCCCACCGCACGTG TTTCAAACGCTCGATCCCT (SEQ ID NO: 20) |
| BnFAD2-1,2/C/42 + 1T5` (1RNA)2`-O-Me-(1) (CR-8) | BnFAD2-1 (A05) and BnFAD2-2 (C05) | GAAAGCAATCCCACCGCACTTG TTTCAAACGCTCGATCCCT (SEQ ID NO: 21) |
| BnFAD2-1,2/C/40 − 1 5` (1RNA)2`-O-Me-(1) (CR-8) | BnFAD2-1 (A05) and BnFAD2-2 (C05) | GAAAGCAATCCCACCGCACGTT TCAAACGCTCGATCCCT (SEQ ID NO: 22) |
| BnFAD2-1,2/C/39 − 2 5` (1RNA)2`-O-Me-(1) (CR-8) | BnFAD2-1 (A05) and BnFAD2-2 (C05) | GAAAGCAATCCCACCGCACTTT CAAACGCTCGATCCCT (SEQ ID NO: 23) |
| BnFAD2-3,4/C/42 + 1A 5` (1RNA)2`-O-Me-(1) (CR-9) | BnFAD2-3 and BnFAD2-4 | GAAAGCAATCCCACCTCACATG CTTCAAACGCTCCATCCCA (SEQ ID NO: 24) |
| BnFAD2-3,4/C/42 + 1C 5` (1RNA)2`-O-Me-(1) (CR-9) | BnFAD2-3 and BnFAD2-4 | GAAAGCAATCCCACCTCACCTG CTTCAAACGCTCCATCCCA (SEQ ID NO: 25) |
| BnFAD2-3,4/C/42 + 1G 5` (1RNA)2`-O-Me-(1) (CR-9) | BnFAD2-3 and BnFAD2-4 | GAAAGCAATCCCACCTCACGTG CTTCAAACGCTCCATCCCA (SEQ ID NO: 26) |
| BnFAD2-3,4/C/42 + 1T 5` (1RNA)2`-O-Me-(1) (CR-9) | BnFAD2-3 and BnFAD2-4 | GAAAGCAATCCCACCTCACTTG CTTCAAACGCTCCATCCCA (SEQ ID NO: 27) |

TABLE 2-continued

| Sequence of ssODNs used in application experiment. |||
| --- | --- | --- |
| GRON ID | Gene Target | SEQUENCE (5' to 3') |
| BnFAD2-3,4/C/40 - 1 5` (1RNA)2`-O-Me-(1) (CR-9) | BnFAD2-3 and BnFAD2-4 | GAAAGCAATCCCACCTCACGCT TCAAACGCTCCATCCCA (SEQ ID NO: 28) |
| BnFAD2-3,4/C/39 - 2 5` (1RNA)2`-O-Me-(1) (CR-9) | BnFAD2-3 and BnFAD2-4 | GAAAGCAATCCCACCTCACCTTC AAACGCTCCATCCCA (SEQ ID NO: 29) |

Phenotypic analysis. Fatty acid profiles of dry seeds of FAD2 gene LOF lines and wild type control plants is determined by gas liquid chromatography (GC) with an Agilent 7890A GC analyzer, following a standard protocol.

Results

Brassica napus L. spp. oleifera; genomes AACC, 2n= 4x=38) is an allopolyploid plant originated through spontaneous hybridization between turnip rape (Brassica rapa L.; genome AA, 2n=2x=20), and cabbage (Brassica oleracea L.; genome CC, 2n=2x=18). Two FAD2 genes exist in B. rapa and B. oleracea, and therefore, four copies of FAD2 genes are found in B. napus (Yang et al., 2012; Lee et al., 2013). FAD2-1 and FAD2-2 genes are located on B. napus chromosomes A05 and C05 respectively. The chromosomal location of FAD2-3 and FAD2-4 genes is unknown. However, the FAD2-3 gene inherited from B. rapa carries a mutation that generates a truncated, non-functional protein (Lee et al., 2013). As expected, all 4 BnFAD2 gene sequences were cloned and sequenced from the BN2SU canola line (BnFAD2-1=SEQ ID NO: 1; BnFAD2-2=SEQ ID NO: 2; BnFAD2-3=SEQ ID NO: 3; BnFAD2-4=SEQ ID NO: 4). The deduced amino acid sequences of all BnFAD2 genes were identical to the reported sequences (BnFAD2-1=SEQ ID NO: 5; BnFAD2-2=SEQ ID NO: 6; BnFAD2-3=SEQ ID NO: 7 or SEQ ID NO: 30; BnFAD2-4=SEQ ID NO: 31; Lee et al., 2013).

All 4 FAD2 genes were targeted with RNPs and GRONs to generate LOF lines with non-functional FAD2 genes. The goal was to generate all possible single and multiple FAD2 LOF genotypes that would have higher levels of oleic acid than the wild type. Table 3 summarizes the number of shoots regenerated with each of the 15 possible LOF genotypes, including shoots with single and multiple FAD2 LOF genes in two canola lines; BN2SU and 412SUR. GRON targeted mutations (+1, −1, −2 nucleotide insertion or deletions, InDels) in at least one of the 4 FAD2 genes were respectively found in about 30% and 40% of the shoots regenerated from treated protoplasts of lines BN2SU and 412SUR, as determined by Next Generation Sequencing. Shoots with targeted mutations in 1 through 4 of the genes were identified with different frequencies. Targeted InDels generate LOF genes by shifting the reading frame of FAD2 genes.

TABLE 3

| Shoots regenerated with targeted InDels in FAD2 genes in the BN2SU and 412SUR line ||||
| --- | --- | --- | --- |
| | | | Shoots with Targeted InDels |
| Genotype | | Total Gene | |
| # | FAD2 Gene LOF | LOFs | BN2SU | 412SUR |
| 1 | fad2-1 | 1 | 71 | 130 |
| 2 | fad2-2 | | 67 | 106 |

TABLE 3-continued

| Shoots regenerated with targeted InDels in FAD2 genes in the BN2SU and 412SUR line ||||
| --- | --- | --- | --- |
| | | | Shoots with Targeted InDels |
| | Genotype | Total Gene | |
| # | FAD2 Gene LOF | LOFs | BN2SU | 412SUR |
| 3 | fad2-3 | | 174 | 161 |
| 4 | fad2-4 | | 96 | 118 |
| 5 | fad2-1; fad2-2 | 2 | 6 | 51 |
| 6 | fad2-1; fad2-3 | | 19 | 62 |
| 7 | fad2-1; fad2-4 | | 8 | 34 |
| 8 | fad2-2; fad2-3 | | 21 | 58 |
| 9 | fad2-2; fad2-4 | | 8 | 37 |
| 10 | fad2-3; fad2-4 | | 41 | 121 |
| 11 | fad2-1; fad2-2; fad2-3 | 3 | 2 | 29 |
| 12 | fad2-1; fad2-2; fad2-4 | | 0 | 12 |
| 13 | fad2-1; fad2-3; fad2-4 | | 13 | 91 |
| 14 | fad2-2; fad2-3; fad2-4 | | 1 | 68 |
| 15 | fad2-1; fad2-2; fad2-3; fad2-4 | 4 | 1 | 51 |

Seed oil fatty acid composition in dry seeds of BN2SU FAD2 gene LOF lines are shown in Tables 4A-4D, and Table 4E shows mutations in BN2SU FAD2 gene LOF lines. Seed oil fatty acid composition in dry seeds of 412SUR FAD2 gene LOF lines are shown in Tables 5A-5D, and Table 5E shows mutations in 412SURFAD2 gene LOF lines. The fatty acid compositions were measured by gas chromatography. In the "Genotype" column of Tables 4A-4D and Tables 5A-5D, the number provided for "n" in parentheses represents the number of independent LOF lines analyzed per genotype. Table 5F shows the amino acid positions of predicted stop codons resulting from the FAD2 mutations.

Average oleic acid % by weight content in seeds of BN2SU and 412SUR wild type lines used as controls was ~64% and 61% respectively (Tables 4B and 5B). Average oleic acid in BN2SU LOF lines with a single non-functional fad2-1 gene was 75.31±1.5% by weight, and 69.96±1.46% by weight in fad2-2 single LOF lines. However, oleic acid levels in seeds of fad2-3 and fad2-4 single LOF lines were ~61% by weight, similar to wild type levels. The double fad2-1 and fad2-2 gene LOF lines have much higher oleic acid levels of 86.33±0.7% by weight (Table 4B). Level of oleic acid in a full LOF line (fad2-1; fad2-2; fad2-3; fad2-4) was slightly higher (87.96% by weight), than in the double fad2-1 and fad2-2 gene LOF lines. This is about 24% by weight higher than the wild type. Saturated fatty acid (e.g., palmitic or stearic fatty acids) levels in the seeds of FAD2 gene LOF lines are not altered significantly relative to those measured in the wild type seeds. Similar results were obtained with the 412SUR FAD2 LOF lines (Tables 5A-5D).

TABLE 4A

Palmitic and palmitoleic fatty acid composition
in dry seeds of BN2SU FAD2 gene LOF lines.

| | | Palmitic (16:0) | | Palmitoleic (16:1) | |
| --- | --- | --- | --- | --- | --- |
| Genotype | FAD2 Gene LOFs | % by weight average | ±SD | % by weight average | ±SD |
| BN2SU (wild type) | 0 | 3.94 | N/A | 0.34 | N/A |
| High Oleic Check | unknown | 3.77 | N/A | 0.28 | N/A |
| fad2-1 (n = 3) | 1 | 3.4 | 0.04 | <0.1 | N/A |
| fad2-2 (n = 3) | | 3.55 | 0.11 | <0.1 | N/A |
| fad2-3 (n = 1) | | 3.44 | N/A | <0.1 | N/A |
| fad2-4 (n = 3) | | 3.67 | 0.15 | <0.1 | N/A |
| fad2-1; fad2-2 (n = 2) | 2 | 3.01 | 0.24 | <0.1 | N/A |
| fad2-1; fad2-3 (n = 2) | | 3.58 | 0.22 | <0.1 | N/A |
| fad2-1; fad2-4 (n = 3) | | 3.51 | 0.18 | <0.1 | N/A |
| fad2-2; fad2-3 (n = 2) | | 3.71 | 0.1 | <0.1 | N/A |
| fad2-2; fad2-4 (n = 3) | | 3.62 | 0.13 | <0.1 | N/A |
| fad2-3; fad2-4 (n = 3) | | 3.77 | 0.14 | <0.1 | N/A |
| fad2-1; fad2-2; fad2-3 (n = 1) | 3 | 3.05 | N/A | <0.1 | N/A |
| fad2-1; fad2-2; fad2-4 (n = 0) | | — | — | — | — |
| fad2-1; fad2-3; fad2-4 (n = 4) | | 3.44 | 0.06 | 0.05 | 0.09 |
| fad2-2; fad2-3; fad2-4 (n = 2) | | 3.5 | 0.01 | <0.1 | N/A |
| fad2-1; fad2-2; fad2-3; fad2-4 (n = 1) | 4 | 3.15 | N/A | 0.24 | N/A |

TABLE 4C

Linoleic and linolenic fatty acid composition
in dry seeds of BN2SU FAD2 gene LOF lines.

| | | Linoleic (18:2) | | Linolenic (18:3) | |
| --- | --- | --- | --- | --- | --- |
| Genotype | FAD2 Gene LOFs | % by weight average | ±SD | % by weight average | ±SD |
| BN2SU (wild type) | 0 | 21.26 | N/A | 6.52 | N/A |
| High Oleic Check | unknown | 16.31 | N/A | 2.09 | N/A |
| fad2-1 (n = 3) | 1 | 10.51 | 0.52 | 8.67 | 1.07 |
| fad2-2 (n = 3) | | 14.6 | 0.6 | 8.8 | 1.11 |
| fad2-3 (n = 1) | | 22.35 | N/A | 0.55 | N/A |
| fad2-4 (n = 3) | | 22.18 | 1.18 | 9.16 | 2.15 |
| fad2-1; fad2-2 (n = 2) | 2 | 2.6 | 0.32 | 5.16 | 1.00 |
| fad2-1; fad2-3 (n = 2) | | 13.1 | 1.31 | 9.41 | 0.26 |
| fad2-1; fad2-4 (n = 3) | | 10.81 | 0.94 | 7.91 | 0.98 |
| fad2-2; fad2-3 (n = 2) | | 15.3 | 0.81 | 9.36 | 0.46 |
| fad2-2; fad2-4 (n = 3) | | 14.48 | 0.47 | 8.81 | 0.3 |
| fad2-3; fad2-4 (n = 3) | | 23.52 | 0.88 | 10.69 | 0.82 |
| fad2-1; fad2-2; fad2-3 (n = 1) | 3 | 2.75 | N/A | 4.64 | N/A |
| fad2-1; fad2-2; fad2-4 (n = 0) | | — | — | — | — |
| fad2-1; fad2-3; fad2-4 (n = 4) | | 10.17 | 0.82 | 7.64 | 1.34 |
| fad2-2; fad2-3; fad2-4 (n = 2) | | 13.14 | 1.34 | 6.53 | 1.71 |
| fad2-1; fad2-2; fad2-3; fad2-4 (n = 1) | 4 | 2.1 | N/A | 3.25 | N/A |

TABLE 4B

Stearic and oleic fatty acid composition in
dry seeds of BN2SU FAD2 gene LOF lines.

| | | Stearic (18:0) | | Oleic (18:1) | |
| --- | --- | --- | --- | --- | --- |
| Genotype | FAD2 Gene LOFs | % by weight average | ±SD | % by weight average | ±SD |
| BN2SU (wild type) | 0 | 2.79 | N/A | 63.92 | N/A |
| High Oleic Check | unknown | 1.21 | N/A | 75.63 | N/A |
| fad2-1 (n = 3) | 1 | 1.96 | 0.39 | 74.65 | 1.03 |
| fad2-2 (n = 3) | | 2.14 | 0.57 | 69.96 | 1.46 |
| fad2-3 (n = 1) | | 1.79 | N/A | 61.61 | N/A |
| fad2-4 (n = 3) | | 2.4 | 0.66 | 61.62 | 2.34 |
| fad2-1; fad2-2 (n = 2) | 2 | 1.84 | 0.6 | 86.33 | 0.71 |
| fad2-1; fad2-3 (n = 2) | | 2.18 | N/A | 70.84 | 0.55 |
| fad2-1; fad2-4 (n = 3) | | 2.18 | 0.31 | 74.91 | 1.57 |
| fad2-2; fad2-3 (n = 2) | | 2.03 | 0.33 | 68.96 | 1.06 |
| fad2-2; fad2-4 (n = 3) | | 2.25 | 0.28 | 70.11 | 0.51 |
| fad2-3; fad2-4 (n = 3) | | 1.75 | 0.07 | 59.69 | 1.46 |
| fad2-1; fad2-2; fad2-3 (n = 1) | 3 | 2.18 | N/A | 86.2 | N/A |
| fad2-1; fad2-2; fad2-4 (n = 0) | | — | — | — | — |
| fad2-1; fad2-3; fad2-4 (n = 4) | | 2.26 | 0.34 | 75.31 | 1.5 |
| fad2-2; fad2-3; fad2-4 (n = 2) | | 2.18 | 0.03 | 73.93 | 3.06 |
| fad2-1; fad2-2; fad2-3; fad2-4 (n = 1) | 4 | 2.07 | N/A | 87.96 | N/A |

TABLE 4D

Eicosenoic and erucic fatty acid composition
in dry seeds of BN2SU FAD2 gene LOF lines.

| | | Eicosenoic (20:1) | | Erucic (22:1) | |
| --- | --- | --- | --- | --- | --- |
| Genotype | FAD2 Gene LOFs | % by weight average | ±SD | % by weight average | ±SD |
| BN2SU (wild type) | 0 | 0.87 | N/A | 0.36 | N/A |
| High Oleic Check | unknown | 0.47 | N/A | 0.24 | N/A |
| fad2-1 (n = 3) | 1 | 0.69 | 0.12 | 0.11 | 0.19 |
| fad2-2 (n = 3) | | 0.72 | 0.14 | 0.22 | 0.2 |
| fad2-3 (n = 1) | | 10.26 | N/A | <0.1 | N/A |
| fad2-4 (n = 3) | | 0.73 | 0.17 | 0.22 | 0.2 |
| fad2-1; fad2-2 (n = 2) | 2 | 0.7 | 0.18 | 0.36 | 0.07 |
| fad2-1; fad2-3 (n = 2) | | 0.71 | 0.03 | 0.18 | 0.25 |
| fad2-1; fad2-4 (n = 3) | | 0.69 | 0.07 | <0.1 | N/A |
| fad2-2; fad2-3 (n = 2) | | 0.65 | 0.03 | <0.1 | N/A |
| fad2-2; fad2-4 (n = 3) | | 0.72 | 0.06 | <0.1 | N/A |
| fad2-3; fad2-4 (n = 3) | | 0.59 | 0.04 | <0.1 | N/A |
| fad2-1; fad2-2; fad2-3 (n = 1) | 3 | 0.79 | N/A | 0.37 | N/A |
| fad2-1; fad2-2; fad2-4 (n = 0) | | — | — | — | — |
| fad2-1; fad2-3; fad2-4 (n = 4) | | 0.78 | 0.13 | 0.34 | 0.07 |
| fad2-2; fad2-3; fad2-4 (n = 2) | | 0.72 | 0.02 | <0.1 | N/A |
| fad2-1; fad2-2; fad2-3; fad2-4 (n = 1) | 4 | 0.82 | N/A | 0.41 | N/A |

TABLE 4E

Mutations in BN2SU FAD2 gene LOF lines.

| Genotype | Line | FAD2 Gene LOFs | Genotype fad2-1 | fad2-2 | fad2-3 | fad2-4 | SEQ ID NO: fad2-1 | fad2-2 | fad2-3 | fad2-4 |
|---|---|---|---|---|---|---|---|---|---|---|
| BN2SU | Wild type | 0 | wt | wt | wt | wt | 32 | 37 | 45 | 47 |
| fad2-1 | A02__877-3 | 1 | n + T | wt | wt | wt | 33 | 37 | 45 | 47 |
| | A04__004-4 | | n-1 (TG->T) | wt | wt | wt | 34 | 37 | 45 | 47 |
| | A04__232-1 | | n + T | wt | wt | wt | 33 | 37 | 45 | 47 |
| fad2-2 | A02__306-1 | | wt | n + T | wt | wt | 32 | 38 | 45 | 47 |
| | A02__499-1 | | wt | n + T | wt | wt | 32 | 38 | 45 | 47 |
| | A02__819-2 | | wt | n + T | wt | wt | 32 | 38 | 45 | 47 |
| fad2-3 | A02__226-1 | | wt | wt | n + T | wt | 32 | 37 | 46 | 47 |
| fad2-4 | A02__217-1 | | wt | wt | wt | n + T | 32 | 37 | 45 | 48 |
| | A02__318-2 | | wt | wt | wt | n + T | 32 | 37 | 45 | 48 |
| | A02__367-1 | | wt | wt | wt | n + T | 32 | 37 | 45 | 48 |
| fad2-1; fad2-2 | A02__024-4 | 2 | n + T | n + T | wt | wt | 33 | 38 | 45 | 47 |
| | A02__895-3 | | n + T | n + T | wt | wt | 33 | 38 | 45 | 47 |
| fad2-1; fad2-3 | A04__307-1 | | n + T | wt | n + T | wt | 33 | 37 | 46 | 47 |
| | A04__144-1 | | n + T | wt | n + T | wt | 33 | 37 | 46 | 47 |
| fad2-1; fad2-4 | A04__035-2 | | n-1 (GT->G) | wt | wt | n + T | 35 | 37 | 45 | 48 |
| | A04__353-1 | | n + T | wt | wt | n + T | 33 | 37 | 45 | 48 |
| | A04__390-4 | | n + T | wt | wt | n + T | 33 | 37 | 45 | 48 |
| fad2-2; fad2-3 | A04__273-1 | | wt | n-1 (AC->A) | n + T | wt | 32 | 39 | 46 | 47 |
| | A04__541-1 | | wt | n + T | n + T | wt | 32 | 38 | 46 | 47 |
| | A04__894-1 | | wt | n + T | n + T | wt | 32 | 38 | 46 | 47 |
| fad2-2; fad2-4 | A04__222-1 | | wt | n + T | wt | n + T | 32 | 38 | 45 | 48 |
| | A04__291-3 | | wt | n + T | wt | n + T | 32 | 38 | 45 | 48 |
| | A02__627-1 | | wt | n + T | wt | n + T | 32 | 38 | 45 | 48 |
| fad2-3; fad2-4 | A02__027-1 | | wt | wt | n + T | n + T | 32 | 37 | 46 | 48 |
| | A02__214-1 | | wt | wt | n + T | n + T | 32 | 37 | 46 | 48 |
| | A02__343-1 | | wt | wt | n + T | n + T | 32 | 37 | 46 | 48 |
| fad2-2; fad2-3; fad2-4 | A02__434-1 | 3 | wt | n + T | n + T | n-3 (ACTG->A) | 32 | 38 | 46 | 50 |
| | A04__937-3 | | wt | n + T | n + T | n + T | 32 | 38 | 46 | 48 |
| fad2-1; fad2-2; fad2-3 | A02__428-1 | | n + T | n + T | n + T | wt | 33 | 38 | 46 | 47 |
| fad2-1; fad2-3; fad2-4 | A04-917-1 | | n + T | wt | n + T | n + T | 33 | 37 | 46 | 48 |
| | A04__129-4 | | n + T | wt | n + T | n + T | 33 | 37 | 46 | 48 |
| | A04__416-4 | | n + T | wt | n + T | n + T | 33 | 37 | 46 | 48 |
| | A04__469-3 | | n + T | wt | n + T | n + T | 33 | 37 | 46 | 48 |
| fad2-1; fad2-2; fad2-3; fad2- | A04__988-1 | 4 | n + T | n-4 (ACTGT->A) | n + T | n + T | 33 | 43 | 46 | 48 |

TABLE 5A

Palmitic and palmitoleic fatty acid composition
in dry seeds of 412SUR FAD2 gene LOF lines.

| Genotype | FAD2 Gene LOFs | Palmitic (16:0) % by weight average | ±SD | Palmitoleic (16:1) % by weight average | ±SD |
|---|---|---|---|---|---|
| 412SUR (wild type) | 0 | 3.75 | N/A | 0.2 | N/A |
| High Oleic Check | unknown | 3.97 | N/A | 0.22 | N/A |
| fad2-1; fad2-2 (n = 3) | 2 | 3.8 | 0.39 | 0.45 | 0.28 |
| fad2-2; fad2-4 (n = 1) | | 3.95 | N/A | 0.19 | N/A |
| fad2-1; fad2-2; fad2-4 (n = 2) | 3 | 3.42 | 0.06 | 0.26 | 0.01 |
| fad2-1; fad2-2; fad2-3; fad2-4 (n = 3) | 4 | 3.37 | 0.04 | 0.25 | 0.03 |

TABLE 5B

Stearic and oleic fatty acid composition in
dry seeds of 412SUR FAD2 gene LOF lines.

| Genotype | FAD2 Gene LOFs | Stearic (18:0) % by weight average | ±SD | Oleic (18:1) % by weight average | ±SD |
|---|---|---|---|---|---|
| 412SUR (wild type) | 0 | 1.89 | N/A | 61.13 | N/A |
| High Oleic Check | unknown | 1.53 | N/A | 73.65 | N/A |
| fad2-1; fad2-2 (n = 3) | 2 | 1.69 | 0.06 | 82.73 | 3.92 |
| fad2-2; fad2-4 (n = 1) | | 1.71 | N/A | 69.51 | N/A |
| fad2-1; fad2-2; fad2-4 (n = 2) | 3 | 2.01 | 0.04 | 88.21 | 0.49 |
| fad2-1; fad2-2; fad2-3; fad2-4 (n = 3) | 4 | 1.82 | 0.18 | 88.62 | 0.24 |

TABLE 5C

Linoleic and linolenic fatty acid composition
in dry seeds of 412SUR FAD2 gene LOF lines.

| | | Linoleic (18:2) | | Linolenic (18:3) | |
|---|---|---|---|---|---|
| Genotype | FAD2 Gene LOFs | % by weight average | ±SD | % by weight average | ±SD |
| 412SUR (wild type) | 0 | 20.18 | N/A | 12.34 | N/A |
| High Oleic Check | unknown | 17.58 | N/A | 2.59 | N/A |
| fad2-1; fad2-2 (n = 3) | 2 | 3.45 | 0.79 | 7.35 | 2.36 |
| fad2-2; fad2-4 (n = 1) | | 13.64 | N/A | 10.52 | N/A |
| fad2-1; fad2-2; fad2-4 (n = 2) | 3 | 1.87 | 0.04 | 3.65 | 0.42 |
| fad2-1; fad2-2; fad2-3; fad2-4 (n = 3) | 4 | 1.9 | 0.03 | 3.47 | 0.01 |

TABLE 5D

Eicosenoic fatty acid composition in dry
seeds of BN2SU FAD2 gene LOF lines.

| | | Eicosenoic (20:1) | |
|---|---|---|---|
| Genotype | FAD2 Gene LOFs | % by weight average | ±SD |
| 412SUR (wild type) | 0 | 0.52 | N/A |
| High Oleic Check | unknown | 0.45 | N/A |
| fad2-1; fad2-2 (n = 3) | 2 | 0.527 | 0.07 |
| fad2-2; fad2-4 (n = 1) | | 0.48 | N/A |
| fad2-1; fad2-2; fad2-4 (n = 2) | 3 | 0.57 | 0.01 |
| fad2-1; fad2-2; fad2-3; fad2-4 (n = 3) | 4 | 0.56 | 0.06 |

TABLE 5E

Mutations in 412SUR FAD2 gene LOF lines.

| | | FAD2 Gene | Genotype | | | | SEQ ID NO: | | | |
|---|---|---|---|---|---|---|---|---|---|---|
| Genotype | Line | LOFs | fad2-1 | fad2-2 | fad2-3 | fad2-4 | fad2-1 | fad2-2 | fad2-3 | fad2-4 |
| 412SUR | Wild type | 0 | wt | wt | wt | wt | 32 | 37 | 45 | 47 |
| fadd2-1; fad2-2 | A03_334 | 2 | n-2 (CTG –> C) | n-2 (CTG –> C) | wt | wt | 36 | 41 | 45 | 47 |
| | A03_349 | | n + T | n + T | wt | wt | 33 | 38 | 45 | 47 |
| | A03_746 | | n + T | n – T | wt | wt | 33 | 40 | 45 | 47 |
| fad2-2; fad2-4 | A05_2077 | | wt | n-3 (GCAC –> G) | wt | n + T | 32 | 42 | 45 | 48 |
| fad2-1; fad2-2; fad2-4 | A03_042 | 3 | n-2 (CTG –> C) | n + T | wt | n – T | 36 | 38 | 45 | 49 |
| | A05_1445 | | n + T | n + T | wt | n + T | 33 | 38 | 45 | 48 |
| | A05_2132 | | n-2 (CTG –> C) | n-6 (TGTTTCA –> T) | wt | n + T | 36 | 44 | 45 | 48 |
| fad2-1; fad2-2; fad2-3; fad2-4 | A05_527 | 4 | n + T | n – T | n + T | n + T | 33 | 40 | 46 | 48 |
| | A05_997 | | n + T | n + T | n + T | n + T | 33 | 38 | 46 | 48 |

TABLE 5F

Predicted stop codons resulting from FAD2 mutations.

| SEQ ID NO: | Predicted Stop Codon (amino acid position) |
|---|---|
| 32[1] | 385 |
| 33 | 222 |
| 34 | 62 |

TABLE 5F-continued

Predicted stop codons resulting from FAD2 mutations.

| SEQ ID NO: | Predicted Stop Codon (amino acid position) |
|---|---|
| 35 | 62 |
| 36 | 221 |
| 37[1] | 385 |
| 38 | 119 |
| 39 | 62 |
| 40 | 62 |
| 41 | 118 |
| 42[2] | 384 |
| 43 | 61 |
| 44 | 44 |
| 45[1] | 175 |
| 46 | 93 |
| 47[1] | 386 |
| 48 | 156 |
| 49 | 97 |
| 50[2] | 385 |

[1]These are wt sequences without mutations.
[2]These two sequences contain n-3 mutations (as compared to the wt sequence) that result in the loss of 1 amino acid, but no frameshift or predicted premature stop codon.

Due to a concomitant reduction in the quantities of linoleic and linolenic acids, the results indicate that FAD2-1 and FAD2-2 genes are the major contributors to the desaturation of oleic acid in canola seed oil, as it has been previously reported (Yang et al., 2012; Lee et al., 2013). The results also reconfirm that FAD2-3 gene in canola is a non-functional gene that does not contribute to oleic acid desaturation in wild type canola. FAD2-4 gene is only responsible for about 2-5% increase of oleic acid in the seeds.

Seed oil fatty acid compositions in dry seeds of BN2SU FAD2 triple LOF lines are shown below in Table 6. Seeds were harvested at different stages through the season, from greenhouse to field. Seeds from material grown in one greenhouse location and two field locations were evaluated. In addition, the seeds harvested from Field Location 1 were evaluated by two separate laboratories (i.e., laboratory testing was done on the same material). The average values in Table 6 are the averages of results across all measured fatty acid composition by % weight values (i.e., values from all locations and laboratories). The fatty acid compositions by % weight were measured by a method that references American Oil Chemists' Society (AOCS) Official Method Ce 1h-05.

TABLE 6

Fatty acid compositions by % weight of FAD2 triple LOF lines grown in the greenhouse and field.

| Fatty Acid | Greenhouse | Location (Fatty Acid composition by % weight) | | Laboratory (Fatty Acid composition by % weight) | | Average (Fatty Acid composition by % weight) |
| | | Field Location 1 | Field Location 2 | RBD[3] Lab 1 | RBD[3] Lab 2 | |
|---|---|---|---|---|---|---|
| C12:0 | 0.01% | 0.01% | 0.01% | 0.00% | 0.01% | 0.01% |
| C14:0 | 0.04% | 0.04% | 0.04% | 0.10% | 0.04% | 0.05% |
| C16:0 | 2.94% | 2.76% | 2.92% | 3.10% | 3.05% | 2.95% |
| C16:1 | 0.19% | 0.18% | 0.22% | 0.03% | 0.28% | 0.18% |
| C17:0 | 0.74% | 0.56% | 0.57% | 0.06% | 0.58% | 0.50% |
| C17:1 | 1.17% | 0.95% | 1.01% | 1.00% | 0.91% | 1.01% |
| C18:0 | 1.72% | 1.87% | 1.53% | 1.90% | 2.00% | 1.80% |
| C18:1 | 82.68% | 83.13% | 82.21% | 81.40% | 81.51% | 82.19% |
| C18:2 | 2.29% | 1.93% | 2.62% | 3.60% | 2.68% | 2.62% |
| C18:3 | 4.96% | 4.70% | 4.43% | 3.10% | 3.18% | 4.07% |
| C20:0 | 0.71% | 0.78% | 0.65% | 0.80% | 0.88% | 0.76% |
| C20:1 | 1.62% | 1.73% | 1.69% | 1.80% | 1.93% | 1.75% |
| C22:0 | 0.41% | 0.43% | 0.39% | 0.50% | 0.54% | 0.45% |
| C22:1 | 0.03% | 0.03% | 0.03% | 0.10% | 0.08% | 0.05% |
| Other fatty acids | 0.49% | 0.90% | 1.68% | 2.51% | 2.91% | 1.70% |
| Total saturated fatty acids | 6.57% | 6.45% | 6.11% | 6.46% | 7.10% | 6.54% |
| Total MUFA[1] | 85.66% | 85.99% | 85.13% | 84.23% | 84.63% | 85.13% |
| Total PUFA[2] | 7.25% | 6.63% | 7.05% | 6.70% | 5.86% | 6.70% |

[1]MUFA = monounsaturated fatty acids
[2]PUFA = polyunsaturated fatty acids
[3]RBD = oil profile after it has been refined, bleached, and deodorized The fatty acid compositions of different oils as compared to the oil obtained from CIBUS line #1 are shown below in Table 7. CIBUS line #1 is a BN2SU FAD2 triple LOF line with the genotype fad2-1; fad2-2; fad2-3 (CIBUS line #1 contains the sequences SEQ ID NO: 51, SEQ ID NO: 52, SEQ ID NO: 53, and SEQ ID NO: 54). The Oxidative Stability Index (OSI) result for the CIBUS line #1 canola oil indicated that this oil had high oxidative stability. Specifically, the OSI value represented the number of hours that the oil was stable during the assay, meaning that the CIBUS line #1 canola oil maintained oxidative stability for at least 32 hours. In comparison, conventional canola oil (e.g., Commodity Canola) had an oxidative stability of 7-8 hours, and mid-oleic canola oil had an oxidative stability of about 15 hours (e.g., Clear Valley® CV 65 Canola Oil).

TABLE 7

Fatty acid composition and Oxidative Stability Index (OSI) values for different oils.

| Canola Oil | Fatty acid composition by % weight | | | | |
| | C18:1 | C18:2 | C18:3 | PUFA[1] | OSI[2] |
|---|---|---|---|---|---|
| Commodity Canola | 60 | 20 | 10 | 30 | 9 |
| Clear Valley ® CV 65 Canola Oil | 65 | 24 | 3 | 27 | 15 |
| Clear Valley ® CV 75 Canola Oil | 75 | 14 | 3 | 17 | 19 |
| Clear Valley ® CV 80 Canola Oil | 80 | 9 | 3 | 12 | 26 |

TABLE 7-continued

Fatty acid composition and Oxidative Stability Index (OSI) values for different oils.

| Canola Oil | Fatty acid composition by % weight | | | | |
| | C18:1 | C18:2 | C18:3 | PUFA[1] | OSI[2] |
|---|---|---|---|---|---|
| Low linoleic canola | 62.1 | 25.3 | 3.2 | 28.5 | 8.3 |
| CIBUS line #1 | 88 | 2 | 3 | 5 | 32.65 |

[1]PUFA = polyunsaturated fatty acids
[2]OSI = Oxidative Stability Index

Further, CIBUS line #1 canola oil had a lower level of C18:2 than C18:3 fatty acids by % weight, unlike all of the other oils in Table 7. Moreover, the ratio of C18:2 (omega 6 type) to C18:3 (omega 3 type) was less than 1; all of the other oils in the table had a ratio of greater than 1. Diets with lower omega-6 to omega-3 ratios have been linked to reduced risk of chronic disease (Simopolous, Biomed. Pharmacother., 56(8):365-379, 2002).

Figure 1B:
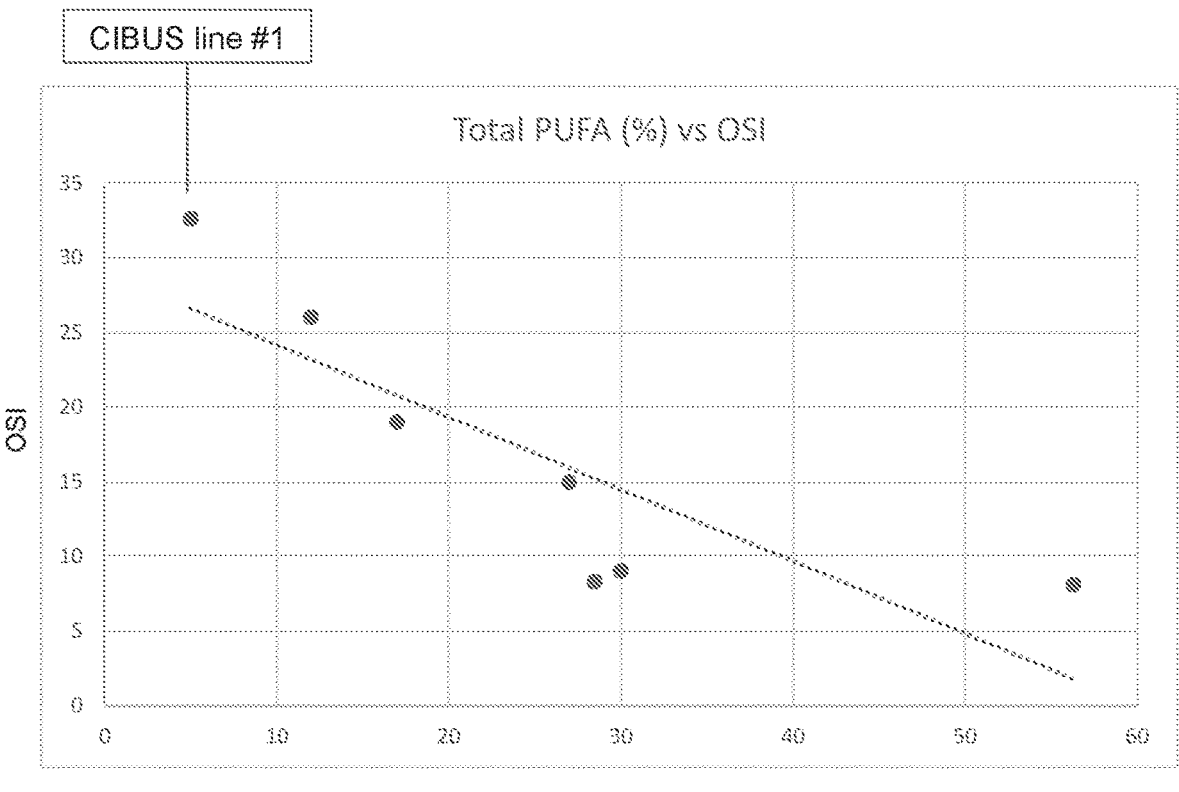

FIGS. 1A and 1B show graphs comparing the oleic acid % vs. OSI (FIG. 1A) and the total PUFA % vs. OSI (FIG. 1B) for the oils in Table 7. FIG. 1A shows that the CIBUS line #1 canola oil possessed extra anti-oxidant properties compared to the other oils. FIG. 1B shows that the CIBUS line #1 canola oil was an outlier in the trend compared to the other oils, as it had a much higher OSI than total PUFA %.

We claim:

1. A *Brassica napus* plant or part thereof comprising a homozygous loss-of-function mutation in three endogenous genes encoding fatty acid desaturase 2 (FAD2) polypeptides having the coding sequences of SEQ ID NO: 1, SEQ ID NO: 2, and SEQ ID NO: 3, and wherein the plant or part thereof comprises a FAD2 gene having the coding sequence of SEQ ID NO: 4 which encodes a functional FAD2 polypeptide, and wherein seed oil produced from the plant exhibits the following characteristics:

1) contains oleic acid at a level of at least 80% by weight of the total fatty acid content of the seeds;

2) contains linoleic acid at a level less than 4% by weight of the total fatty acid content of the seeds;

3) contains linolenic acid at a level less than 5% by weight of the total fatty acid content of the seeds;

4) the ratio of the quantity of linoleic acid to linolenic acid is less than 1; and 5) has increased oxidative stability for at least 32 hours as compared to a corresponding control.

2. The plant or part thereof of claim 1, wherein the plant produces seeds and the seeds comprise oleic acid at a level of at least 81%, at least 82%, at least 83%, at least 84%, at least 85%, at least 86%, at least 87%, at least 88%, at least 89%, at least 90%, at least 91%, at least 92%, at least 93%, at least 94%, or at least 95% by weight of the total fatty acid content of the seeds; and/or the seeds comprise linoleic acid at a level of less than 3% or less than 2% by weight of the total fatty acid content of the seeds.

3. An F1 *Brassica napus* plant, wherein the F1 plant has the plant of claim 1 as a parent.

4. A method of making plant seeds, the method comprising crossing the plant of claim 1 with another *Brassica napus* plant and harvesting seed therefrom.

5. A *Brassica napus* plant produced by growing the seed of claim 4, wherein the plant has all the physiological and morphological characteristics of a *Brassica napus* plant comprising a homozygous loss-of-function mutation in three endogenous genes encoding fatty acid desaturase 2 (FAD2) polypeptides having the coding sequences of SEQ ID NO: 1, SEQ ID NO: 2, and SEQ ID NO: 3, and wherein the plant comprises a FAD2 gene having the coding sequence of SEQ ID NO: 4 which encodes a functional FAD2 polypeptide, and wherein seed oil produced from the plant exhibits the following characteristics:

1) contains oleic acid at a level of at least 80% by weight of the total fatty acid content of the seeds;

2) contains linoleic acid at a level less than 4% by weight of the total fatty acid content of the seeds;

3) contains linolenic acid at a level less than 5% by weight of the total fatty acid content of the seeds;

4) the ratio of the quantity of linoleic acid to linolenic acid is less than 1; and 5) has increased oxidative stability for at least 32 hours as compared to a corresponding control.

6. Oil extracted from seeds of *Brassica napus* plants comprising a homozygous loss-of-function mutation in three endogenous genes encoding fatty acid desaturase 2 (FAD2) polypeptides having the coding sequences of SEQ ID NO: 1, SEQ ID NO: 2, and SEQ ID NO: 3, and wherein the *Brassica napus* plants comprise a FAD2 gene having the coding sequence of SEQ ID NO: 4 which encodes a functional FAD2 polypeptide, and wherein the oil exhibits the following characteristics:

1) contains oleic acid at a level of at least 80% by weight of the total fatty acid content of the seeds;

2) contains linoleic acid at a level less than 4% by weight of the total fatty acid content of the seeds;

3) contains linolenic acid at a level less than 5% by weight of the total fatty acid content of the seeds;

4) a ratio of the quantity of linoleic acid to linolenic acid less than 1; and 5) has increased oxidative stability for at least 32 hours as compared to a corresponding control.

7. The oil of claim 6, wherein the oil comprises oleic acid at a level of about 82-88%, 82-89%, 84-90%, or 86-90% or greater by weight of the total fatty acid content of the seeds.

8. A method of producing the plant of claim 1, comprising the steps of:

a) introducing mutations into plant cells, wherein the mutations are homozygous loss-of-function mutations in three endogenous genes encoding FAD2 polypeptides having the coding sequences of SEQ ID NO: 1, SEQ ID NO: 2, and SEQ ID NO: 3, and wherein SEQ ID NO: 4 encodes a functional FAD2 polypeptide in the same plant cells;

b) selecting or identifying plant cells containing the mutations; and c) regenerating a plant having the mutations;

wherein the *Brassica napus* plant produces seeds and the seeds comprise an oleic acid content that is higher than a corresponding control plant that does not comprise the three mutations and the functional FAD2 polypeptide of SEQ ID NO: 4, and wherein the seed oil produced from the plant exhibits the following characteristics:

1) contains oleic acid at a level of at least 80% by weight of the total fatty acid content of the seeds;

2) contains linoleic acid at a level less than 4% by weight of the total fatty acid content of the seeds;

3) contains linolenic acid at a level less than 5% by weight of the total fatty acid content of the seeds;

4) the ratio of the quantity of linoleic acid to linolenic acid is less than 1; and 5) has increased oxidative stability for at least 32 hours as compared to seed oil of a corresponding control plant that does not comprise the three mutations.

9. The method of claim 8, wherein the seed comprises an oleic acid content of at least 81%, at least 82%, at least 83%, at least 84%, at least 85%, at least 86%, at least 87%, at least 88%, at least 89%, at least 90%, at least 91%, at least 92%, at least 93%, at least 94%, or at least 95%, and/or a linoleic acid content of less than 3% or less than 2%.

10. The method of claim 8, wherein the mutations are introduced using one or more vectors, wherein the vectors comprise gene editing components selected from the group consisting of a CRISPR/Cas9 system, a TALEN, a zinc finger, and a meganuclease designed to target a nucleic acid sequence encoding a FAD2 gene.

11. The method of claim 10, wherein the mutations are introduced using a GRON system designed to target a nucleic acid sequence encoding a FAD2 gene.

12. The method of claim 11, wherein the GRON system comprises one or more modifications selected from the group consisting of a Cy3 group, 3PS group, and a 2'O-methyl group.

13. A method for producing seed oil in a seed, said method comprising growing a *Brassica napus* plant comprising a homozygous loss-of-function mutation in at least three endogenous genes encoding FAD2 polypeptides, wherein the endogenous genes comprise a coding sequence selected from the group consisting of having the coding sequences of SEQ ID NO: 1, SEQ ID NO: 2, and SEQ ID NO: 3, and wherein the plant comprises a FAD2 gene having the coding sequence of SEQ ID NO: 4 which encodes a functional FAD2 polypeptide, and wherein said *Brassica napus* plant produces seeds, and wherein seed oil produced from the plant exhibits the following characteristics:

1) contains oleic acid at a level of at least 80% by weight of the total fatty acid content of the seeds;

2) contains linoleic acid at a level less than 4% by weight of the total fatty acid content of the seeds;

3) contains linolenic acid at a level less than 5% by weight of the total fatty acid content of the seeds;

4) the ratio of the quantity of linoleic acid to linolenic acid is less than 1; and 5) has increased oxidative stability for at least 32 hours as compared to a corresponding control.

14. The method of claim 13, wherein the method further comprises isolating seeds from the plant and extracting oil from the seeds.

\* \* \* \* \*